(12) United States Patent
Clausen et al.

(10) Patent No.: US 12,201,537 B2
(45) Date of Patent: Jan. 21, 2025

(54) PROSTHETIC FOOT WITH LAYERS OF FIBROUS MATERIAL

(71) Applicant: Össur Iceland ehf, Reykjavík (IS)

(72) Inventors: Arinbjörn Viggo Clausen, Reykjavik (IS); Christophe Guy Lecomte, Reykjavik (IS); Maria Gudrun Sveinbjornsdottir, Mosfellsbaer (IS); Aron Kristbjorn Albertsson, Hafnarfjordur (IS)

(73) Assignee: Össur Iceland ehf, Reykjavík (IS)

( * ) Notice: Subject to any disclaimer, the term of this patent is extended or adjusted under 35 U.S.C. 154(b) by 381 days.

(21) Appl. No.: 17/534,326

(22) Filed: Nov. 23, 2021

(65) Prior Publication Data
US 2022/0168117 A1 Jun. 2, 2022

Related U.S. Application Data

(60) Provisional application No. 63/261,137, filed on Sep. 13, 2021, provisional application No. 63/119,163, filed on Nov. 30, 2020.

(51) Int. Cl.
*A61F 2/50* (2006.01)
*A61F 2/66* (2006.01)
(Continued)

(52) U.S. Cl.
CPC .......... *A61F 2/5044* (2013.01); *A61H 3/0288* (2013.01); *A61F 2002/5053* (2013.01);
(Continued)

(58) Field of Classification Search
CPC ............... A61H 3/02; A61H 3/0277; A61H 2003/0211; A61F 2002/30971;
(Continued)

(56) References Cited

U.S. PATENT DOCUMENTS

| 511,942 A | 1/1894 | Glanville |
|---|---|---|
| 2,003,961 A | 6/1935 | Vittengl |

(Continued)

FOREIGN PATENT DOCUMENTS

| CN | 1529573 | 9/2004 |
|---|---|---|
| CN | 1835721 | 9/2009 |

(Continued)

OTHER PUBLICATIONS

Antenna. Amazon New Carbon Fiber Car Roof Antenna, Shark Fin Antenna Aerial, AM/FM Signal Aerial, Universal fits for 2019 Acura MDX Sport Utility 4-Door. (Year: 2019).*

(Continued)

*Primary Examiner* — Christie Bahena
(74) *Attorney, Agent, or Firm* — Knobbe Martens Olson & Bear LLP

(57) ABSTRACT

A prosthetic foot including a continuous body extending from a proximal end to a distal end. The body includes an anterior surface, a posterior surface opposite the anterior surface, and a fin on the posterior surface. A prosthetic foot can include a first footplate and a second footplate. The first footplate extends between a proximal portion and a distal portion. The proximal and distal portions of the first footplate are configured to operatively engage a support surface during ambulation. The second footplate extends between a proximal portion and a distal portion. The distal portion of the second footplate is coupled to the first footplate at an intermediate location between the proximal and distal portions of the first footplate. The second footplate incudes an anterior surface, a posterior surface opposite the anterior surface, and a fin on the posterior surface.

13 Claims, 40 Drawing Sheets

(51) Int. Cl.
  *A61H 3/02* (2006.01)
  *B29C 70/46* (2006.01)
  *B29L 31/00* (2006.01)

(52) U.S. Cl.
  CPC .......... *A61F 2002/5055* (2013.01); *A61F 2002/6614* (2013.01); *A61F 2210/0076* (2013.01); *B29C 70/46* (2013.01); *B29L 2031/7532* (2013.01)

(58) Field of Classification Search
  CPC ...... A61F 2002/5056; A61F 2002/6641; A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692; A61F 2/66
  See application file for complete search history.

(56) References Cited

U.S. PATENT DOCUMENTS

| | | | |
|---|---|---|---|
| 2,556,525 | A | 6/1951 | Drennon |
| 3,098,239 | A | 7/1963 | Nader |
| 3,461,464 | A | 8/1969 | Lindgren |
| 3,894,437 | A | 7/1975 | Hagy et al. |
| 4,177,525 | A | 12/1979 | Arbogast et al. |
| 4,267,728 | A | 5/1981 | Manley et al. |
| 4,268,468 | A | 5/1981 | Esper et al. |
| 4,416,293 | A | 11/1983 | Anderson et al. |
| 4,506,395 | A | 3/1985 | Haupt |
| 4,507,879 | A | 4/1985 | Dassler |
| 4,547,913 | A | 10/1985 | Phillips |
| 4,619,661 | A | 10/1986 | Axelsson |
| 4,631,676 | A | 12/1986 | Pugh |
| 4,645,509 | A | 2/1987 | Poggi et al. |
| 4,652,266 | A | 3/1987 | Truesdell |
| 4,659,624 | A | 4/1987 | Yeager et al. |
| 4,791,736 | A | 12/1988 | Phillips |
| 4,813,436 | A | 3/1989 | Au |
| 4,814,661 | A | 3/1989 | Ratzlaff et al. |
| 4,858,621 | A | 8/1989 | Franks |
| 4,859,243 | A | 8/1989 | Hattori et al. |
| 4,889,355 | A | 12/1989 | Trimble |
| 4,938,776 | A | 7/1990 | Masinter |
| 5,019,109 | A | 5/1991 | Voisin |
| 5,064,438 | A | 11/1991 | Naeder |
| 5,112,356 | A | 5/1992 | Harris et al. |
| 5,116,384 | A | 5/1992 | Wilson et al. |
| 5,116,385 | A | 5/1992 | Allard et al. |
| 5,128,880 | A | 7/1992 | White |
| 5,156,631 | A | 10/1992 | Merlette |
| 5,156,632 | A | 10/1992 | Wellershaus et al. |
| 5,181,932 | A | 1/1993 | Phillips |
| 5,219,365 | A | 6/1993 | Sabolich |
| 5,237,520 | A | 8/1993 | White |
| 5,248,467 | A | 9/1993 | Cushman |
| 5,253,656 | A | 10/1993 | Rincoe et al. |
| 5,258,038 | A | 11/1993 | Robinson et al. |
| 5,312,579 | A | 5/1994 | Druyun et al. |
| 5,361,133 | A | 11/1994 | Brown et al. |
| 5,387,246 | A | 2/1995 | Phillips |
| 5,388,591 | A | 2/1995 | De Luca et al. |
| 5,408,873 | A | 4/1995 | Schmidt et al. |
| 5,425,781 | A | 6/1995 | Allard et al. |
| 5,443,522 | A | 8/1995 | Hiemisch |
| 5,443,527 | A | 8/1995 | Wilson |
| 5,471,405 | A | 11/1995 | Marsh |
| 5,474,087 | A | 12/1995 | Nashner |
| 5,514,185 | A | 5/1996 | Phillips |
| 5,545,234 | A | 8/1996 | Collier, Jr. |
| 5,549,711 | A | 8/1996 | Bryant |
| 5,565,162 | A | 10/1996 | Foster |
| 5,623,944 | A | 4/1997 | Nashner |
| 5,695,526 | A | 12/1997 | Wilson |
| 5,695,527 | A | 12/1997 | Allen |
| 5,753,931 | A | 5/1998 | Borchers et al. |
| 5,766,264 | A | 6/1998 | Lundt |
| 5,790,256 | A | 8/1998 | Brown et al. |
| 5,824,112 | A | 10/1998 | Phillips |
| 5,885,229 | A | 3/1999 | Yamato et al. |
| 5,897,594 | A | 4/1999 | Martin et al. |
| 5,944,760 | A | 8/1999 | Christensen |
| 5,957,870 | A | 9/1999 | Yamato et al. |
| 5,993,488 | A | 11/1999 | Phillips |
| 6,054,003 | A | 4/2000 | Bak et al. |
| 6,063,046 | A | 5/2000 | Allum |
| 6,099,572 | A | 8/2000 | Mosler et al. |
| 6,165,227 | A | 12/2000 | Phillips |
| 6,187,052 | B1 | 2/2001 | Molino et al. |
| 6,197,067 | B1 | 3/2001 | Shorter et al. |
| 6,205,230 | B1 | 3/2001 | Sundman et al. |
| 6,206,934 | B1 | 3/2001 | Phillips |
| 6,216,545 | B1 | 4/2001 | Taylor |
| 6,231,527 | B1 | 5/2001 | Sol |
| 6,261,324 | B1 | 7/2001 | Merlette |
| 6,289,107 | B1 | 9/2001 | Borchers et al. |
| 6,290,730 | B1 | 9/2001 | Pitkin et al. |
| 6,331,893 | B1 | 12/2001 | Brown et al. |
| 6,387,134 | B1 | 5/2002 | Parker et al. |
| 6,398,818 | B1 | 6/2002 | Merlette et al. |
| 6,402,790 | B1 | 6/2002 | Celebi |
| 6,443,995 | B1 | 9/2002 | Townsend et al. |
| 6,546,356 | B1 | 4/2003 | Genest |
| 6,602,295 | B1 | 8/2003 | Doddroe et al. |
| 6,663,672 | B1 | 12/2003 | Laghi |
| 6,676,708 | B1 | 1/2004 | Aldo |
| 6,699,295 | B2 | 3/2004 | Lee et al. |
| 6,702,859 | B1 | 3/2004 | Laghi |
| 6,702,860 | B1 | 3/2004 | Aldo |
| 6,706,075 | B1 | 3/2004 | Laghi |
| 6,712,860 | B2 | 3/2004 | Rubie et al. |
| 6,719,807 | B2 | 4/2004 | Harris |
| 6,743,260 | B2 | 6/2004 | Townsend et al. |
| 6,764,521 | B2 | 7/2004 | Molino et al. |
| 6,764,522 | B1 | 7/2004 | Cehn |
| 6,793,683 | B1 | 9/2004 | Laghi |
| 6,797,009 | B1 | 9/2004 | Laghi |
| 6,807,869 | B2 | 10/2004 | Farringdon et al. |
| 6,811,571 | B1 | 11/2004 | Phillips |
| 6,827,744 | B1 | 12/2004 | Laghi |
| 6,869,451 | B1 | 2/2005 | Laghi |
| 6,875,240 | B1 | 4/2005 | Laghi |
| 6,929,665 | B2 | 8/2005 | Christensen |
| 6,936,074 | B2 | 8/2005 | Townsend et al. |
| 6,942,704 | B2 | 9/2005 | Sulprizio |
| 6,966,933 | B2 | 11/2005 | Christensen |
| 6,969,408 | B2 | 11/2005 | Lecomte et al. |
| 7,044,984 | B2 | 5/2006 | Kuiken |
| 7,045,083 | B2 | 5/2006 | Gardner |
| 7,112,227 | B2 | 9/2006 | Doddroe et al. |
| 7,169,190 | B2 | 1/2007 | Phillips et al. |
| 7,219,449 | B1 | 5/2007 | Hoffberg et al. |
| 7,279,011 | B2 | 10/2007 | Phillips |
| 7,337,680 | B2 | 3/2008 | Kantro |
| 7,347,877 | B2 | 3/2008 | Clausen et al. |
| 7,354,456 | B2 | 4/2008 | Phillips |
| 7,407,619 | B2 | 8/2008 | Anthony et al. |
| 7,429,272 | B2 | 9/2008 | Townsend et al. |
| D579,115 | S | 10/2008 | Rubie et al. |
| 7,531,006 | B2 | 5/2009 | Clausen et al. |
| 7,578,852 | B2 | 8/2009 | Townsend et al. |
| 7,581,454 | B2 | 9/2009 | Clausen et al. |
| 7,611,543 | B2 | 11/2009 | Townsend et al. |
| 7,617,068 | B2 | 11/2009 | Tadin et al. |
| 7,618,464 | B2 | 11/2009 | Christensen |
| 7,637,659 | B2 | 12/2009 | Liu et al. |
| 7,637,957 | B2 | 12/2009 | Ragnarsdottir et al. |
| 7,691,305 | B2 | 4/2010 | Sutton et al. |
| 7,727,285 | B2 | 6/2010 | Christensen et al. |
| 7,815,689 | B2 | 10/2010 | Bédard et al. |
| 7,833,287 | B2 | 11/2010 | Doddroe et al. |
| 7,846,213 | B2 | 12/2010 | Lecomte et al. |

(56) References Cited

U.S. PATENT DOCUMENTS

| | | |
|---|---|---|
| 7,862,622 B2 | 1/2011 | Dunlap et al. |
| 7,867,285 B2 | 1/2011 | Clausen et al. |
| D632,392 S | 2/2011 | Jacobs et al. |
| 7,891,258 B2 | 2/2011 | Clausen et al. |
| D633,618 S | 3/2011 | Johnson et al. |
| 7,926,363 B2 | 4/2011 | Miller et al. |
| 7,998,221 B2 | 8/2011 | Lecomte et al. |
| 8,025,699 B2 | 9/2011 | Lecomte et al. |
| D647,617 S | 10/2011 | Mile |
| 8,048,172 B2 | 11/2011 | Jonsson et al. |
| 8,075,501 B2 | 12/2011 | Miller et al. |
| D653,759 S | 2/2012 | Smith et al. |
| D655,009 S | 2/2012 | L'heureux |
| 8,109,014 B2 | 2/2012 | Miller et al. |
| 8,117,922 B2 | 2/2012 | Xia et al. |
| 8,128,709 B2 | 3/2012 | Thorhallsdottir et al. |
| 8,261,611 B2 | 9/2012 | Kim et al. |
| 8,290,739 B2 | 10/2012 | Tadin et al. |
| 8,317,877 B2 | 11/2012 | Doddroe et al. |
| 8,486,156 B2 | 7/2013 | Jónsson |
| 8,500,825 B2 | 8/2013 | Christensen et al. |
| D689,505 S | 9/2013 | Convay et al. |
| 8,540,781 B2 | 9/2013 | Nissels et al. |
| 8,544,347 B1 | 10/2013 | Berme |
| 8,685,109 B2 | 4/2014 | Clausen et al. |
| 8,734,706 B2 | 5/2014 | Choiniere et al. |
| 8,771,372 B1 | 7/2014 | Rubie et al. |
| 8,992,811 B2 | 3/2015 | Nagakura et al. |
| D731,062 S | 6/2015 | Meyer et al. |
| 9,132,022 B2 | 9/2015 | Lecomte et al. |
| 9,193,113 B2 | 11/2015 | La Forest et al. |
| 9,333,690 B2 | 5/2016 | Bessho et al. |
| 9,561,118 B2 | 2/2017 | Clausen et al. |
| 9,668,887 B2 | 6/2017 | Lecomte et al. |
| D795,433 S | 8/2017 | Clausen et al. |
| D797,292 S | 9/2017 | Clausen et al. |
| 9,968,467 B2 | 5/2018 | Jonsson et al. |
| 9,999,524 B2 | 6/2018 | Clausen et al. |
| 10,105,878 B2 | 10/2018 | Usui et al. |
| 10,369,019 B2 | 8/2019 | Clausen et al. |
| 10,390,974 B2 | 8/2019 | Clausen et al. |
| 10,420,393 B2 | 9/2019 | Saito et al. |
| 11,147,692 B2 | 10/2021 | Clausen et al. |
| 11,285,024 B2 | 3/2022 | Clausen et al. |
| 2002/0013628 A1 | 1/2002 | Harris |
| 2002/0040249 A1 | 4/2002 | Phillips |
| 2002/0082713 A1 | 6/2002 | Townsend et al. |
| 2002/0087216 A1 | 7/2002 | Atkinson et al. |
| 2002/0116072 A1 | 8/2002 | Rubie et al. |
| 2002/0128727 A1 | 9/2002 | Merlette et al. |
| 2002/0138923 A1 | 10/2002 | Shaffeeullah |
| 2002/0143408 A1 | 10/2002 | Townsend et al. |
| 2003/0009911 A1 | 1/2003 | Brown |
| 2003/0045944 A1 | 5/2003 | Mosler Luder et al. |
| 2003/0093158 A1 | 5/2003 | Phillips et al. |
| 2003/0191540 A1 | 10/2003 | Townsend et al. |
| 2004/0064195 A1 | 4/2004 | Herr |
| 2004/0068327 A1 | 4/2004 | Christensen |
| 2004/0102726 A1 | 5/2004 | Sullivan |
| 2004/0112138 A1 | 6/2004 | Knirck et al. |
| 2004/0122529 A1 | 6/2004 | Townsend et al. |
| 2004/0162623 A1 | 8/2004 | Phillips |
| 2004/0181289 A1 | 9/2004 | Bédard et al. |
| 2004/0199265 A1 | 10/2004 | Townsend et al. |
| 2004/0225376 A1 | 11/2004 | Townsend et al. |
| 2004/0261155 A1 | 12/2004 | Agathos et al. |
| 2005/0033450 A1 | 2/2005 | Christensen |
| 2005/0033451 A1 | 2/2005 | Aigner et al. |
| 2005/0038524 A1 | 2/2005 | Jonsson et al. |
| 2005/0038525 A1 | 2/2005 | Doddroe et al. |
| 2005/0060045 A1 | 3/2005 | Smith et al. |
| 2005/0071017 A1 | 3/2005 | Lecomte et al. |
| 2005/0071018 A1 | 3/2005 | Phillips et al. |
| 2005/0097970 A1 | 5/2005 | Nurse |
| 2005/0107889 A1 | 5/2005 | Bédard et al. |
| 2005/0109563 A1 | 5/2005 | Vitale et al. |
| 2005/0119763 A1 | 6/2005 | Christensen |
| 2005/0137717 A1 | 6/2005 | Gramnaes |
| 2005/0177250 A1 | 8/2005 | Townsend et al. |
| 2005/0187640 A1 | 8/2005 | Christensen |
| 2005/0203640 A1 | 9/2005 | Christensen |
| 2005/0216097 A1 | 9/2005 | Rifkin |
| 2005/0234563 A1 | 10/2005 | Phillips |
| 2005/0273179 A1 | 12/2005 | Townsend et al. |
| 2006/0004467 A1 | 1/2006 | Lecomte et al. |
| 2006/0015192 A1 | 1/2006 | Thorhallsdottir et al. |
| 2006/0026738 A1 | 2/2006 | Kleinert |
| 2006/0041321 A1 | 2/2006 | Christensen |
| 2006/0069450 A1 | 3/2006 | McCarvill et al. |
| 2006/0167563 A1 | 7/2006 | Johnson et al. |
| 2006/0173555 A1 | 8/2006 | Harn et al. |
| 2006/0247794 A1 | 11/2006 | Doddroe et al. |
| 2007/0027557 A1 | 2/2007 | Jonsson et al. |
| 2007/0039205 A1 | 2/2007 | Peveto et al. |
| 2007/0043582 A1 | 2/2007 | Peveto et al. |
| 2007/0100465 A1 | 5/2007 | Egan |
| 2007/0106395 A9 | 5/2007 | Clausen et al. |
| 2007/0213840 A1 | 9/2007 | Townsend et al. |
| 2007/0250178 A1 | 10/2007 | Wilson |
| 2007/0255427 A1 | 11/2007 | Kloos et al. |
| 2008/0033578 A1 | 2/2008 | Christensen |
| 2008/0033579 A1 | 2/2008 | Phillips et al. |
| 2008/0046096 A1 | 2/2008 | Bédard et al. |
| 2008/0167730 A1 | 7/2008 | Pusch |
| 2008/0183301 A1 | 7/2008 | Christensen |
| 2009/0012630 A1 | 1/2009 | Mosler et al. |
| 2009/0043403 A1 | 2/2009 | Asgeirsson et al. |
| 2009/0049712 A1 | 2/2009 | Steszyn et al. |
| 2009/0076626 A1 | 3/2009 | Ochoa |
| 2009/0105845 A1 | 4/2009 | Curtis |
| 2009/0143870 A1 | 6/2009 | Bédard et al. |
| 2009/0204231 A1 | 8/2009 | Bonacini |
| 2009/0222105 A1 | 9/2009 | Clausen |
| 2009/0234463 A1 | 9/2009 | Wilson |
| 2009/0293641 A1 | 12/2009 | Clausen et al. |
| 2010/0004757 A1 | 1/2010 | Clausen et al. |
| 2010/0023135 A1 | 1/2010 | Rubie et al. |
| 2010/0324699 A1 | 12/2010 | Herr et al. |
| 2011/0093089 A1 | 4/2011 | Martin |
| 2011/0146396 A1 | 6/2011 | Kim et al. |
| 2011/0213471 A1 | 9/2011 | Jónsson |
| 2011/0251520 A1 | 10/2011 | Shieh et al. |
| 2011/0288448 A1 | 11/2011 | Sanders et al. |
| 2012/0023776 A1 | 2/2012 | Skaja et al. |
| 2012/0035509 A1 | 2/2012 | Wilson et al. |
| 2012/0151794 A1 | 6/2012 | Hansen et al. |
| 2012/0165958 A1 | 6/2012 | Clausen et al. |
| 2012/0166091 A1 | 6/2012 | Kim et al. |
| 2012/0266648 A1 | 10/2012 | Berme et al. |
| 2013/0018282 A1 | 1/2013 | Mainini et al. |
| 2013/0060349 A1 | 3/2013 | Thorsteinsson et al. |
| 2014/0257523 A1 | 9/2014 | Clausen et al. |
| 2015/0018741 A1 | 1/2015 | Lieberson et al. |
| 2015/0374514 A1 | 12/2015 | Clausen et al. |
| 2016/0176087 A1 | 6/2016 | Menard et al. |
| 2017/0006961 A1 | 1/2017 | Pedersen et al. |
| 2020/0000611 A1 | 1/2020 | Clausen et al. |
| 2022/0079781 A1 | 3/2022 | Clausen et al. |

FOREIGN PATENT DOCUMENTS

| | | | |
|---|---|---|---|
| DE | 298 20 904 | 4/1999 | |
| WO | WO 94/010943 | 5/1994 | |
| WO | WO 94/022398 | 10/1994 | |
| WO | WO 00/027317 | 5/2000 | |
| WO | WO 02/051342 | 7/2002 | |
| WO | WO 2004/032809 | 4/2004 | |
| WO | WO 2005/048887 | 6/2005 | |
| WO | WO-2007035894 A2 * | 3/2007 | ............... A61F 2/66 |
| WO | WO 2011/106564 | 9/2011 | |
| WO | WO 2016/056983 | 4/2016 | |

(56) References Cited

FOREIGN PATENT DOCUMENTS

| WO | WO-2018101983 A1 * | 6/2018 | ............... A61H 3/02 |
| WO | WO-2020012507 A1 * | 1/2020 | ........... A61F 2/5044 |

OTHER PUBLICATIONS

International Search Report and Written Opinion in International Application No. PCT/IB2021/060899 dated Apr. 21, 2022 in 17 pages.
International Preliminary Report on Patentability in International Application No. PCT/IB2021/060899 dated Jun. 15, 2023 in 10 pages.

* cited by examiner

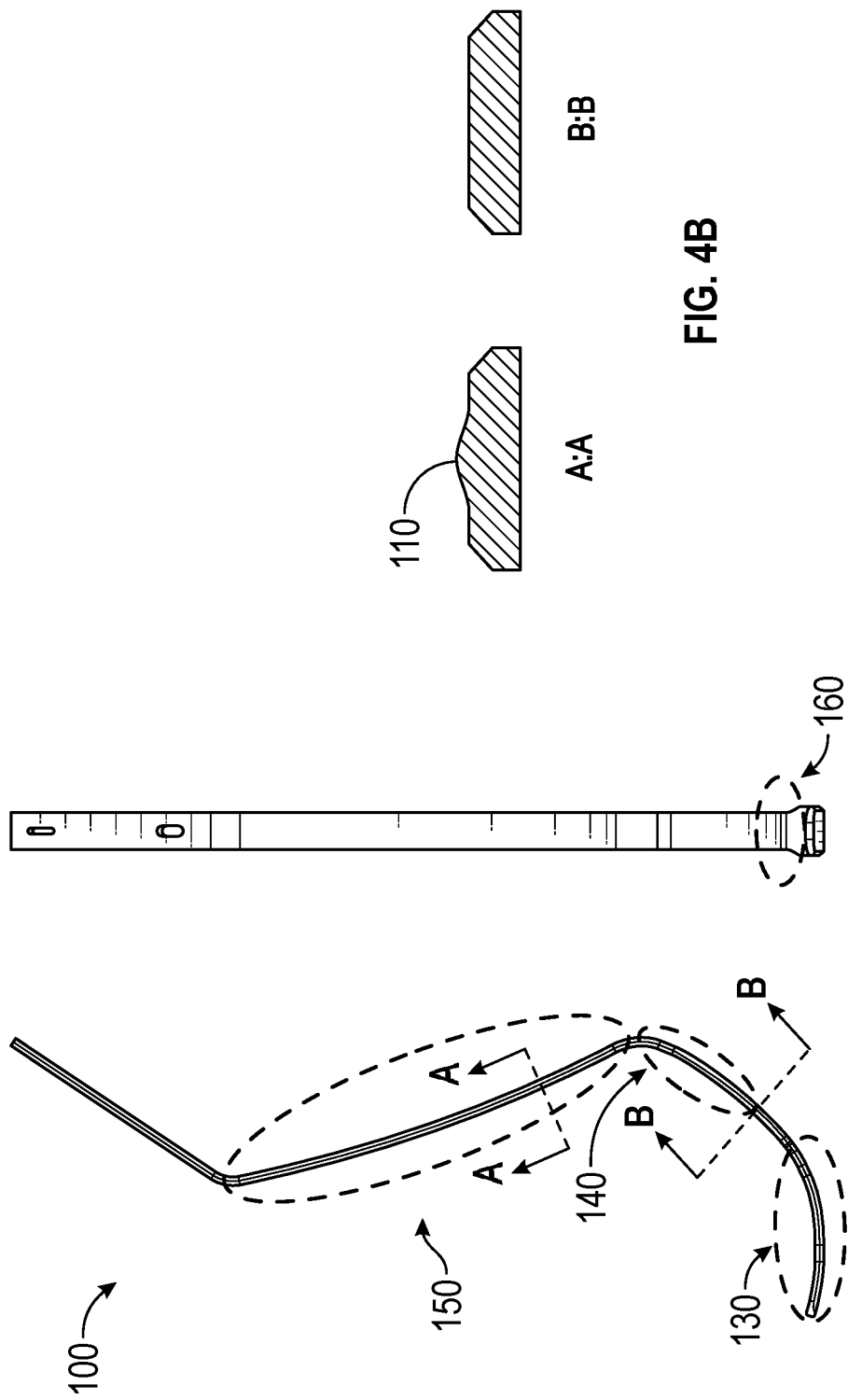

PROSTHETIC FOOT WITH LAYERS OF FIBROUS MATERIAL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims priority benefit of U.S. Provisional Application No. 63/119,163, filed Nov. 30, 2020, and U.S. Provisional Application No. 63/261,137, filed Sep. 13, 2021, the entirety of which is hereby incorporated by reference herein.

BACKGROUND

Field

The present disclosure is related to limb support devices, such as prosthetic or orthotic systems.

Description of the Related Art

A composite material (e.g., carbon fiber reinforced polymers) is a strong, lightweight material used in many different applications including, but not limited to, prosthetics. Polymers (e.g., epoxy) may be used with various types of additives (e.g., silica, carbon nanotubes, carbon fiber layers, and the like) to manufacture composite articles.

When manufacturing composite articles with varied dimensions (that is, objects with varying lengths, widths, thickness, and the like), a block of a composite article may be manufactured first and portions of the block may be removed (e.g., cut). However, such removal of portions of the block of composite article results in the cutting of fibers of the composite material, which may result in delamination and noise in the composite article, and can be a reason for product returns.

SUMMARY

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems and methods of limb support devices and sole systems.

The following disclosure describes non-limiting examples of some embodiments. For instance, other embodiments of the disclosed systems and methods may or may not include the features described herein. Moreover, disclosed advantages and benefits can apply only to certain embodiments of the invention and should not be used to limit the disclosure.

In accordance with one aspect, a composite article is disclosed. The composite article may be manufactured from layers of composite material. The composite article can include a first portion having a first width. The composite article can include a second portion distally positioned from the first portion and having a second width different than the first width. The composite article can include a transition portion located between the first portion and the second portion. The transition portion can have at least a first contour transitioning between the first width and the second width. The composite article can include a plurality of layers of fibrous material extending and continuous between the first portion and the second portion. The composite article can include a first polymer impregnated with the plurality of layers of fibrous material and polymerized during a curing process. The first polymer can cause the plurality of layers of fibrous material to realign to a shape substantially similar to the first contour during the curing process.

In accordance with another aspect, a limb support device is disclosed. In one example, the limb support device is a crutch. In another example, the limb support device is a prosthetic foot. The limb support device can include a body with a proximal portion and a distal portion. The proximal portion can have a first width and the distal portion can have a second width greater than the first width. The body can include a transition portion between the proximal portion and the distal portion. The transition portion can have a tapered width that transitions from the first width to the second width. The body can include a plurality of layers of fibrous material having a plurality of fibers. Each of the fibers can extend linearly and continuously along each of the proximal portion, the transition portion, and the distal portion. The plurality of fibers can be generally parallel to each other and to outer edges of the proximal portion, the distal portion, and the transition portion.

In accordance with another aspect, a modular sole apparatus for a limb support device is disclosed. The modular sole apparatus can include a body. The body can include a support surface configured to receive thereon a body portion of the limb support device. The body can include side supports extending upwards from side edges of the support surface. The body can include a slot at a distal end of the body that is configured to receive a distal end of the body portion of the limb support device. The body can include an attachment mechanism that can releasably engage the limb support device to inhibit decoupling of the body from the limb support device.

In accordance with another aspect, a prosthetic foot is disclosed. The prosthetic foot includes a continuous body extending from a proximal end to a distal end. The body includes an anterior surface, a posterior surface opposite the anterior surface, and a fin on the posterior surface.

In accordance with another aspect, a prosthetic foot is disclosed. The prosthetic foot can include a first footplate and a second footplate. The first footplate extends between a proximal portion and a distal portion. The proximal and distal portions of the first footplate are configured to operatively engage a support surface during ambulation. The second footplate extends between a proximal portion and a distal portion. The distal portion of the second footplate is coupled to the first footplate at an intermediate location between the proximal and distal portions of the first footplate. The second footplate incudes an anterior surface, a posterior surface opposite the anterior surface, and a fin on the posterior surface.

The systems and methods disclosed herein can include several features, no single one of which is solely responsible for their desirable attributes. Without limiting the scope as expressed by the claims that follow, certain features of the limb support devices and the sole systems will now be discussed briefly. One skilled in the art will understand how the features of the disclosed technology provide several advantages over traditional systems and methods.

BRIEF DESCRIPTION OF THE DRAWINGS

Various embodiments will be described hereinafter with reference to the accompanying drawings. The drawings and the associated descriptions are provided to illustrate embodiments of the present disclosure and do not limit the scope of the claims. In the drawings, similar elements have similar reference numerals.

FIG. 4A shows a side view and a front view of an example limb support device.

FIG. 4B shows cross-sectional views of the limb support device of FIG. 4A.

Figure 1:
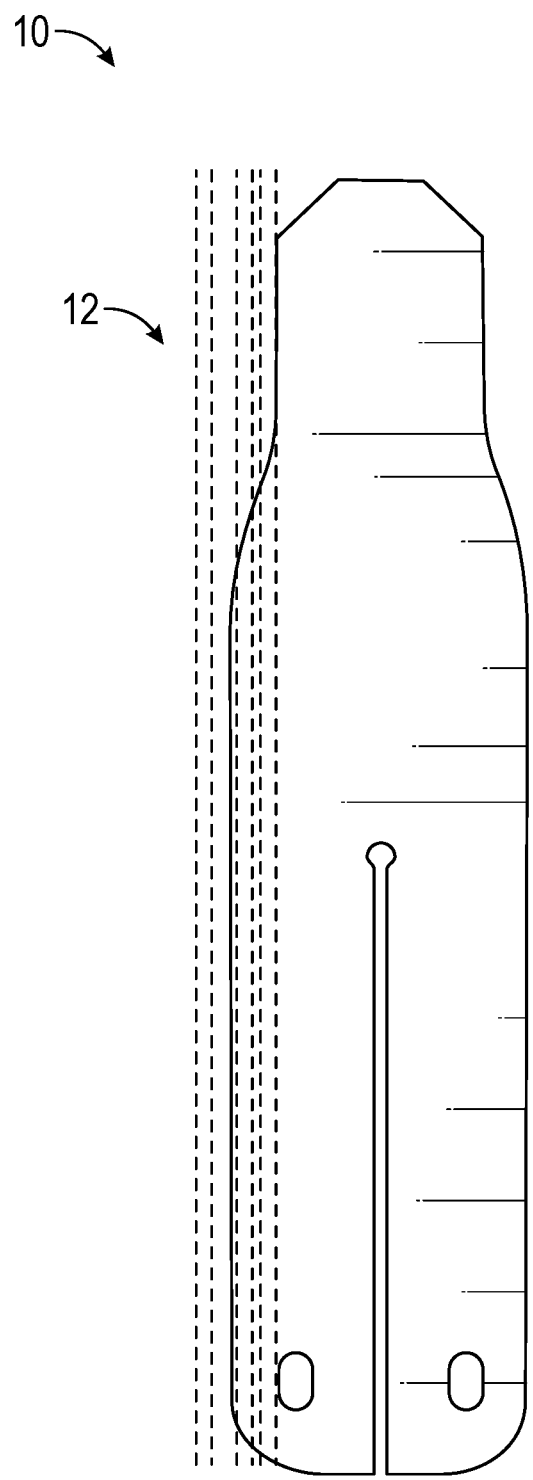
FIG. 1 is a schematic illustration of a portion of an existing limb support device with varying widths

The foregoing and other features of the present development will become more fully apparent from the following description and appended claims, taken in conjunction with the accompanying drawings. Understanding that these drawings depict only several embodiments in accordance with the development and are not to be considered limiting of its scope, the development will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present development, as generally described herein, and illustrated in the drawings, can be arranged, substituted, combined, and designed in a wide variety of different configurations, all of which are explicitly contemplated and make part of this disclosure.

DETAILED DESCRIPTION

Although certain embodiments and examples are described herein, this disclosure extends beyond the specifically disclosed embodiments and/or uses and obvious modifications and equivalents thereof. Thus, it is intended that the scope of this disclosure should not be limited by any particular embodiments described below.

Previous methods of manufacturing a composite article (e.g., a prosthetic foot) with varying dimensions using layers of fibrous material (e.g., carbon fiber) include curing a block of a composite material and removing portion of the composite material to create shapes with varying dimensions. For example, manufacturing a footplate 10 shown in FIG. 1 would include curing a composite block having a width of a toe section and removing (e.g., cutting) portions of the block to create a heel section having a smaller width than the toe section.

Previous methods of manufacturing a composite article include placing layers of, for example, fibrous material in a linear orientation illustrated by lines 12. When portions of a block of composite material is removed (e.g., cut away), some of the layers of fibrous material would be cut and be exposed at edges of a final product, as shown in FIG. 1.

Figure 2:
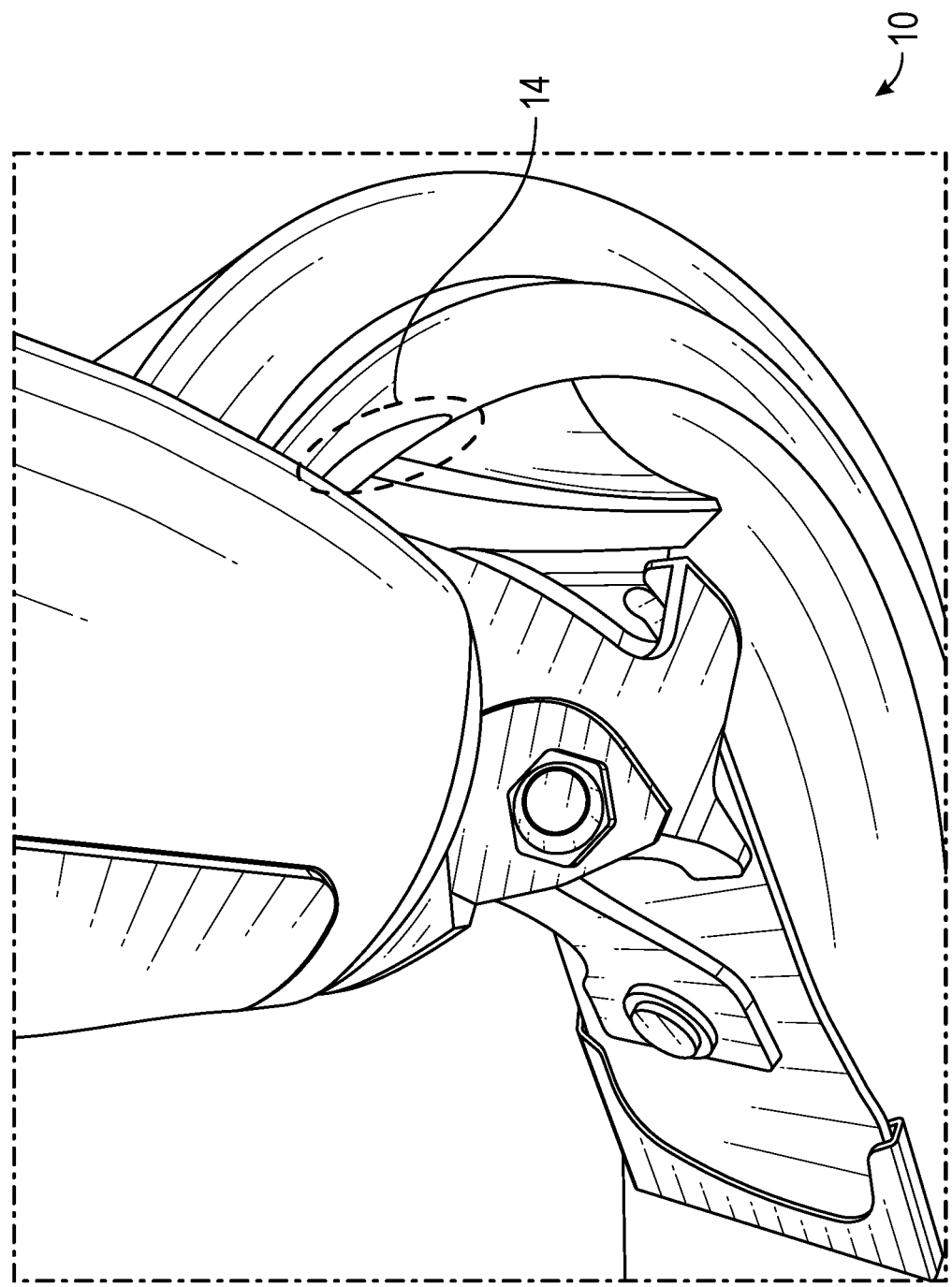
FIG. 2 shows a portion of an example of an existing limb support device with a splinter.

The exposed edges of the layers of fibrous material can, over time, lead to splinters forming at the outer edge of, for example, a prosthetic foot. FIG. 2 illustrates an example of splinters 14 at an outer edge of a prosthetic foot made as described above by cutting material to produce a footplate of varying width. The splinters 14 can be created by cyclic bending of a composite article at areas near where the exposed edges of the layers are present. Splinters 14 can result in delamination and noise in the prosthetic foot, and can be a reason for product returns.

Figure 3A:
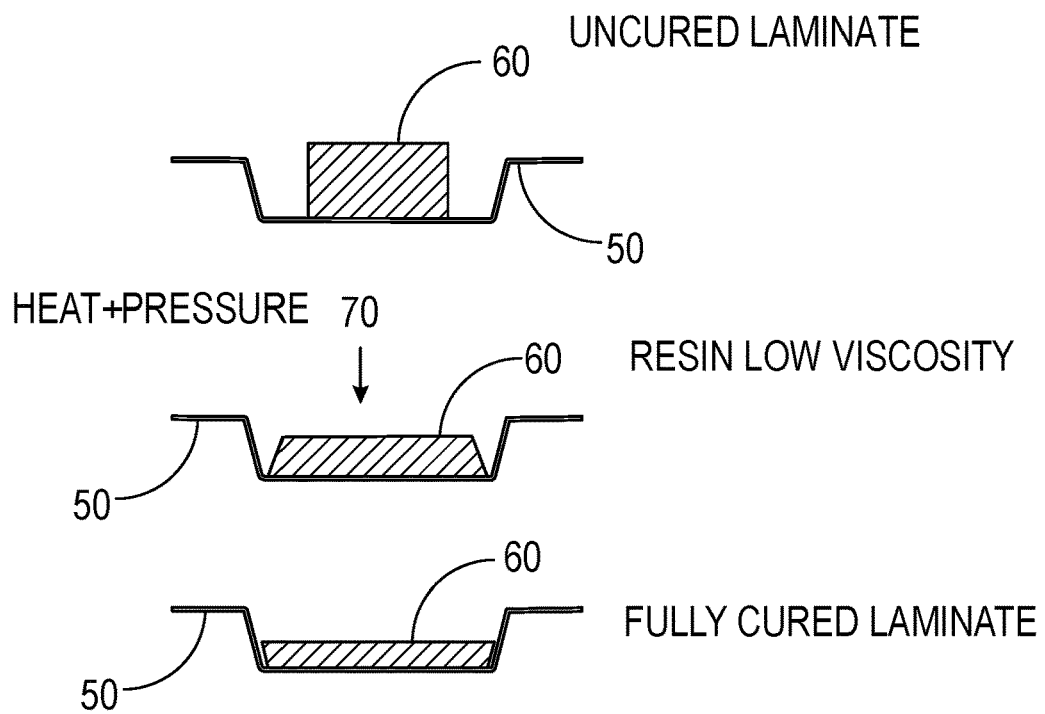
FIG. 3A is schematic illustration of a side view of a mold with varying widths with uncured composite material.
Figure 3B:
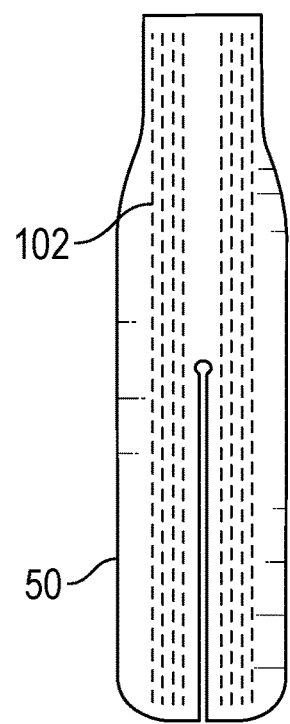
FIG. 3B is a schematic illustration of a top view of the mold of FIG. 3A, schematically illustrating uncured composite materials.

The method of manufacturing composite articles described herein advantageously eliminate the need to remove portions of a composite material. In some implementations, a mold having a desired shape (e.g., having the shape of a limb support device 100 shown in FIG. 3D) may be used. An example method of manufacturing composite articles is schematically illustrated in FIG. 3A. Layers of, for example, fibrous material 60 may be placed in a mold 50 in a manner illustrated by lines 102 as shown in FIG. 3B. The layer of fibrous material 60 may be uncured laminate. Once a curing process is applied to the layers, the layers may fill the cavity of the mold and realign in the desired shape (e.g., a shape of the mold). In some implementations, the curing process include applying heat and pressure 70 to the layers of fibrous material placed in the mold. The pressure (and/or heat) applied to the layers can cause the layers to fill the mold 50. The heat applied can increase viscosity of the layers of fibrous material 60 (e.g., uncured laminate) so that the layers of fibrous material 60 can fill the mold. In some implementations, a curing agent may be added before or during the curing process to help with the curing of the layers of fibrous material 60. The curing agent can be a thermoset matrix (e.g., resins such as epoxide, Polyurethane, unsaturated polyester, phenolic, cyanate ester, vinyl, silicones, bis-maleimide, etc.) or a thermoplastic matrix (e.g., resins such as polycarbonate, acrylic, nylon, polyethylene, polypropylene, polystyrene, polyvinyl chloride, fluoropolymers (Teflon), acetal polyoxymethylene, etc.). In the example illustration shown in FIG. 3C, the layers of fibrous material 60 may be placed and cured in a mold in a manner illustrated by lines 102. In some examples, the layers of fibrous material 60 may be placed in a manner such that some of the layers (e.g., layers closer to the edges of the mold) may correspond to (e.g., track or approximate) an overall shape of the mold as shown in FIG. 3C, as opposed to being placed in a mold in a linear manner as illustrated by lines 102 in FIG. 3B.

In some implementations, the amount of heat applied during curing can vary depending on a curing agent or a composite material used. For example, between about 50 degree Celsius and about 200 degree Celsius of heat may be applied during the curing process. When the amount of heat is reduced, the amount of time needed for curing may increase, and vice versa.

Figure 3C:
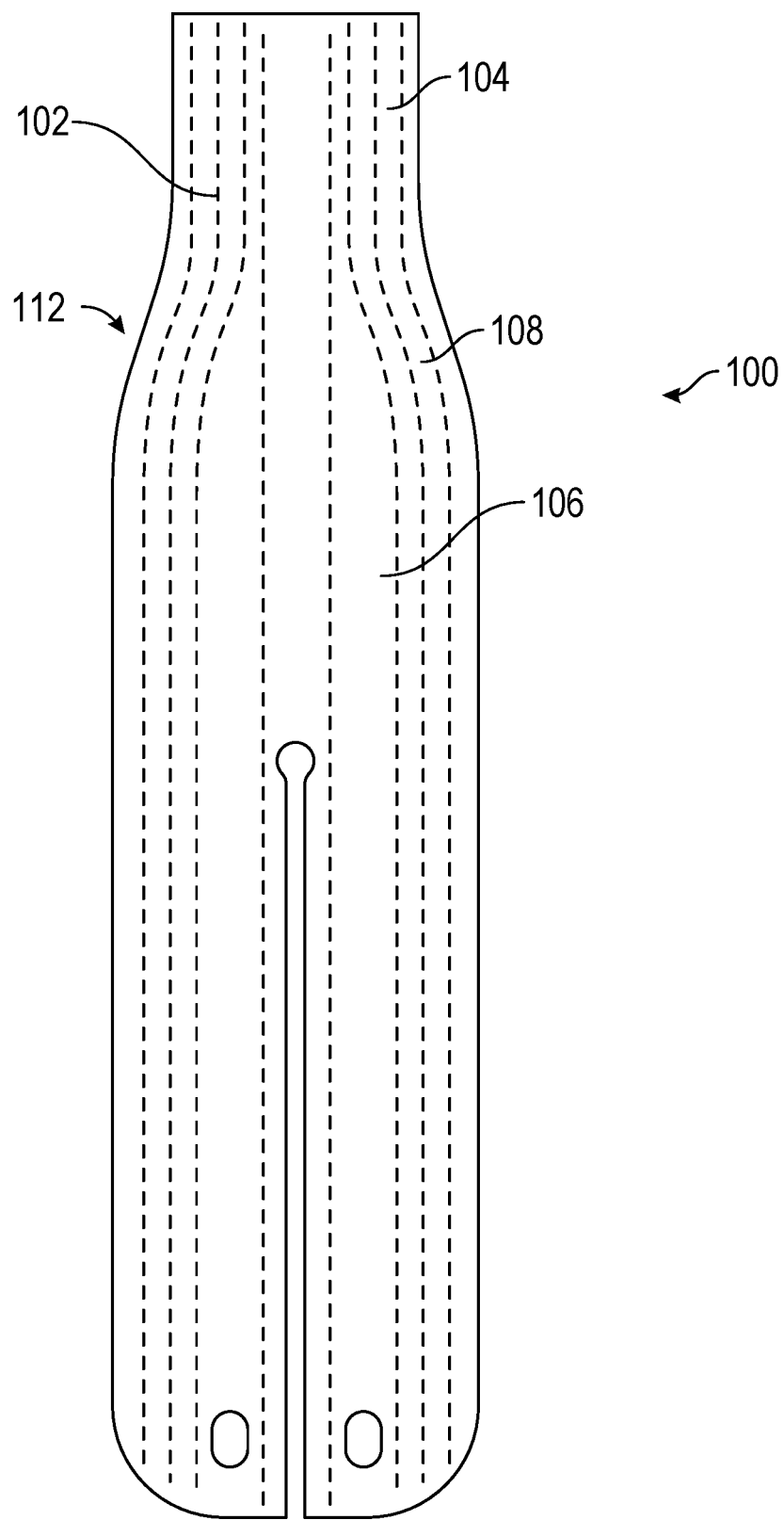
FIG. 3C is a schematic illustration of a top view of the mold of FIG. 3A, schematically illustrating cured composite materials.

FIG. 3C illustrate a portion of an example limb support device 100 manufactured using the method schematically illustrated by FIG. 3A. The limb support device 100 can be a prosthetic foot. In some example, the limb support device 100 can be a crutch. The limb support device 100 may be a blade of a crutch or a prosthetic footplate. As discussed above, a mold (e.g., the mold 50) having a shape of the limb support device 100 may be used. Layers of fibrous materials (e.g., the layers of fibrous material 60) may be placed in the mold and cured. In some implementations, the layers of fibrous materials may be impregnated with curing agent. During a curing process, the layers may fill the mold and realign in a desired shape/contour. In some implementations, a curing agent may be added before or during the curing process and aid the layers to fill the mold and assume a shape corresponding to (e.g., approximating) a contour of the mold. In another example, the expansion of the curing agent may cause at least one of the layers of fibrous material to realign with the contour of the mold used. Since the mold has the desired shape of the limb support device 100, the limb support device 100 does not need to be cut into a desired shape once it is removed from the mold, other than minor sanding or smoothing process. Therefore the layers of fibrous material do not need to be cut and outer edges of the limb support device 100 do not include cut and exposed fibrous materials, thereby advantageously inhibiting (e.g., preventing or avoiding) delamination of the fibers.

Figure 3D:
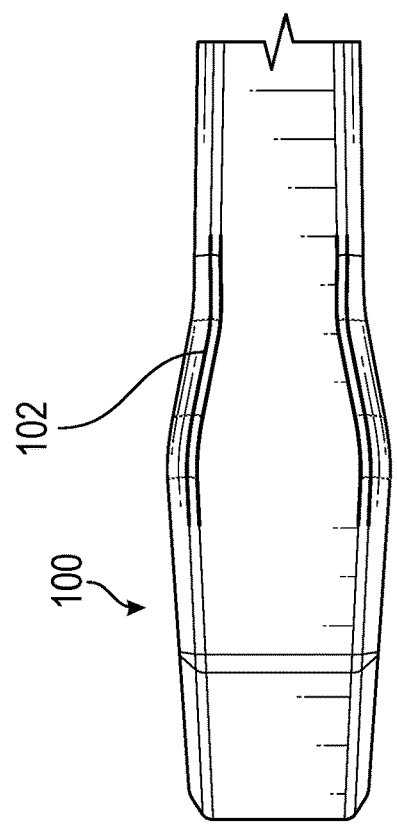
FIG. 3D is a bottom view of a portion of an example limb support device with varying widths.
Figure 3D:
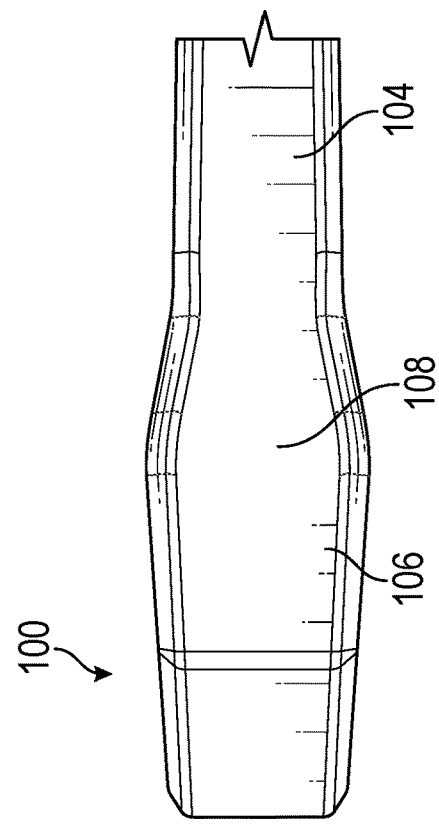

In the example illustrated by FIG. 3C, the limb support device 100 can include a first portion 104, a second portion 106, and a transition portion 108. The first portion 104 can have a first width and the second portion 106 can have a second width. The second width can be different from the first width. For example, the width of the second portion 106 (that is, the second width) may be greater than that of the first portion 104 (that is, the first width). The transition portion 108 can be between the first portion 104 and the second portion 106, and its outer edges can correspond to a change of the width of the limb support device 100 between the first portion 104 and the second portion 106. The width of the transition portion 108 can taper (e.g., linearly or in a curved manner) between the second width and the first width with a contour 112. For example, the width of the transition portion 108 can transition from the first width to the second width. FIG. 3D illustrates an example of the limb support device 100 manufactured using the mold 50 shown in FIG. 3B.

When layers of fibrous material are added into a mold, the layers may be a rectangular block of uncured laminate and may not have a desired contour of the limb support device 100. A laminate may include composite fibers (e.g., carbon fibers or glass fibers) and/or curing agent. In some implementations, some of the layers (e.g., ones placed substantially middle of a mold) may be placed in a linear orientation while other layers (e.g., ones placed closer to side edges of a mold) may be placed in a non-linear orientation (e.g., curved). The layers of fibrous material may extend between the first portion 104 and the second portion 106 via the transition portion 108 continuously without any breaks. As discussed herein, the layers may fill the mold during a curing process such that at least some of the layers of fibrous material realign to the contour of the mold. The curing process, for example, may include application of heat and pressure directly to the layers of fibrous material (e.g., uncured laminate) to allow the layers to fill the mold. As such, at least some of the fiber in the layers of fibrous material may realign to a contour of the mold.

The improved method of manufacturing composite articles (e.g., limb support device 100) can advantageously reduce the manufacturing cost of composite articles such as prosthetic devices. Since the improved method eliminates the need to remove (e.g., cut away) portion of a block of composite material to achieve a desired shape of the composite material, it can reduce or eliminate the amount of waste produced during manufacturing process. In addition, the improved method of manufacturing composite articles can advantageously improve the structural integrity of the end products (e.g., crutch or prosthetic foot). Since the improved method does not involve removing a portion of a block of composite material, edges of layers of fibrous material may not be exposed and therefore reduce the likelihood of delamination or the product developing splinters over time.

Figure 4C:
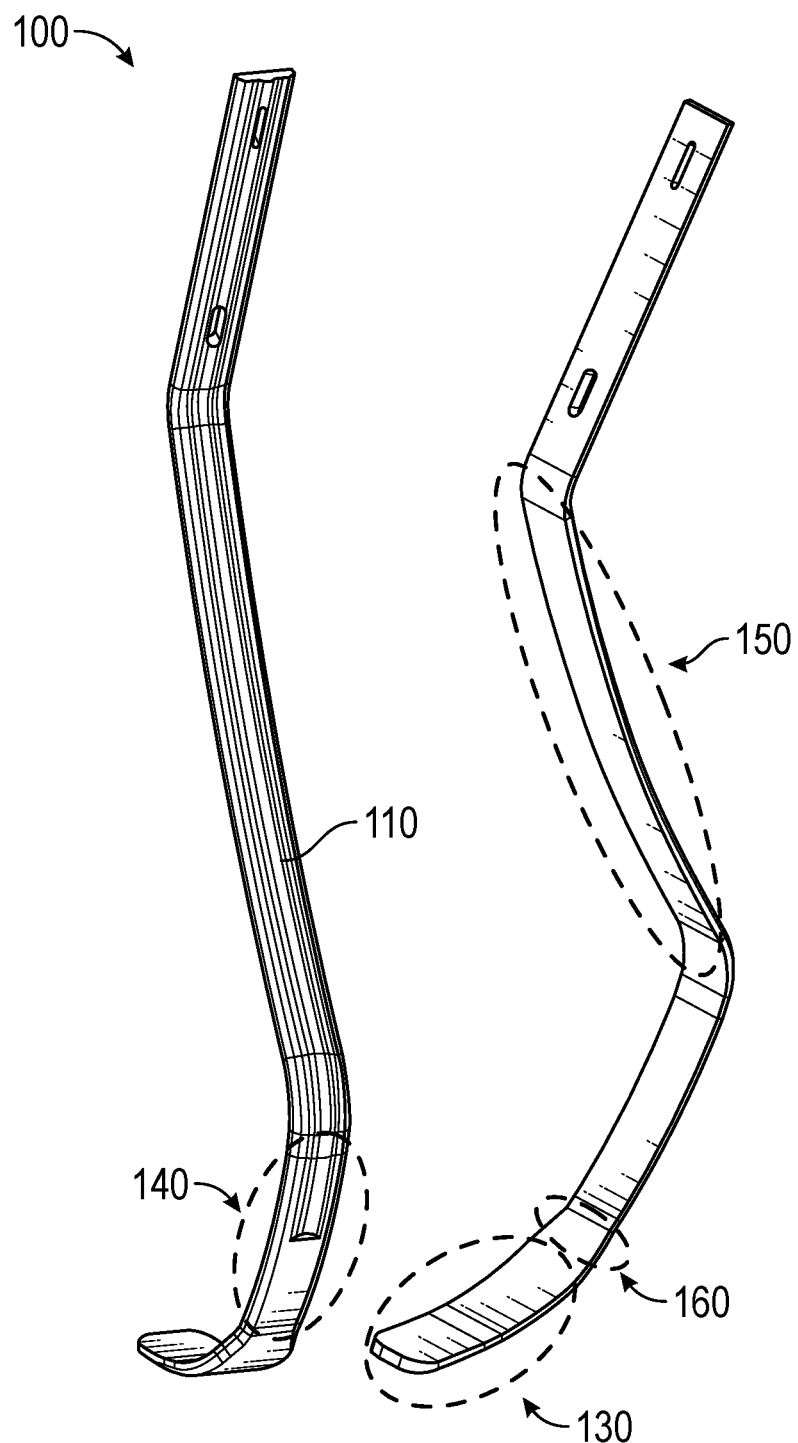
FIG. 4C shows various perspective views of the limb support device of FIG. 4A.

The structural integrity of a composite article (e.g., the limb support device 100) may further be improved by adding a protruded structure. FIGS. 4A and 4C show various views of the limb support device 100 (e.g., a prosthetic crutch) having a protruded structure (e.g., a fin). In the example illustrated in FIGS. 4A and 4C, the limb support device 100 may include a fin 110 formed on a rear surface thereof. In some implementations, the fin 110 may be formed on a front surface thereof. In some implementations, the fin 110 may be formed on both the front and the rear surface thereof. Though the limb support device 100 shown in FIGS. 4A-4C is a crutch, the features (e.g., the fin 100) discussed in connection with FIGS. 4A-4C can also be incorporated into other limb support devices (e.g., a prosthetic footplate).

FIG. 4B shows different cross-sections of the limb support device 100. A cross-section B-B of the limb support device 100 includes the fin 110 while a cross-section A-A of the limb support device 110 does not include the fin 110. As shown in FIG. 4B, the fin 110 may be a generally triangular or contoured protrusion extending away from, for example, the rear surface of the limb support device 100. In some embodiments, the fin 110 may be semi-circular, trapezoidal, semi-elliptical, rectangular, or any suitable shape to increase stiffness of the limb support device 100.

In some implementations, the limb support device 100 can include chamfered surfaces 143 (see FIGS. 6A-6B) that may be positioned between a rear surface (that is, a surface that faces rearward during use of the limb support device 100) or a front surface (that is, a surface that faces forward during use of the limb support device 100) and the side surfaces.

In some implementations, the fin 110 can increase the thickness of the centerline of the limb support device 100. Additionally and/or alternatively, the thickness of the outer edges of the limb support device 100 may be reduced when the limb support device 100 includes the fin 110. In some implementations, the thickness of the outer edges of the limb support device 100 may remain the same regardless of whether the limb support device 100 includes the fin 110.

The fin 110 can be added to various portions of the limb support device 100. For example, as discussed herein and shown in FIGS. 4A and 4C, the limb support device 100 can be a crutch having a foot portion 130, an ankle portion 140, and a calf portion 150. The foot portion 130 and the ankle portion 140 can have a varying width and be connected via a transition portion 160 with a tapering width between the width of the foot portion 130 and the width of the ankle portion 140. The fin 110 can extend over at least a portion or the entirety of a portion of the limb support device 100. The fin 110 can extend over one or more portions of the limb support device 100. For example, as shown in FIG. 4C, the fin 110 can extend over the ankle portion 140 and the calf portion 150 of the limb support device 100. In another example, the fin 110 may extend over just the ankle portion 140 of the limb support device 100.

In some implementations, the fin 110 can be localized in certain areas of the limb support device 100. For example, the fin 110 can be localized in an area of the limb support device 100 where the ankle portion 140 connects with the calf portion 150. As such the fin 110 may increase stiffness of the limb support device 100 at certain, desired locations.

Figure 5:
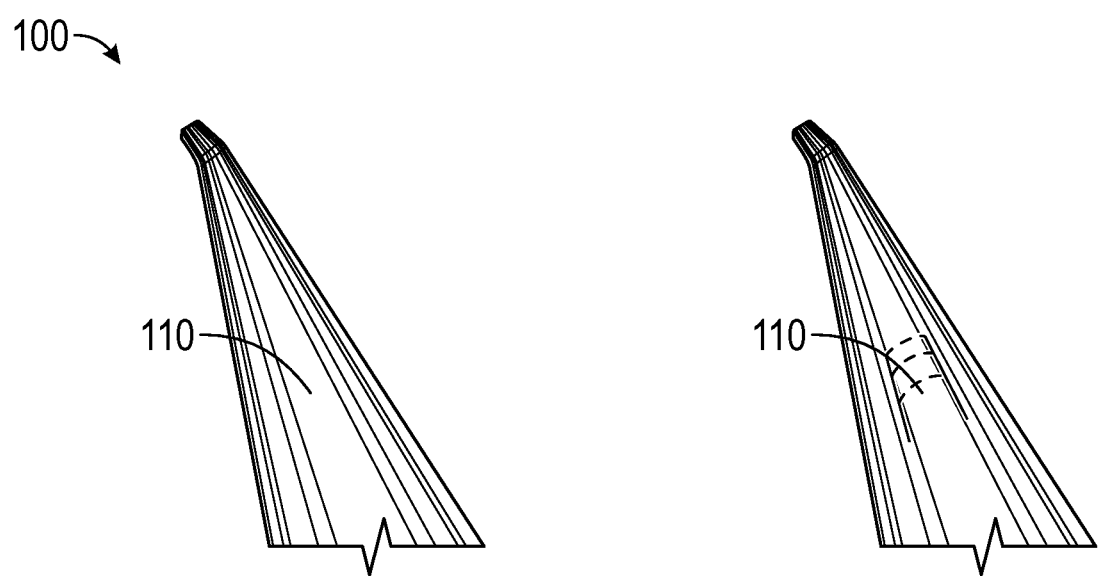
FIG. 5 shows a side perspective view of a portion of an example limb support device with a fin.

FIG. 5 illustrates a perspective view of a calf portion of an example limb support device 100. In the example illustrated in FIG. 5, the calf portion of the limb support device 100 includes the fin 110 extending along the entire length of the calf portion where the fin 110 is a rounded-edge formed on a back side of the calf portion.

Figure 6A:
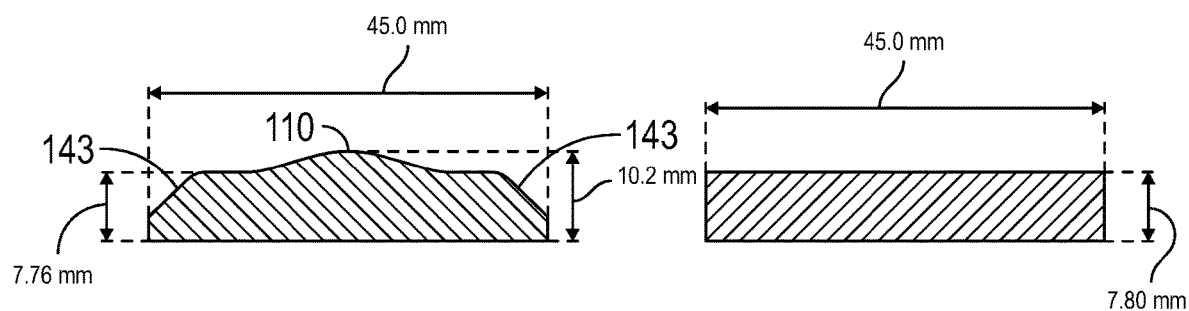
FIGS. 6A and 6B show various cross-sectional views and dimensions of an example limb support device.
Figure 6B:
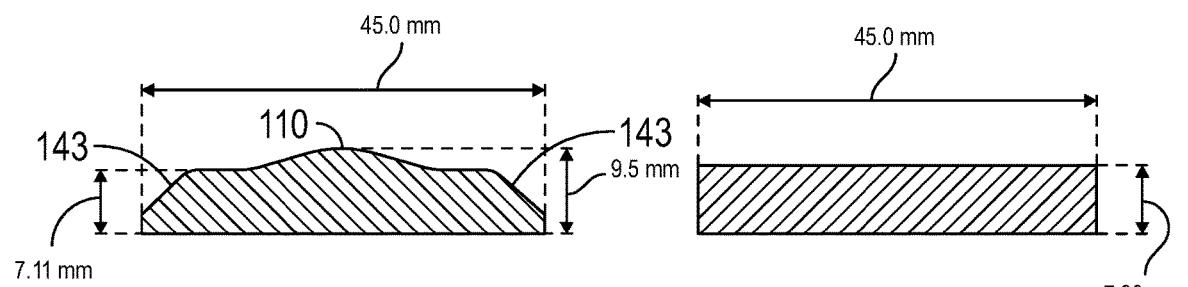

In some implementations, adding the fin 110 to the limb support device 100 (e.g., a blade of a crutch) can allow manufacturers to increase the level of stiffness for the limb support device 100 using the same amount of material. FIGS. 6A and 6B show example cross-sectional dimensions of the limb support device 100 with and without the fin 110. FIG. 6A shows an example cross-sectional areas of the limb support device 100 with and without the fin 110 that are the same (that is, 351 mm²).

To determine the level of stiffness of the limb support device 100 with and without the fin 110, a single load cantilever beam deflection formula may be used. The single load cantilever beam deflection formula is shown below:

$$\delta = FL/3EI$$

where F is the force applied on a prosthetic device at a single point, L is the length of beam (e.g., a portion of the limb support device 100), δ is the amount of deflection, E is flexural modulus (or modulus of elasticity), and I is moment of inertia. By equating the amount of force applied, the material used, and the length of beam, a ratio between the amount of deflection with the fin 110 and without the fin 110 can be calculated by using the equation shown below.

$$\text{ratio} = I_{fin\ beam} / I_{rectangular\ beam}$$

where $I_{fin\ beam}$ is moment of inertia of the limb support device 100 with the fin 110 and $I_{rectangular\ beam}$ is moment of inertia of the limb support device 100 without the fin 110.

Using the example dimensions shown in FIG. 6A, the ratio between the amount of deflection with the fin 110 and without the fin 110 is about 1.26, which indicates that the limb support device 100 with the fin 110 is approximately 26% stiffer than the limb support device 100 without the fin 110.

In some implementations, adding the fin 110 to the limb support device 100 (e.g., a prosthetic foot or a crutch) can advantageously achieve the same level of stiffness for the limb support device 100 using less material. To achieve the same level of stiffness, the amount of deflection for the limb support device 100 with the fin 110 and the limb support device 100 without the fin 110 can be equated. Using the single load cantilever beam deflection formula described herein, the deflections of the limb support device 100 with the fin 110 and the limb support device 100 without the fin 110 can be calculated with following equations:

$$\delta_{fin} = FL/3EI_{fin}$$

$$\delta_{rectangular\ beam} = FL/3EI_{rectangular\ beam}$$

When the amount of deflections are the same (that is, the same level of stiffness) between the limb support device 100 with fin 110 and the limb support device 100 without the fin 110, the two equations above can be combined into the following.

$$FL/3EI_{fin} = FL/3EI_{rectangular\ beam}$$

Assuming that the amount of force applied, the material used, and the length of beam are the same between the limb support device 100 with fin 110 and the limb support device 100 without the fin 110, the above equation becomes:

$$I_{fin} = I_{rectangular\ beam}$$

This indicates that the level of stiffness with the fin 110 and without the fin 110 is the same when the moment of inertia for the cross-sectional shapes of the limb support device 100 with the fin 110 and the limb support device 100 without the fin 110 are the same. FIG. 6B shows example cross-sectional dimensions of the limb support device 100 with the fin 110 and the limb support device 100 without the fin 110 having the same moment of inertia. Calculating the cross-sectional areas of the two, the cross-sectional area of the limb support device 100 with the fin 110 is 8% less than that of the limb support device 100 without the fin 110. Assuming that the lengths of the limb support device 100 with the fin 110 and the limb support device 100 without the fin 110 are the same and that both are made from the same material, the limb support device 100 with the fin 110 can achieve the same level of stiffness with 8% less material used.

Although FIGS. 6A and 6B show cross-sectional dimensions of the limb support device 100, those dimensions are examples only. It is contemplated that different cross-sectional dimensions may be used for the limb support device 100.

Figure 6C:
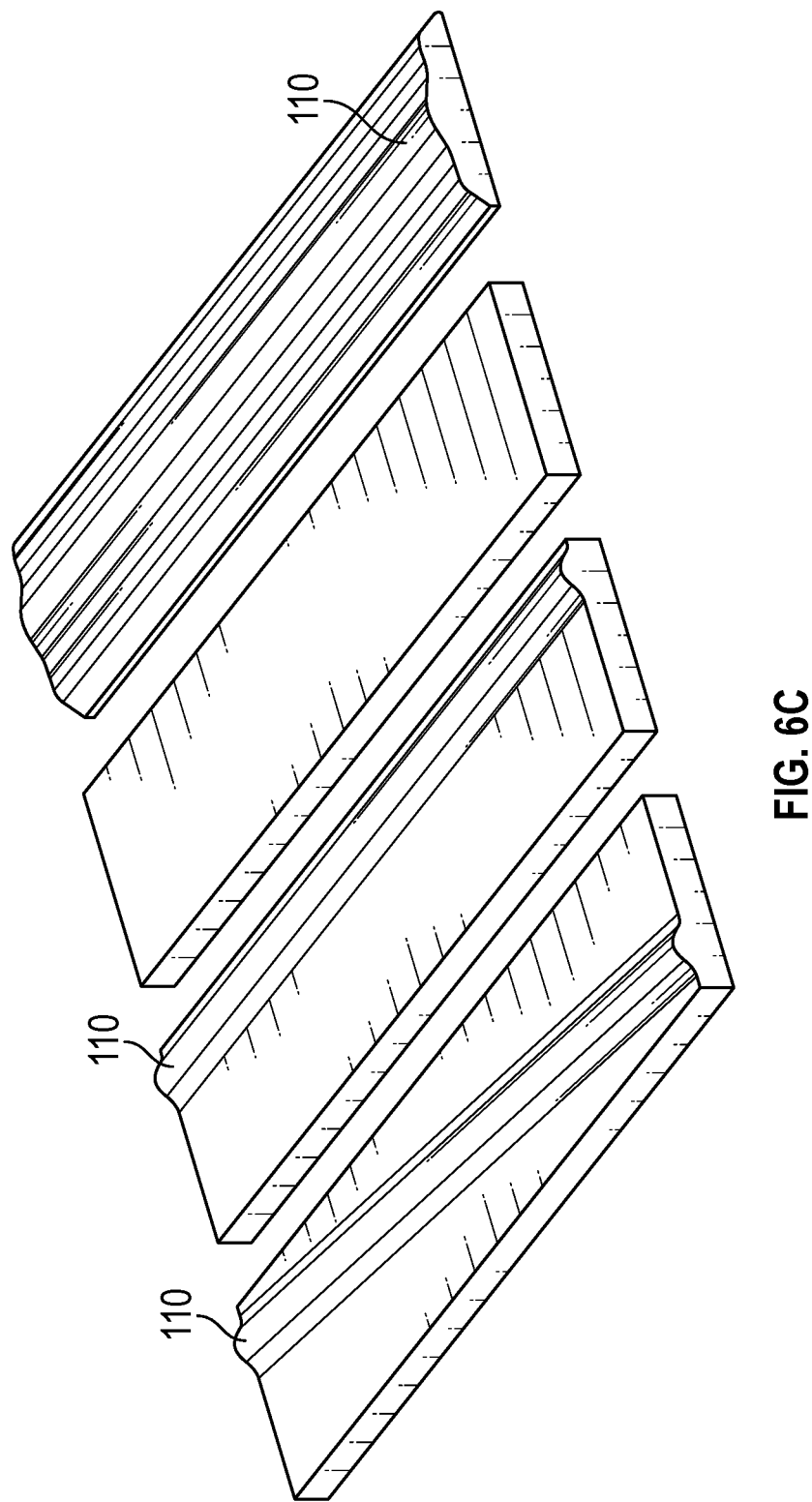
FIG. 6C illustrates various example configurations of a limb support device with and without a fin.

FIG. 6C illustrates some example configurations of the fin 110 for the limb support device 100. As described herein and shown in FIG. 6C, the fin 110 can have various different configurations, dimensions, or positions. In some examples, the fin 110 can diagonally extend along the length, or a portion of the length, of the limb support device 100 from a first side (e.g., medial side of the limb support device 100) to a second side (e.g., lateral side of the limb support device 100), or from the second side to the first side. In another example, the fin 110 may extend along only the first side (e.g., medial side of the limb support device 100) but not the second side (e.g., lateral side of the limb support device 100), or only the second side and not the first side.

Although the example calculations described herein used the fin 110 with substantially triangular cross-sectional shape, other cross-sectional shapes of the fin 110 can be used. Additionally and/or alternatively, the limb support device 100 may include more than one fins 110 (e.g., two fins, three fins) to, for example, increase its stiffness. In addition, different designs of the cross-section of the limb support device 100 can also change the stiffness of the prosthetic device 110.

In some implementations, the fin 110 can include at least a portion of fibrous material within the limb support device 100. This can advantageously increase stiffness of the fin 110 and may allow the fin 110 to withstand greater amount of bending or stress during use. A mold for the limb support device 100 can include a cavity that corresponds to the fin 110. When layers of fibrous material is added and cured (e.g., heat and pressure is applied), the layers can flow into and fill the cavity to form the fin 110.

In some implementations, the limb support device 100 can include the fin 110 in certain areas that can benefit from increased stiffness. For example, a portion of a prosthetic device may be reinforced by changing the cross-sectional shape, dimension, or both of the prosthetic device in that area. For example, the fins 110 can be positioned at areas or portions of the limb support device 100 where there is a change in thickness or an angled portion.

In some implementations, a customized degree of stiffness may be achieved by using customized cross-sectional shape, dimension, or both. Depending on the use of a prosthetic device (e.g., sports, leisure, or every-day use), varying level of stiffness and flexibility may be achieved using different cross-sectional shapes, dimensions, or both, and/or having, for example, the fin 110 at different locations.

In some implementations, the fin 110 may or may not extend along centerline the limb support device 100. The fin 110 can extend along an axis that is not parallel to the centerline of the limb support device 100. The fin 110 may extend at an angle with respect to the centerline of the limb support device 100. In some examples, the angle between the fin 110 and the centerline of the limb support device 100 may vary. In another example, the fin 110 may extend along an axis that is parallel to and offset from the centerline of the limb support device 100.

In some implementations, the height of the fin 110 may or may not remain constant. As such the height of the fin 110 may vary at certain portions or areas of the limb support device 100. For example, the height of the fin 110 may be increased at areas (e.g., an ankle portion of a limb support device) that experience more bending or stress during use. Such configuration can advantageously increase (or decrease) the level of stiffness of the limb support device 100 at those areas. Additionally, such configuration can reduce the amount of wear and tear during use.

In some implementations, the base width of the fin 110 may or may not remain constant. As such, the base width of the fin 110 may vary at certain portions or areas of the limb support device 100. This can advantageously increase (or decrease) the level of stiffness of the limb support device 100 at those areas.

In some implementations, the limb support device 100 can include more than one fin 110. The fins 110 may extend along the length of the limb support device 100 and be centered relative to the centerline (e.g., parallel to and equidistant from the centerline) of the limb support device 100. For example, the fins 110 may extend along axes that are parallel and offset (e.g., by equal amounts) relative to the centerline of the limb support device 100 (e.g., a blade portion or a foot portion of the limb support device 100). In another example, the fins 110 may extend along axes that are parallel and offset (but by unequal amounts) relative to the centerline of the limb support device 100. In another example, the fins 110 may extend along axes that are not parallel to the centerline of the limb support device 100.

The more than one fins 110 can have the same size, shape, and position with respect to the centerline of a limb support device such that the increase in stiffness of a limb support device corresponding to each of the fins 110 is even. This can advantageously cause the limb support device to experience even bending.

In some implementations, however, it may be advantageous for the limb support device to experience a certain amount of torsion during use. In order to generate torsion of the limb support device during use, the size, shape, and/or position of the fins 110 can be different. For example, a first fin may be further away from the centerline of the limb support device than a second fin. As such a portion (or area) of the limb support device around the first fin may be less stiff than a portion (or area) of the limb support device around the second fin. In some examples, one of the fins 110 may be bigger (e.g., wider, taller, or both) than the other. In another example, one of the fins 110 may have a different shape (e.g., semi-oval) than the other (e.g., generally triangular). The torsion generated at least in part by the differences between the fins 110 can be useful in applications in which a limb support device undergoes a certain base amount of torsion during use. As such, the fins 110 may be used to counter the base amount of torsion to, for example, reduce the amount of shear stress applied to the limb support device. The fins 110 can therefore be sized, shaped and/or positioned to advantageously generate torsion forces on the limb support device (e.g., crutch or prosthetic foot) that can aid or improve the rollover of the limb support device during ambulation of the user.

The fin 110 may affect response (e.g., deformation) of the limb support device 100 when a torsional moment is applied to the limb support device 100. The location of the fin 110 (e.g., extending only along the medial/lateral side, extending diagonally from the medial/lateral side to the lateral/medial side, and the like) can impact the trajectory and displacement of different portions of the limb support device 100 when the limb support device 100 experiences torsion (e.g., when a user of the limb support device 100 pivots). For example, when the fin 110 extends only along the medial side of the limb support device 100, the medial side of the limb support device 100 undergoes greater deformation (e.g., bends and/or rotates) more than when the fin 110 extends along the centerline of the limb support device 100. As such, various configuration of the fin 110 (or fins 110) may be used to change and control how the limb support device 100 reacts or deforms (e.g., rotation, bending, and the like) when torque is applied to the limb support device 100. For example, customized torsional response of the limb support device 100 can be used to guide the deformation of the limb support device 100 during ambulation by the user.

Figure 7A:
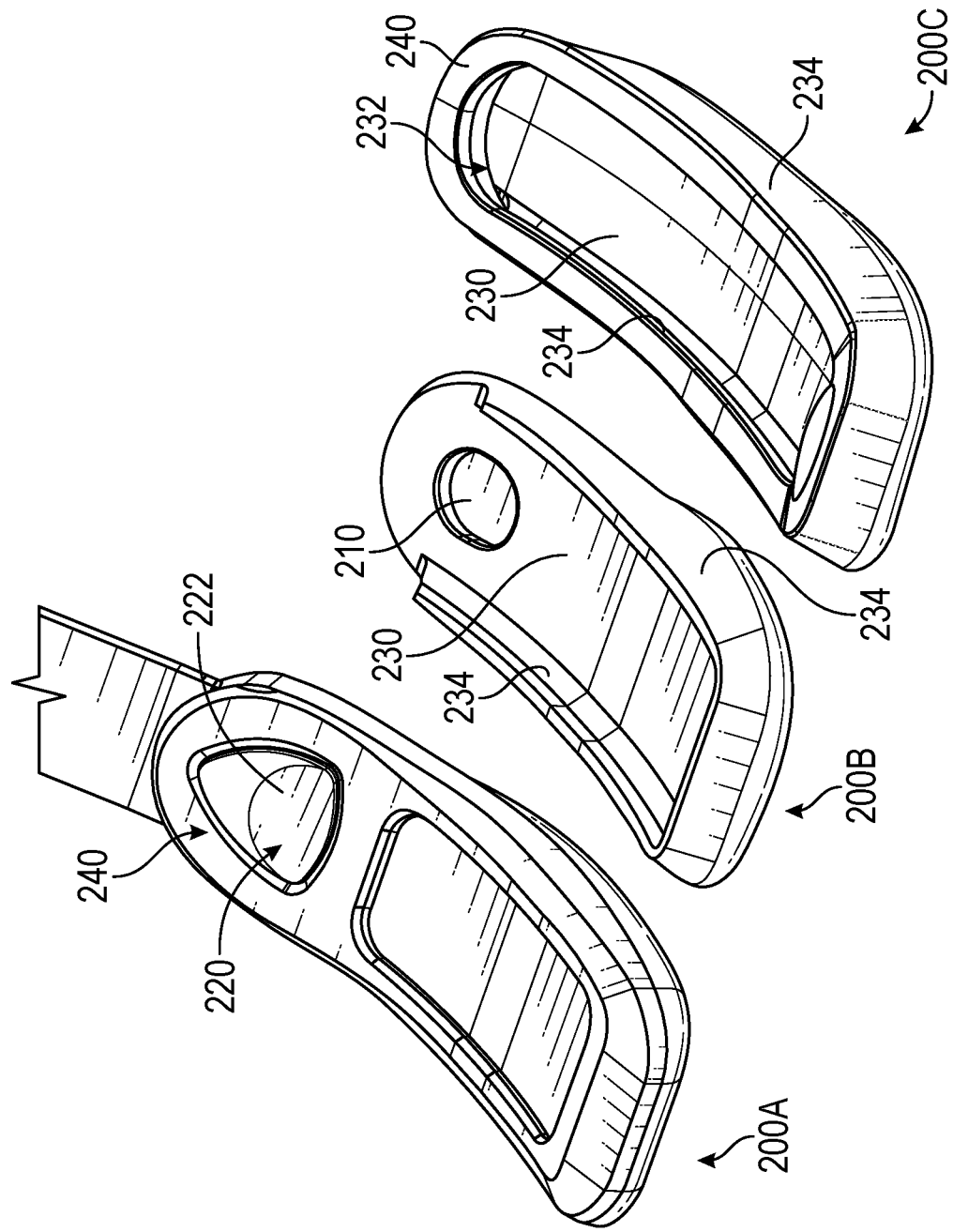
FIGS. 7A-7K show various views of example sole systems.
Figure 7B:
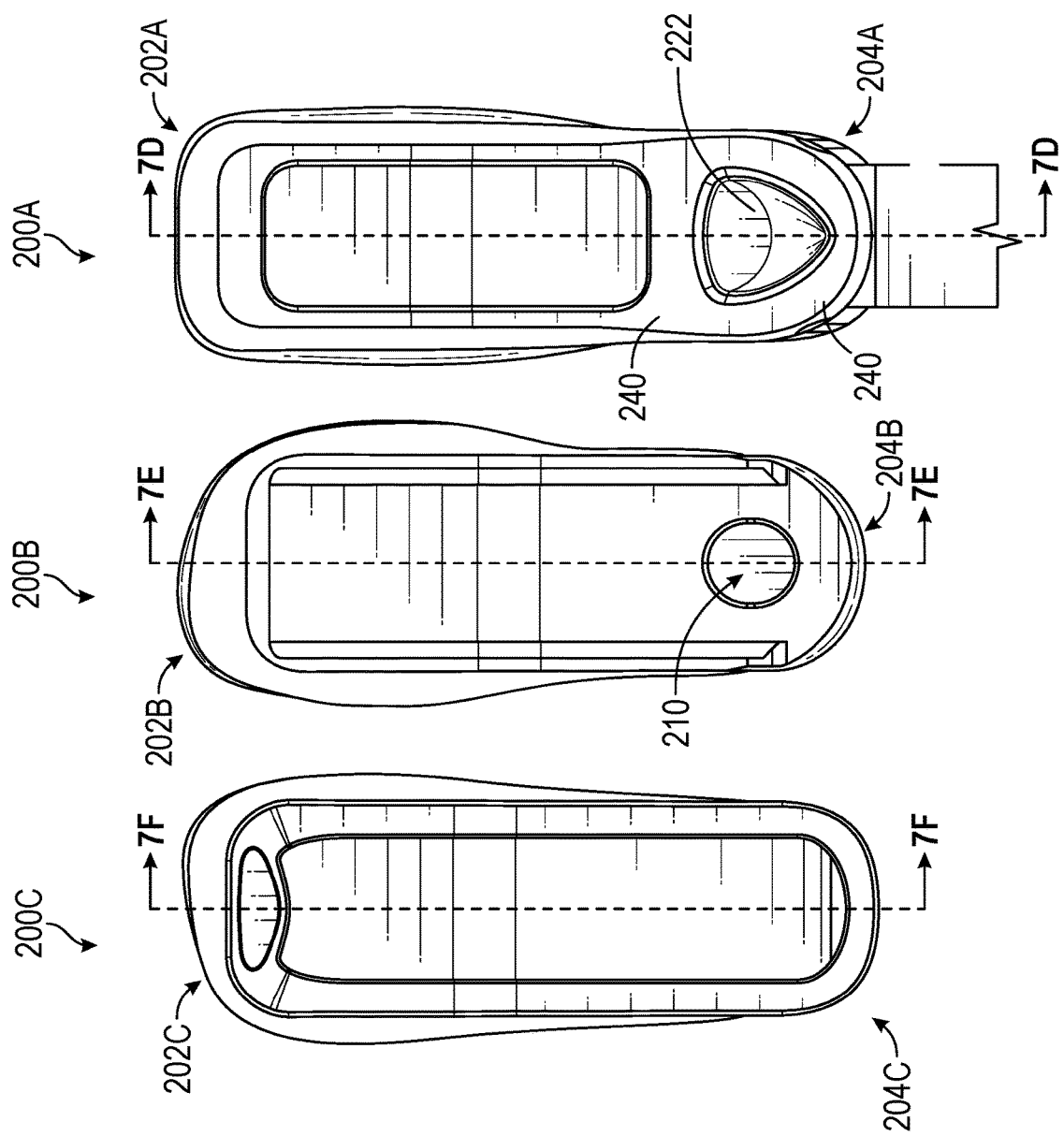
Figure 7C:
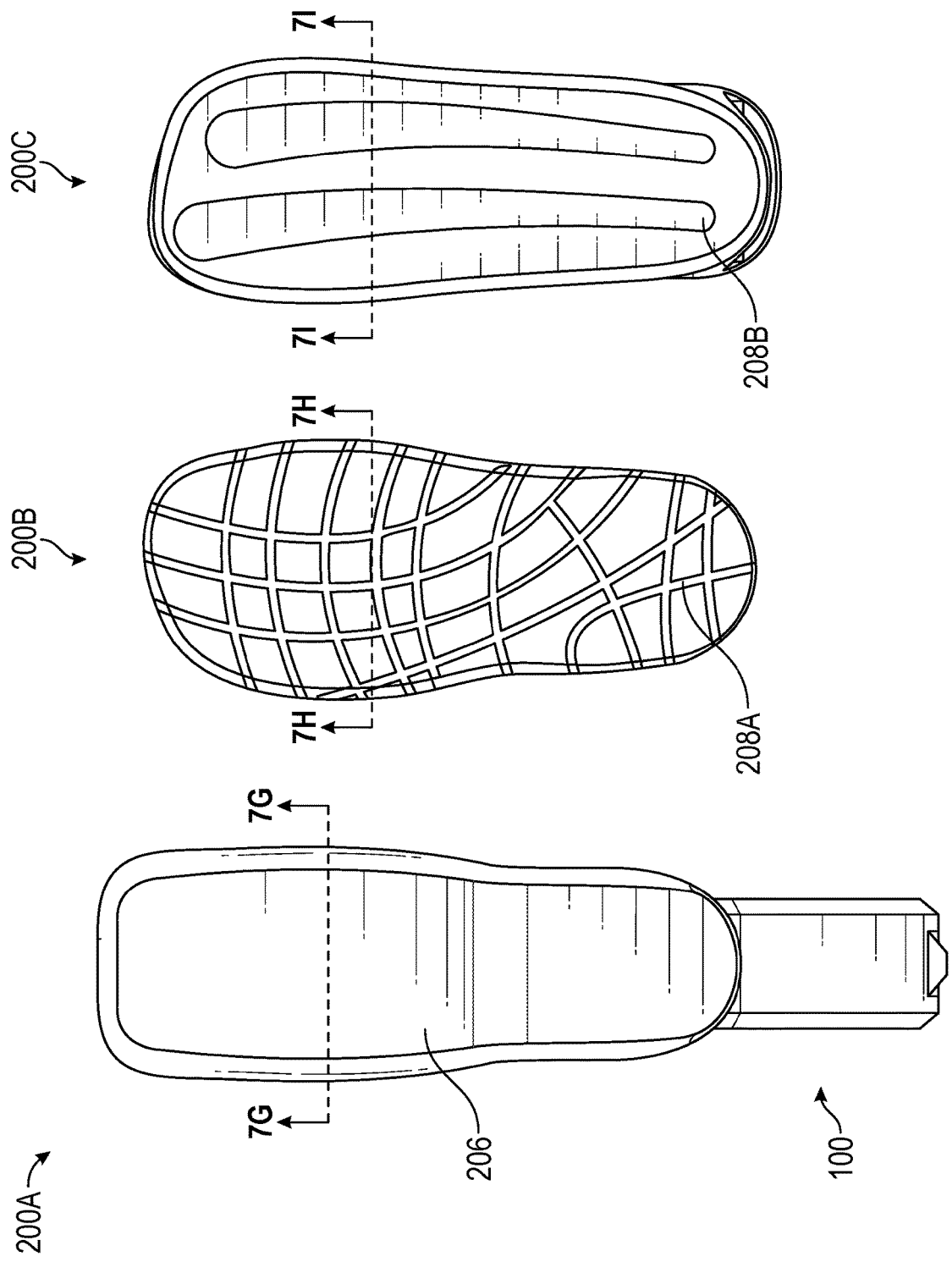
Figure 7D:
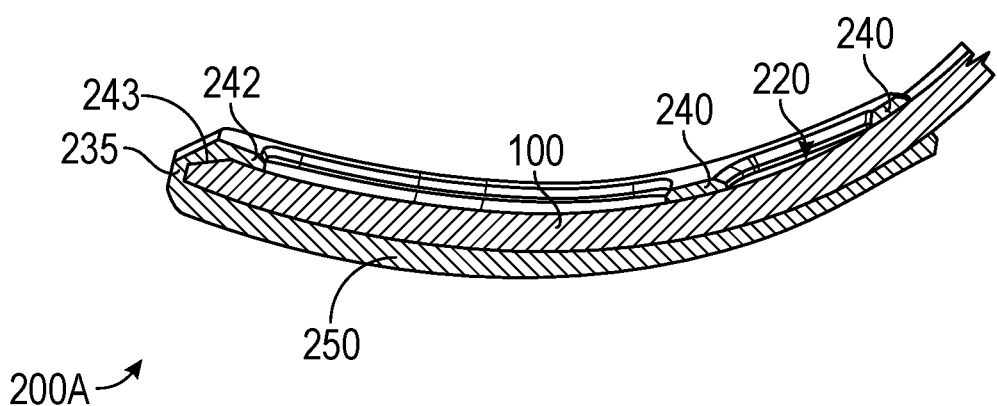
Figure 7E:
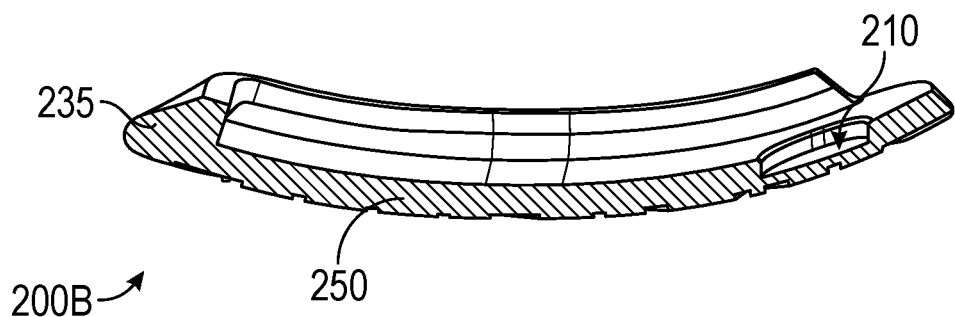
Figure 7F:
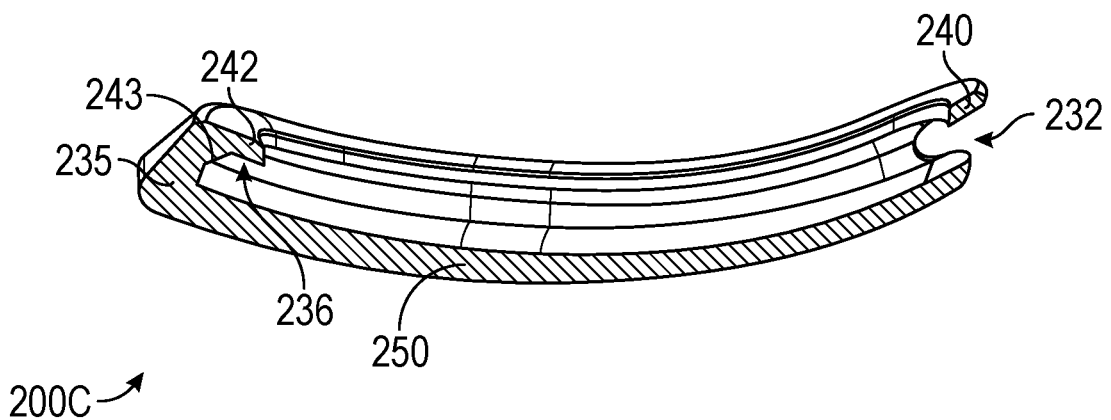
Figure 7G:
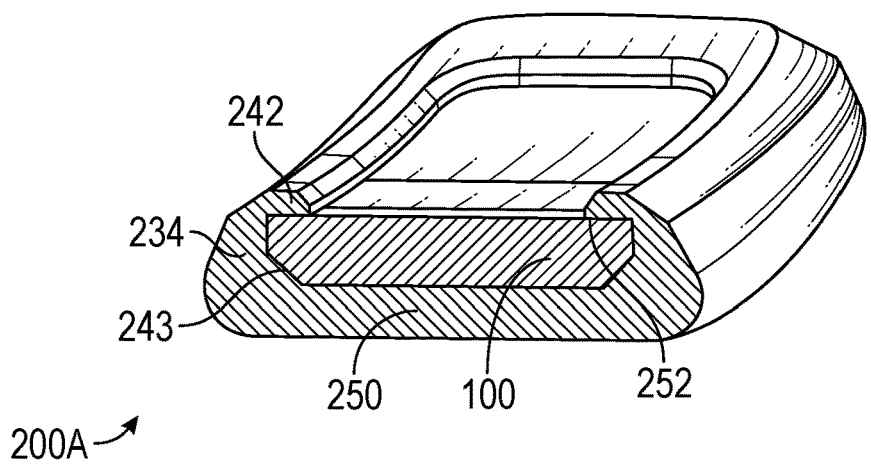
Figure 7H:
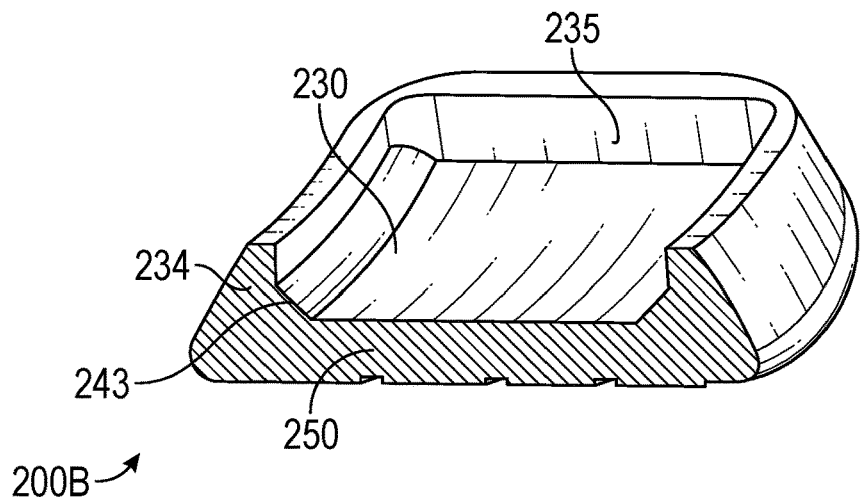
Figure 7I:
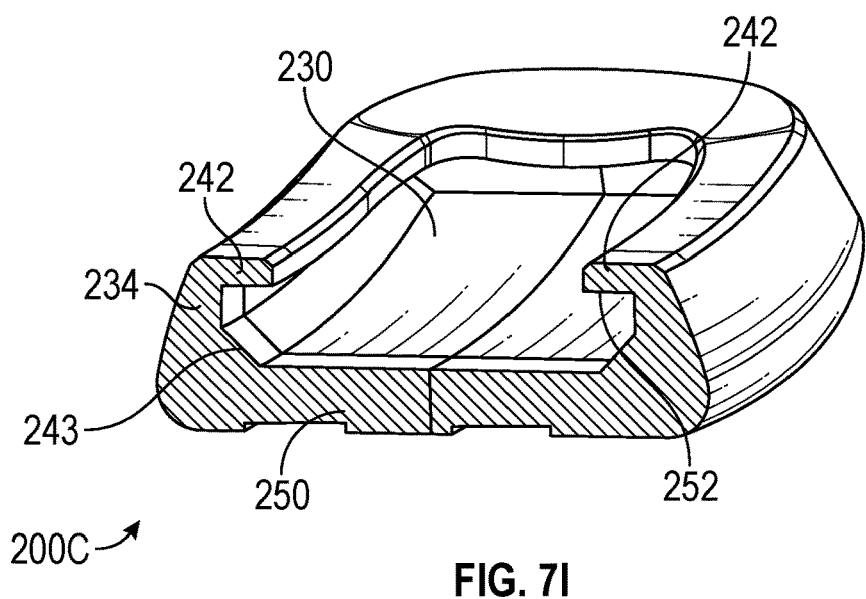
Figure 7J:
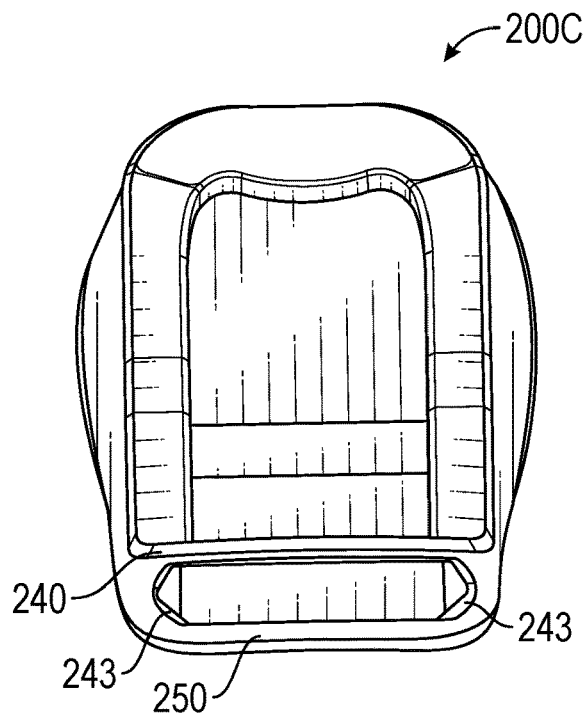
Figure 7K:
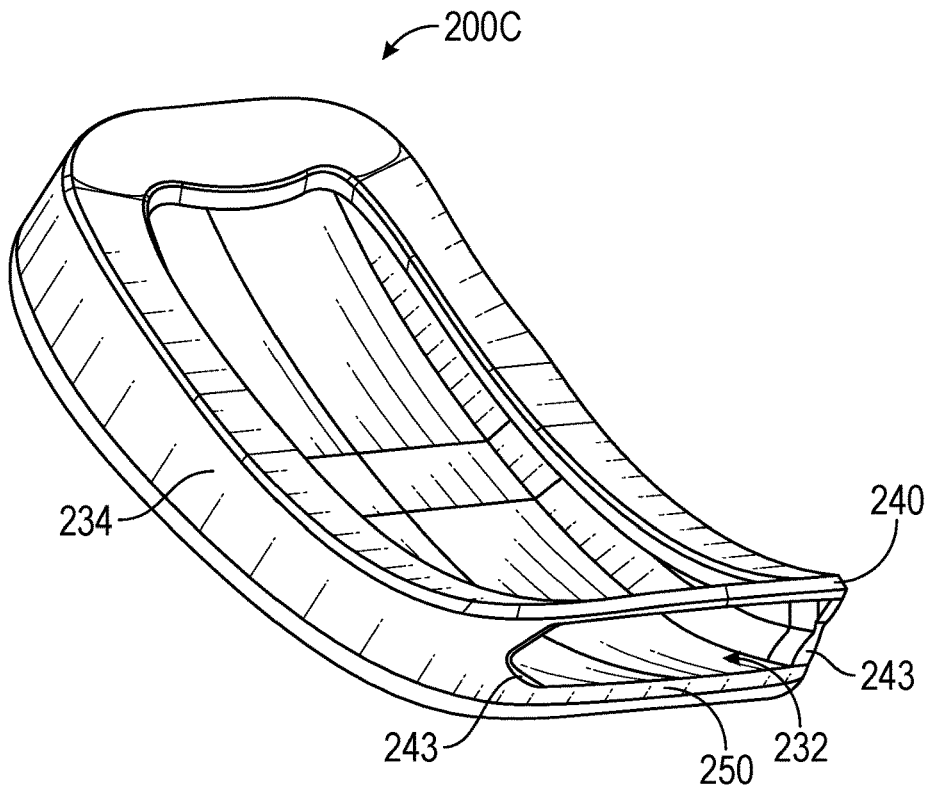
Figure 7L:
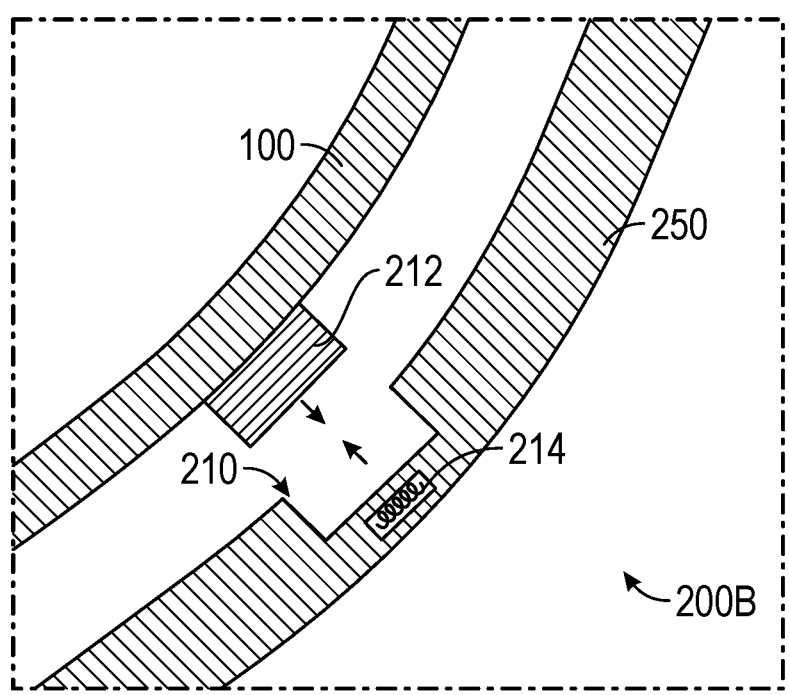
FIGS. 7L and 7M are schematic illustrations of an example coupling between a limb support device and an intermediate portion of a sole system.
Figure 7M:
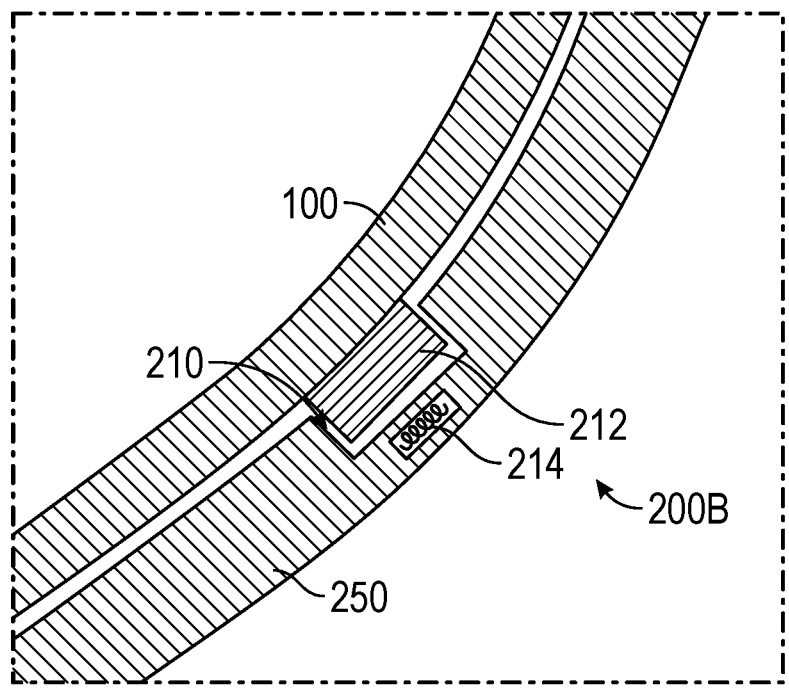
Figure 7N:
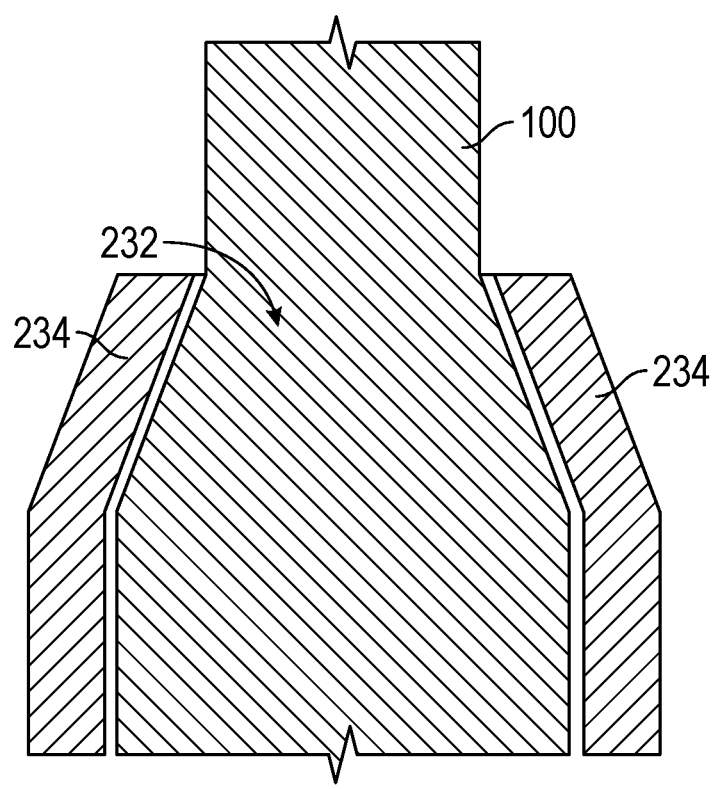
FIG. 7N is a schematic illustration of a tapering configuration of a slot of a sole system.

With reference to FIGS. 7A-7N, example soles 200A, 200B, 200C for a limb support device (e.g., the limb support device 100 of FIGS. 4A and 4C) are described herein. The soles 200A, 200B, 200C may be removable or fixed to the limb support device. The soles 200A, 200B, 200C might be universal or be designed to have a left/right profiles. The soles 200A, 200B, 200C can be made out of EVA, rubber, or other suitable materials (e.g., resilient materials, compressible materials). In some implementations, one or more materials may be used for manufacturing the soles 200A, 200B, 200C. As discussed above, the limb support device can be, for example, a crutch. In another example, the limb support device can be a prosthetic footplate.

The soles 200A, 200B, 200C can include distal ends 202A, 202B, 202C and proximal ends 204A, 204B, 204C respectively. The soles 200A, 200B, 200C can receive a distal portion of a limb support device via the proximal ends 204A, 204B, 204C and the limb support device can slide from the proximal ends 204A, 204B, 204C towards the distal ends 202A, 202B, 202C.

The soles 200A, 200B, 200C can include a bottom portion 250 that provides additional support (e.g., cushioning support) for the limb support device. The bottom portion 250 may be compressible such that it can, for example, reduce the amount of impact force transferred to the limb support device from the ground during use. The bottom portion 250 can include a support surface 206 that is an underside of the bottom portion 250. As shown in FIG. 7C, the support surface 206 can include traction marks 208A, 208B or any other types of traction marks suitable for different uses (e.g., hiking, climbing, running, walking, indoor, and the like), so that the soles 200A, 200B, 200C can provide traction to the limb support device.

The soles 200A, 200B, 200C can include one or more features that can prevent or reduce the likelihood of a limb support device (e.g., the limb support device 100 shown in FIGS. 4A and 4C) being separated (e.g., sliding out) from the soles 200A, 200B, 200C during use.

The bottom portion 250 of the soles 200A, 200B, 200C can include side edges 234 and a front edge 235. The side edges 234 can extend upwards (e.g., vertically) from medial and lateral sides of the bottom portion 250. The front edge 235 can extend upwards (e.g., vertically) from a distal end of the bottom portion 250. The front edge 235 can form the distal ends 202A, 202B, 202C of the soles 200A, 200B, 200C. During use, the side edges 234 can inhibit (e.g., prevent) limb support device from moving medially or laterally relative to the soles 200A, 200B, 200C, and thus retains the limb support device positioned between the side edges 234. The front edge 235 can inhibit (e.g., prevent) the limb support device from sliding further forward relative to the soles 200A, 200B, 200C.

In some implementations, the soles 200A, 200B, 200C can include a slot or recess 210. The slot 210 can be circular (as shown in, e.g., in FIGS. 7A and 7B), oval, rectangular, or any other suitable shape. The slot 210 may engage or interact with a corresponding protrusion 212 of a limb support device (e.g., the limb support device 100). FIGS. 7L and 7M illustrate an interaction between the slot 210 and the corresponding protrusion 212.

In some implementations, the slot 210 can include a magnet 214 or any magnetic material (e.g., iron) at its bottom. Additionally and/or alternatively, the magnet 214 can be positioned below the bottom surface of the slot 210. A limb support device (e.g., the limb support device 100) can include a corresponding protrusion 212 that can mate with the slot 210. In some examples, the corresponding protrusion 212 can be positioned at the back of the limb support device, either by gluing it on or by forming it integrally with a mold. The corresponding protrusion 212 can include a magnet or any magnetic material (e.g., iron) that, when the corresponding protrusion 212 is inserted within the slot 210, can magnetically interact with or engage the magnet or magnetic material 214 of the slot 210, so that a magnetic force (e.g., attractive force) between the protrusion 212 and the slot 210 at least partially couples the soles 200A, 200B, 200C and the limb support device together. Alternatively, the prosthetic device can instead include the slot 210 and the soles 200A, 200B, 200C can include the corresponding protrusion 212.

The positions of the slot 210 and the corresponding protrusion 212 may be offset (e.g., along the centerline of the limb support device 100) from one another such that the soles 200A, 200B, 200C need to be pulled (e.g., stretched) towards the ankle portion of the limb support device (e.g., the ankle portion 140 of the limb support device 100 as shown in FIG. 4A) in order for the protrusion 212 to be inserted into the slot 210. As such, both the magnetic force between the magnet 214 and the protrusion 212 and mechanical interaction between the slot 210 and the protrusion 212 (e.g., caused by retracting force of the soles 200A, 200B, 200C) can help maintain coupling between the soles 200A, 200B, 200C and the limb support device 100.

Additionally or alternatively (e.g., when the protrusion 212 and slot 210 do not have magnets or magnetic material), the interaction between the slot 210 and the corresponding protrusion 212 of the prosthetic device can generate a mechanical lock between the soles 200A, 200B, 200C and the prosthetic device. For example, when the corresponding protrusion 212 is at least partially inserted within the slot 210, the circumferential edge of the protrusion 212 can abut the inner edges of the slot 210. The abutment between the circumferential edge of the protrusion 212 and the inner edges of the slot 210 can inhibit (e.g., prevent) the protrusion 212 from sliding out from the slot 210.

The proximal ends 204A, 204C of the soles 200A, 200C can include a slit 232 through which an end of the limb support device (e.g., distal end of crutch, prosthetic footplate) can be extended. FIGS. 7J and 7K show the sole 200C with an example slit 232. The slit 232 can include chamfered edges 243 that corresponds to chamfered edges of the sides of a limb support device, for example. The slit 232 can be formed between the bottom portion 250, a cover 240, and slide edges 234 as shown in FIG. 7K.

In some implementations, the opening associated with the slit 232 can be tapered. FIG. 7N shows an example cross-section of the slit 232. The inner surface of the side edges 234 may taper so as to correspond to the tapering width of the limb support device 100. For example, as shown in FIG. 7N, a proximal opening of the slit 232 (that is, an opening further away from the front edge 235) can have a first width and a distal opening (that is, an opening close to the front edge 235) of the slit 232 can have a second width, where the second width of the slit 232 is greater than the first width of the slit 232. For a limb support device having a foot portion (or a blade portion) wider than, for example, an ankle or a calf portion, such configuration of the slit 232 (e.g., tapering width) can inhibit (e.g., prevent) the foot portion (or the blade portion) from sliding out from, for example, the sole 200C, through the slit 232. Since the foot portion is wider than the proximal opening of the slit 232, the width of the proximal opening can help secure the foot portion of the limb support device in the sole 200C.

As discussed herein, the soles 200A, 200B, 200C can include side edges 234 that can extend (e.g., vertically) upwards from the bottom portion 250. Together with a support surface 230 (that is, a top surface of the bottom portion 250), the side edges 234 can receive a foot portion of a limb support device (e.g., crutch, prosthetic footplate). While the support surface 230 can support the bottom of the foot portion, the side edges 234 can provide medial-lateral support and inhibit (e.g., prevent) lateral displacement of the limb support device within the soles 200A, 200B, 200C. In some implementations, the side edges 234 can include a chamfered edge 243 that correspond to chamfered edges of the limb support device. For example, FIG. 7G shows the chamfered edges 243 of the side edges 234 of the sole 200A abutting chamfered edges of an example limb support device. In some implementations, as shown in FIG. 7G, the chamfered edge 243 can be located proximate to the support surface 230 (e.g., located between the bottom portion 250 and the side edges 234). Additionally or alternatively, the chamfered edge 243 can be located opposite from the support surface 230 (e.g., located between the lip 242 and the side edge 234).

Additionally, the side edges 234 can include lips 242 that can extend from the top of the side edges 234 towards the middle of the soles 200A, 200B, 200C. As shown in FIG. 7I, the bottom surface of the lips 242 can, when a limb support device is slid into the soles 200A, 200B, 200C, and rest against a top surface of the limb support device.

The corresponding shapes (or contours) of the side edges 234 (e.g., including the chamfered edges 243 and the lips 242) of the soles 200A, 200B, 200C and chamfered edges of a limb support device can retain the limb support device within the soles 200A, 200B, 200C between the side edges 234. As such, the soles 200A, 200B, 200C can function as a sleeve into which a prosthetic device can be slid into.

With reference to FIG. 7A, in some implementations, the soles 200A, 200B, 200C can include an opening 220 that can receive a button 222 attached to a limb support device (e.g., the limb support device 100 shown in FIGS. 4A and 4C). The opening 220 can be formed on a top portion (e.g., the cover 240) or a bottom portion (e.g., the bottom portion 250) of the soles 200A, 200B, 200C. In the example shown in FIG. 7A, the opening 220 is formed on the top portion of the sole 200A such that the button 222 is attached or formed on a top surface of a limb support device. The opening 220 can be formed on the cover 240 positioned near the proximal end 204A, 204B, 204C. In some examples, the opening 220 is formed on the bottom portion 250 of the 200A, 200B, 200C such that the button 222 is attached or formed on a bottom surface (e.g., bottom or rear facing surface) of a limb support device.

The shape of the opening 220 can correspond to the shape of the button 222 such that the opening 220 can receive the button 222. When the opening 220 receives the button 222, the interaction (e.g., coupling) between the button 222 and the opening 220 can aid in inhibiting (e.g., preventing) the limb support device from being dislodged (e.g., slipping off) from the soles 200A, 200B, 200C. As the limb support device with the button 222 is inserted into the soles 200A, 200B, 200C, the cover 240 may slide over the button 222. Once the limb support device is fully inserted into the soles 200A, 200B, 200C, at least a part of the cover 240 may extend adjacent a proximal side (that is, side that is closer to the proximal end of the sole) of the button 222. In some examples, as shown with the sole 200C in FIG. 7B, the cover 240 may extend adjacent both a proximal side and a distal side (that is, side that is closer to the distal end of the sole). In some example, the cover 240 may surround the entire outer surface of the button 222.

The front edge 235 of the soles 200A, 200B, 200C can also include the lip 242. As shown in, for example, FIGS. 7D and 7F, the lip 242 can extend from the front edge 235 towards the proximal ends 204A, 204B, 204C. The lip 242, the front edge 235, and the bottom portion 250 can together define a cavity 236. The cavity 236 can be dimensioned to receive a front end of a limb support device (e.g., the limb support device 100 as shown in FIG. 4A). The lip 242 and the front edge 235 can form the chamfered edge 243. The chamfered edge 243 can, as described herein, help with retaining the front edge of a limb support device (e.g., the limb support device 100 shown in FIGS. 4A and 4C). The lip 242 can include an engagement surface 252 that can (e.g., when a limb support device is inserted into the sole 200A, 200B, 200C) engage a top surface of the limb support device. As shown in, for example, in FIG. 7G, the engagement surface 252 of the lip 242 can be positioned opposite of the bottom portion 250 and engage (e.g., rest against or abut) the top surface of the limb support device during use.

In some implementations, as shown in FIG. 7H, the side edges 234 and/or the front edge 235 may not include the lip 242.

With reference to FIGS. 8A-9B, an example sole system 300 for a limb support device and its various features are described herein. The sole system 300 can include an intermediate piece 304 and a sole body 302. The sole body 302 includes a support surface 308 that can be dimensioned to receive the intermediate piece 304. The intermediate piece 304 can include a support surface 310 that can be dimensioned to receive at least a portion of a limb support device, such as the limb support device 100.

The removable sole 300 can include a clamp 306 that can attach the intermediate device 304 to the limb support device 100. The clamp 306 can include arms 316 that can wrap around both the intermediate device 304 and the limb support device 100. The arms 316 can include openings 314 that can receive a screw that can be tightened bring the arms 316 towards each other, thereby securing the limb support device 100 to the intermediate piece 304, or vice versa. Other methods may be used to bring and/or retain the arms 316 towards each other.

As shown in FIGS. 8A-8D, the clamp 306 may wrap around both the intermediate piece 304 and the limb support device 100 at a portion where both the intermediate piece 304 and the limb support device 100 tapers (e.g., the width decreases). In some implementations, at least a portion of the arms 316 may be angled to accommodate the tapering width of both the intermediate piece 304 and the limb support device 100. Such feature of the clamp 306 (e.g., angled arms 316) can prevent, for example, a foot portion, of the limb support device 100 (that is a portion of the limb support device 100 below the clamp 306) from sliding up towards the clamp 306 and dislodged from the intermediate piece 304.

Figure 8A:
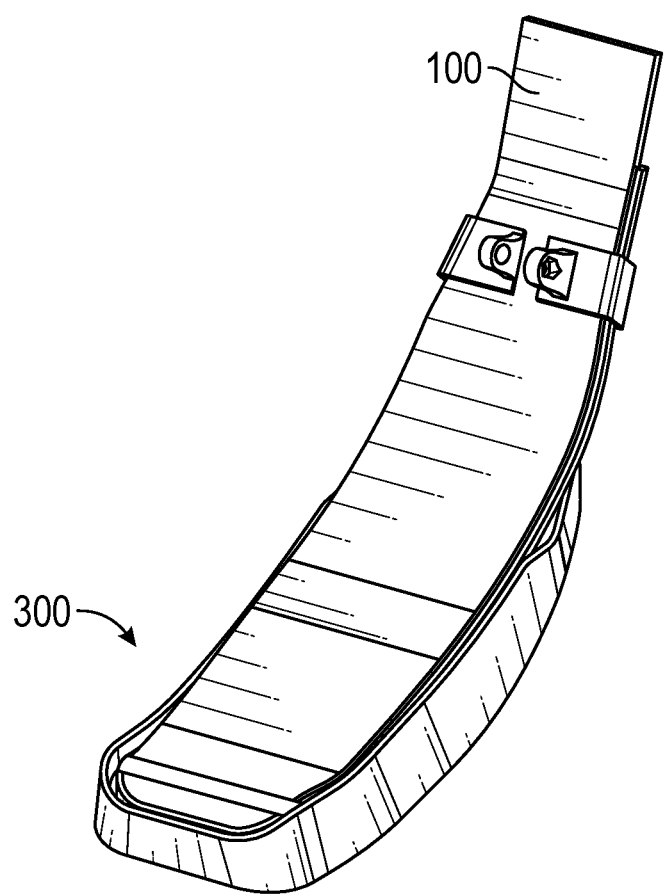
FIGS. 8A-8I show various views of another example sole system.
Figure 8B:
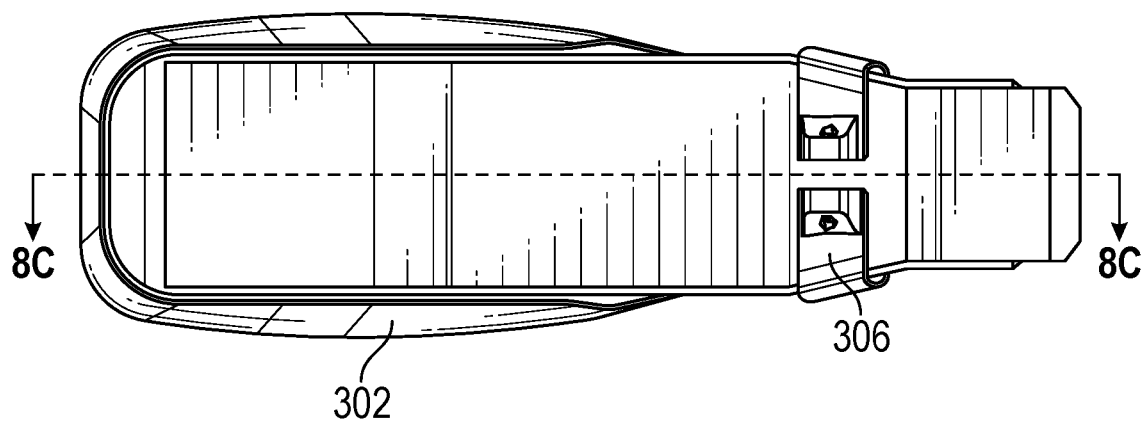
Figure 8C:
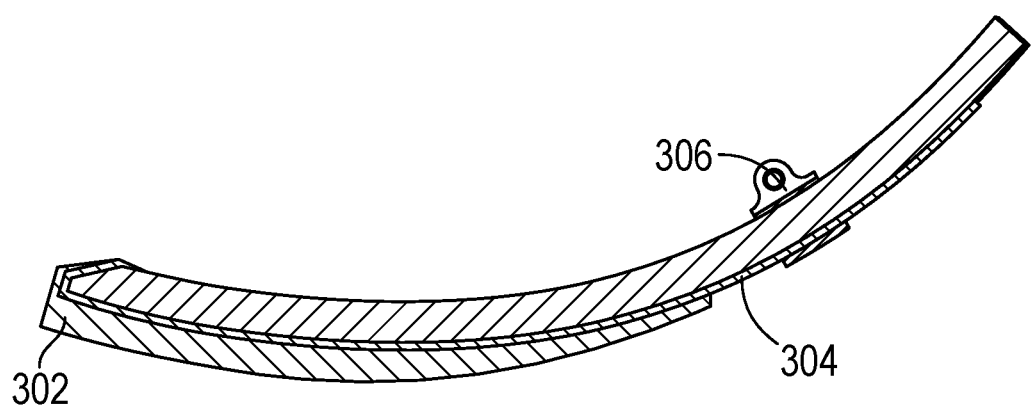
Figure 8D:
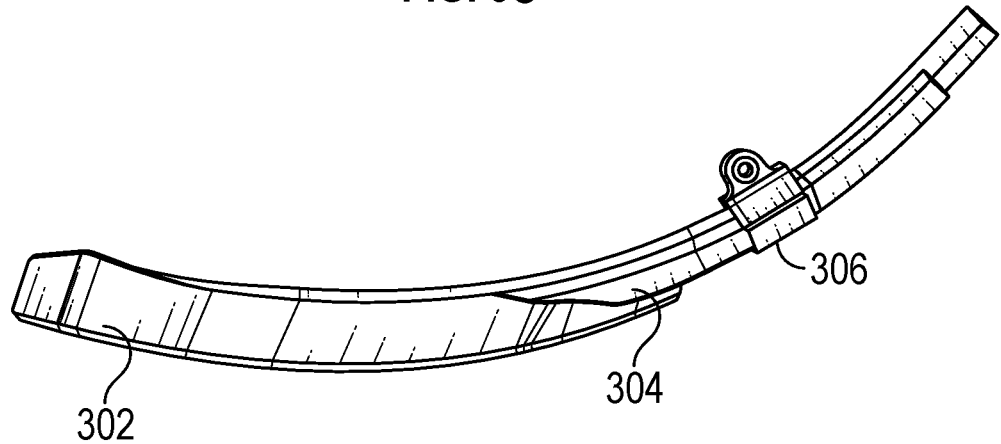
Figure 8E:
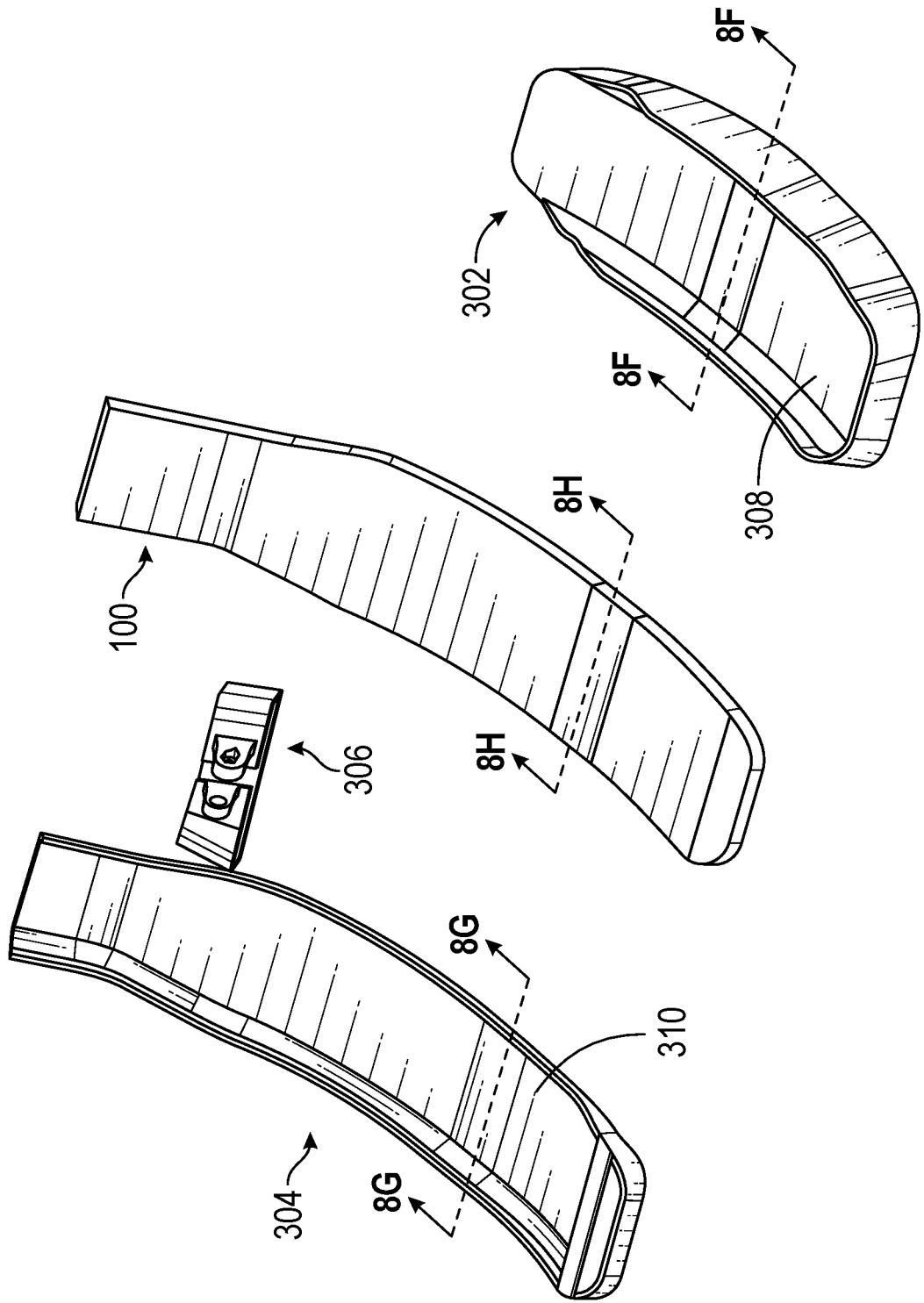
Figure 8F:
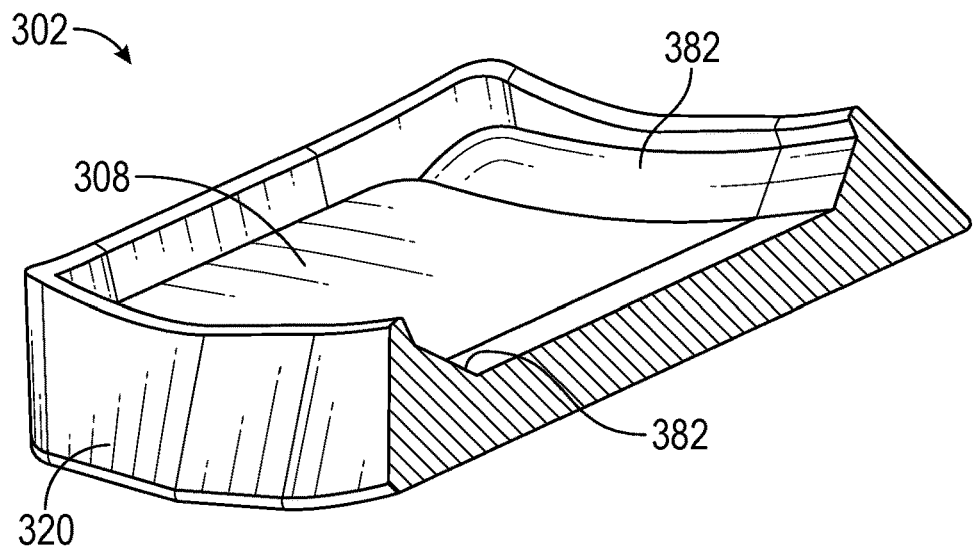
Figure 8G:
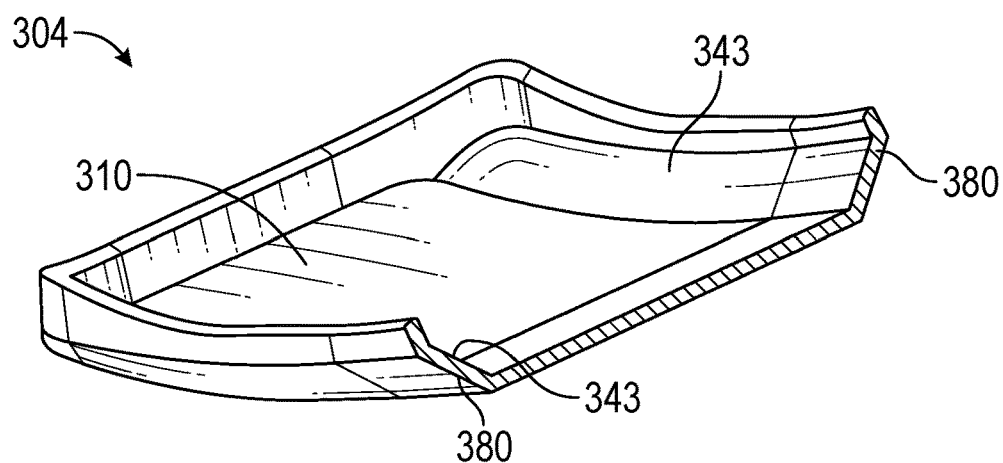
Figure 8H:
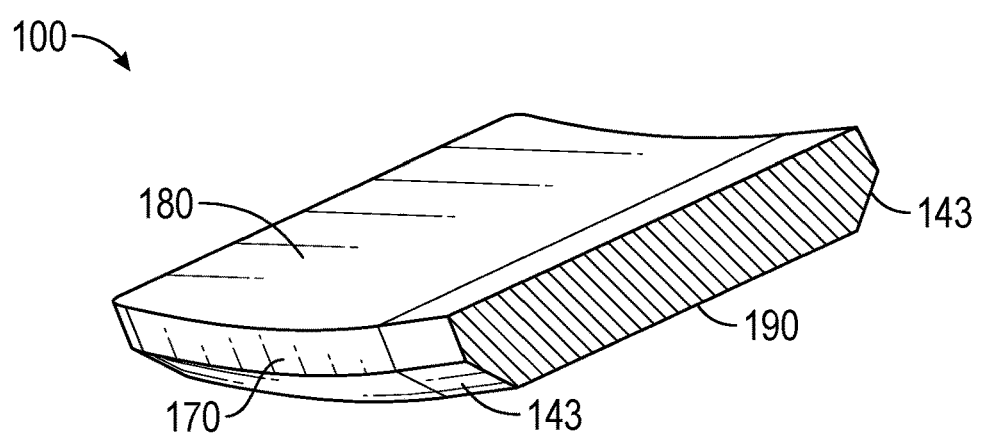
Figure 8I:
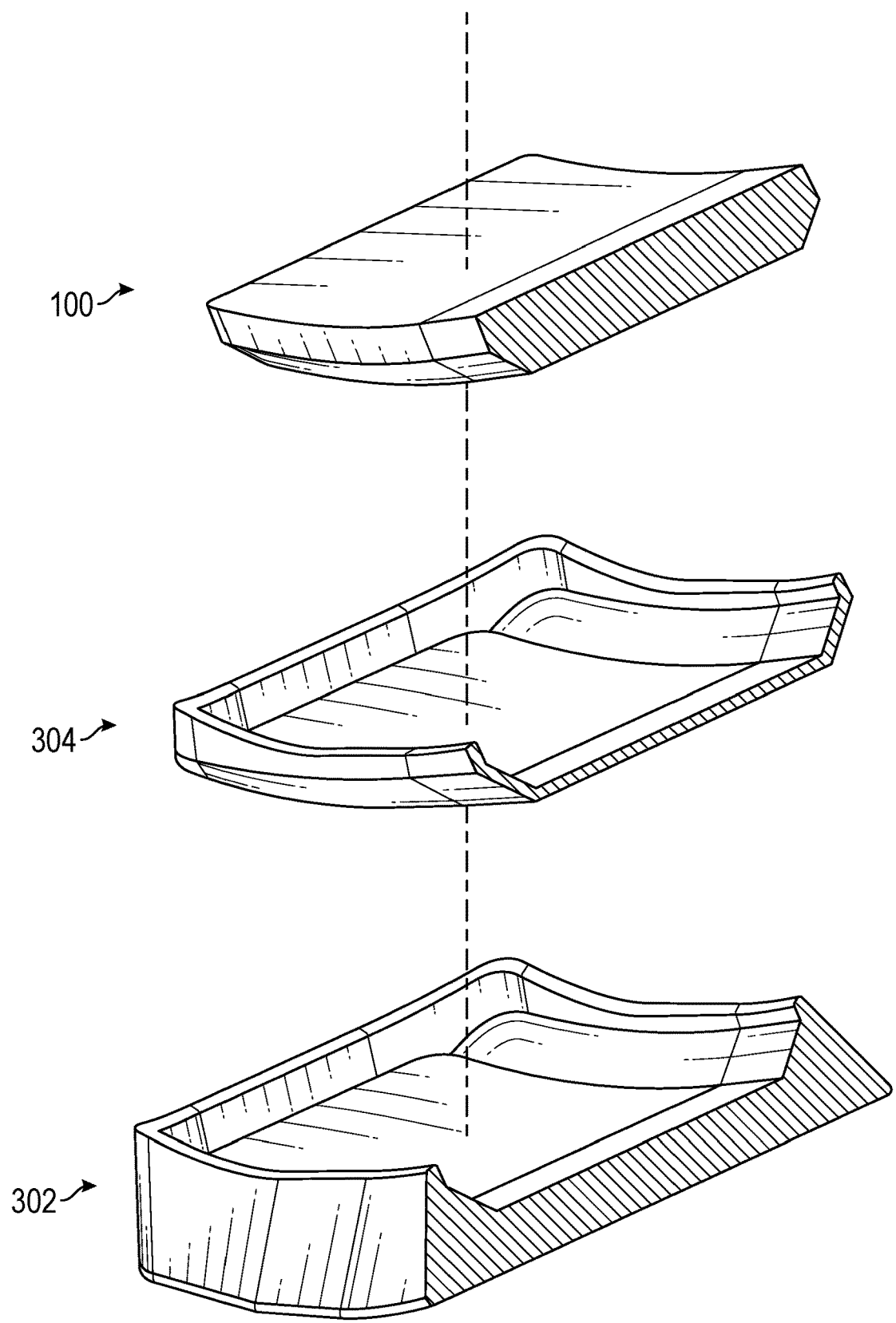
Figure 9A:
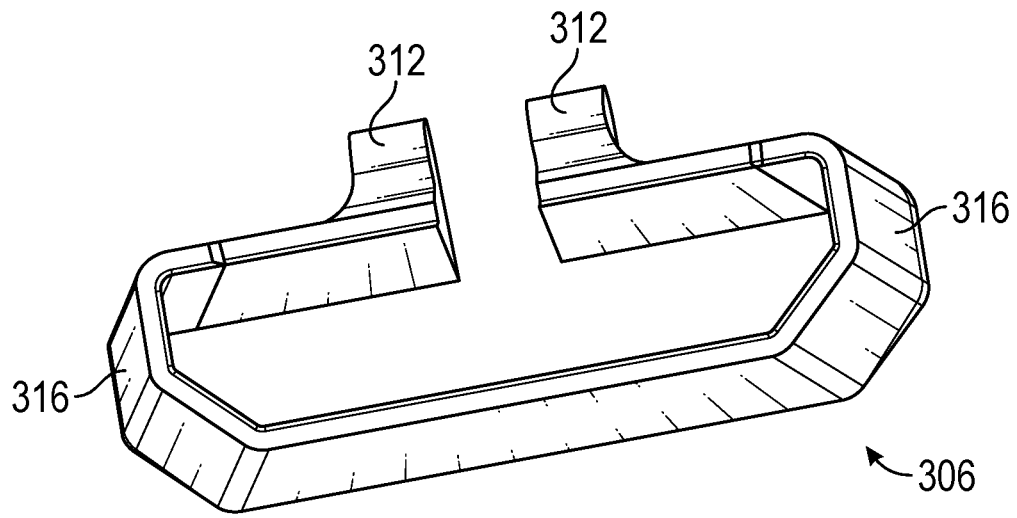
FIGS. 9A and 9B show a clamp for the sole system of FIGS. 8A-8H.
Figure 9B:
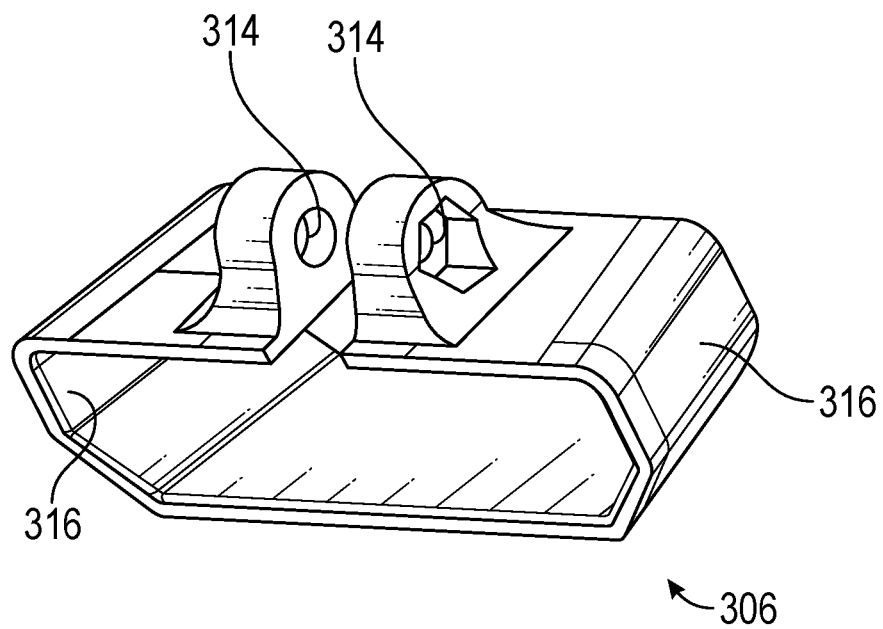

FIG. 8E shows the sole body 302, the intermediate piece 304, and the limb support device 100 detached from each other. FIGS. 8F-8H show cross-section views of the sole body 302, the intermediate piece 304, and the limb support device 100. The limb support device 100 can include a blade portion (or a foot portion) that includes side surface 170, a top surface 180, and a bottom surface 190. In some implementations, the limb support device 100 can include chamfered portion between the side surfaces 170 and the bottom surface 190.

As shown in FIG. 8G, the intermediate portion 304 can include a first chamfered surface 343 that corresponds to the chamfered portion 143 of the limb support device 100. The chamfered surface 343 can be disposed between side edges and the support surface 310. The chamfered surface 343 can be dimensioned to abut the chamfered portion 143 of the limb support device 100 to prevent or reduce the likelihood of the limb support device 100 slipping out of the intermediate portion 304. In some implementations, the intermediate portion 304 can include a second chamfered surface 380.

The intermediate portion 304 can be coupled to the sole body 302. In some example, the intermediate portion 304 may be adhered to the sole body 302 using adhesives. In another example, the intermediate portion 304 may be coupled to the sole body 302 using various types of fastening mechanisms including, but not limited to, press fit connection, screws, nuts and bolts, clasps, pins, rivets, snap-fit connection, and the like. In some implementations, the intermediate portion 304 may be permanently or removably coupled to the sole body 302.

The sole body 302 can include side edges 320 and the support surface 308. In some implementations, the sole body 302 can include chamfered surface 382 that can correspond to the second chamfered surface 380 of the intermediate portion 304.

Figure 10A:
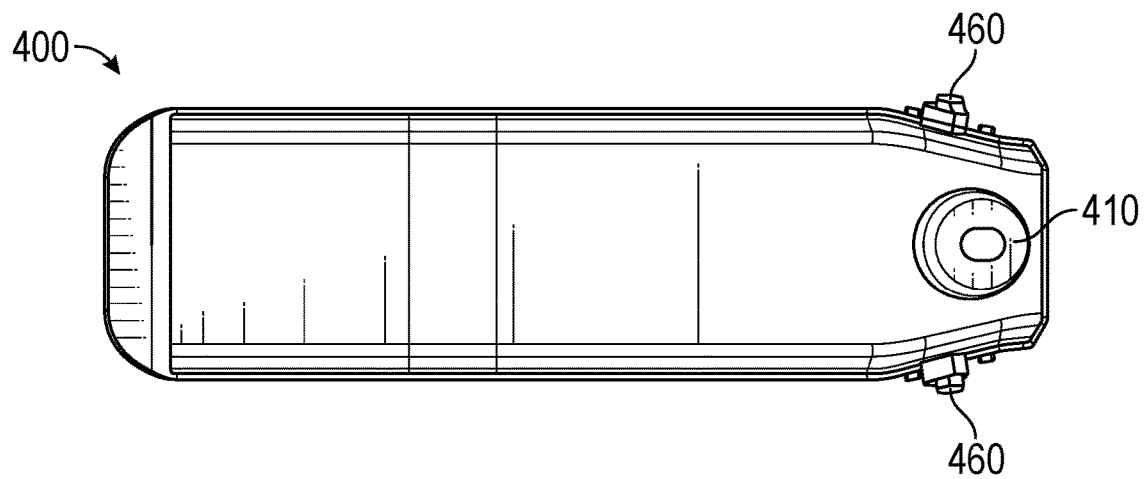
FIGS. 10A-10C show various view of an example intermediate portion of a sole system.
Figure 10B:
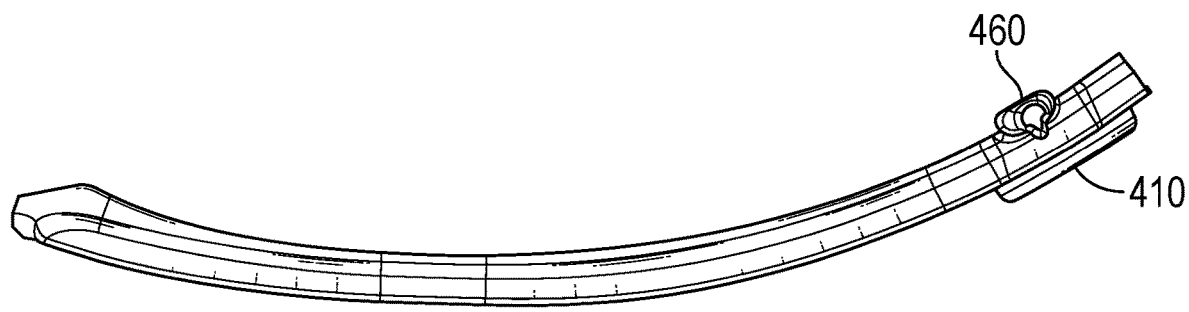
Figure 10C:
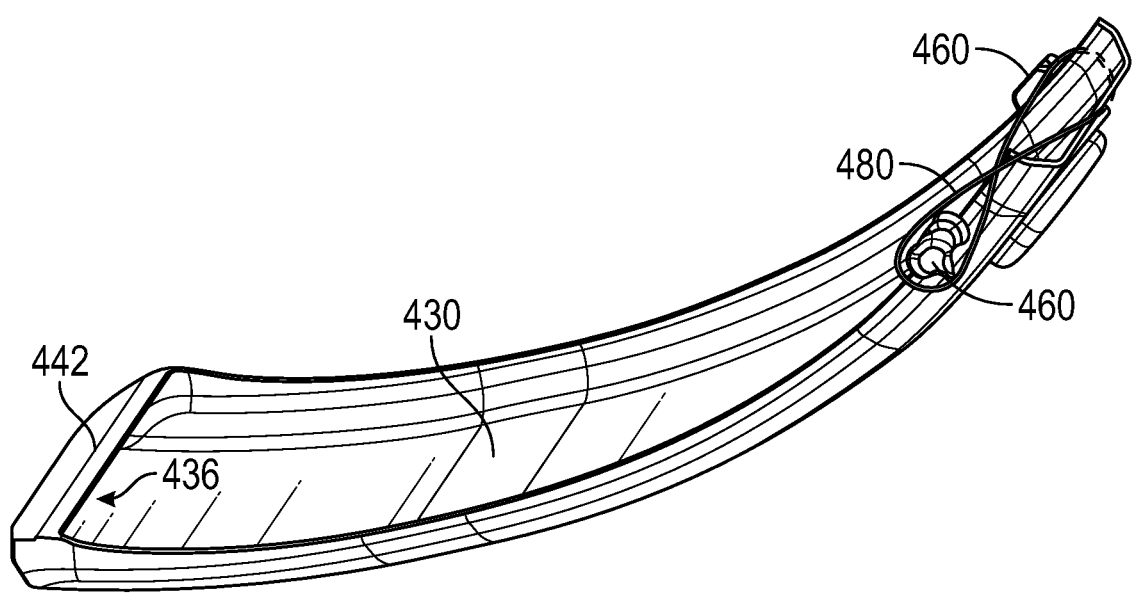

With reference to FIGS. 10A-10C, an example intermediate support piece 400 for coupling with a limb support device (for example, the limb support device 100, for example, shown in FIGS. 4A and 4C) and its various features are described herein. The intermediate support piece 400 may be a stiff piece placed between a sole (e.g., the sole body 302 shown in FIG. 8D) and a limb support device (e.g., a foot portion of the prosthetic leg or a prosthetic crutch). The intermediate support piece 400 may be fixedly attached to the sole and may include a support surface 402 and a recess 410 formed on the support surface 402. The intermediate support piece 400 may be permanently or removably coupled to the sole. The intermediate support piece 400 may be coupled to the sole body 302 using various types of fastening mechanisms including, but not limited to, adhesive(s), press fit connection, screws, nuts and bolts, clasps, pins, rivets, snap-fit connection, and the like.

The support surface 402 may receive a limb support device (e.g., a foot portion of the prosthetic leg or a prosthetic crutch). The recess 410 can mate with a corresponding protrusion of the limb support device (e.g., on a rear or bottom surface of the limb support device) to further assist in coupling the intermediate support piece 400 to the limb support device. In some implementations, the coupling between the recess 410 and the corresponding protrusion of the limb support device can be mechanical. Additionally and/or alternatively, the coupling between the recess 410 and the corresponding protrusion of the limb support device can be magnetic.

The intermediate support piece 400 can include a cover 442 and a slot 436. The slot 436 can be formed below the cover 442 that is positioned about a distal end of the intermediate support device 400. The slot 436 may be dimensioned to receive a toe portion of a limb support device (e.g., a prosthetic foot). Once the toe portion of the limb support device is inserted into the slot 436, the cover 442 can prevent the limb support device from being dislodged from the intermediate support piece 400 in a direction substantially orthogonal with respect to the body of the intermediate support piece 400.

In some implementations, the intermediate support device 400 can include knobs 460. The knobs 460 can extend laterally from side edges of the intermediate support device 400. During use, an elastic member 480 (e.g., a rubber O-ring or band) can be looped over the knobs 460 such that a limb support device (e.g., the limb support device 100 shown in FIG. 4A) is positioned between the elastic member 480 and the intermediate support device 400. The elastic member 480 can provide additional support that keeps the limb support device and the intermediate support device 400 coupled together.

Prosthetic Device

A fin, as described herein, can be implemented in a prosthetic device to improve the stiffness to weight ratio of the prosthetic device. In this way, a prosthetic device with a fin can achieve an increased stiffness and/or a reduced mass, as compared to a similar prosthetic device without a fin. Furthermore, the prosthetic device with the fin can retain energy storage capabilities (e.g., when a portion of the prosthetic foot is flexed under load) and can also retain energy return capabilities (e.g., when the prosthetic foot moves back from a flexed position responsive to a release of the applied load). The following disclosure describes non-limiting examples of a prosthetic foot or a component thereof, any of which may be manufactured using any combination of the methods described above.

Figure 11C:
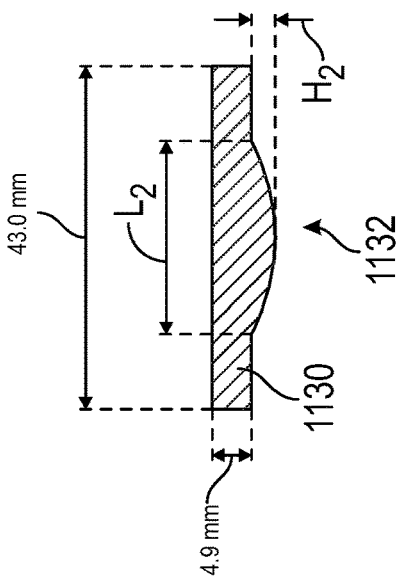
FIGS. 11A-11C illustrate cross-sectional views and dimensions of various example embodiments of a prosthetic feet.
Figure 11B:
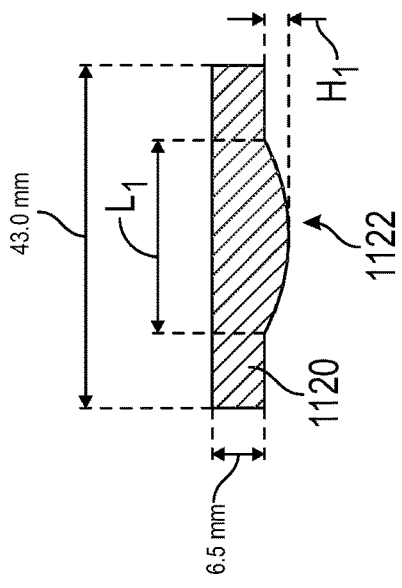
Figure 11A:
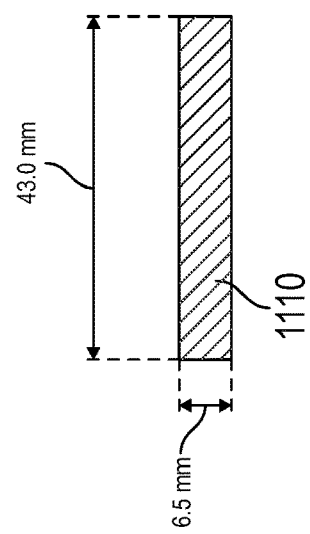

FIG. 11A illustrates a cross-sectional view of an example prosthetic foot 1110 that does not include a fin. As shown, the prosthetic foot 1110 has a rectangular cross section with a width of 43 mm and a thickness of 6.5 mm, and the cross-sectional area of the prosthetic foot 1110 is 279 mm$^2$. Furthermore, the moment of inertia about the horizontal x-axis ($I_{x\_Figure11A}$) is approximately 984 mm$^4$, and the moment of inertia about the vertical y-axis ($I_{y\_Figure11A}$) is approximately 43,066 mm$^4$. To calculate the moment of inertia, the following relationship can be used:

$$I_x = \frac{bh^3}{12} \quad \text{(Equation 1)}$$

$$I_y = \frac{hb^3}{12} \quad \text{(Equation 2)}$$

where b is the length of the base (this this example, 43 mm), and h is the height (in this example, 6.5 mm).

FIG. 11B illustrates a cross-sectional view of a prosthetic foot 1120 with a fin 1122. As shown, the prosthetic foot 1120 has a width of 43 mm and a varying thickness along the width. In particular, the cross section of the prosthetic foot 1120 has a thickness of 6.5 mm at the edges and increases in thickness at the fin 1122. For instance, in this example, the fin 1122 has a length ($L_1$) of 25 mm and a center height ($H_1$) of 3 mm. Furthermore, in this example, the cross-sectional area of the prosthetic foot 1120 is approximately 330 mm². Furthermore, the moment of inertia about the horizontal x-axis ($I_{x\_Figure11B}$) is approximately 1,870 mm⁴, and the moment of inertia about the vertical y-axis ($I_{y\_Figure11B}$) is approximately 44,770 mm⁴.

Consider a scenario in which a portion of each of the prosthetic feet 1110, 1120 is supported from a single end. In such a scenario, the maximum deflection at an opposite end of the portion of the prosthetic feet 1110, 1120 can be expressed using the single load cantilever beam deflection formula shown below:

$$\delta = \frac{FL^3}{3EI} \quad \text{(Equation 3)}$$

where L is the length of the portion of the prosthetic foot, δ is the deflection of the portion of the prosthetic foot, F is the force applied on the opposite end, E is flexural modulus (or modulus of elasticity), and I is moment of inertia of the portion of the prosthetic foot.

Assuming that the prosthetic devices 1110, 1120 are made from the same material, that the portions are the same length, and that the same amount of force applied, then a ratio between the moment of inertia of the prosthetic device 1110 and the moment of inertia of the prosthetic device 1120 can be used to determine a comparison of the stiffness of the prosthetic devices 1110, 1120. Accordingly, in this example, the ratio $$\left(\frac{I_{Fig.11A}}{I_{Fig.11B}} = \frac{984}{1870} = 0.53\right)$$

indicates that the prosthetic device 1120 (with the fin 1122) is about 53% stiffer than the prosthetic device 1110 (without a fin) for the same mass. Furthermore, the ratio of areas $$\left(\frac{\text{Area}_{FIG.11B}}{\text{Area}_{FIG.11A}} = \frac{330}{279} \approx 1.18\right)$$

indicates that the prosthetic device 1120 (with the fin 1132) allows for 53% increase in stiffness with only an 18% mass increase, as compared to the prosthetic device 1110.

The results of the foregoing stiffness comparison can be confirmed by deflection measurements (e.g., calculated by Equation 3). In particular, the deflection of the prosthetic device 1110 is 13 mm, while the deflection of the prosthetic device 1120 is 7 mm. A ratio of the deflections (7 mm/13 mm) also indicates that the prosthetic device 1120 is about 53% stiffer than the prosthetic device 1110.

FIG. 11C illustrates a cross-sectional view of a prosthetic foot 1130 with a fin 1132. As shown, the prosthetic foot 1130 has a width of 43 mm and a varying thickness along the width. In particular, the cross section of the prosthetic foot 1130 has a thickness of 4.9 mm at the edges and increases in thickness at the fin 1132. For instance, in this example, the fin 1132 has a length ($L_2$) of 25 mm and a center height ($H_2$) of 3 mm. Furthermore, in this example, the cross-sectional area of the prosthetic foot 1120 is approximately 261 mm². Furthermore, the moment of inertia about the horizontal x-axis ($I_{x\_Figure11C}$) is approximately 991 mm⁴.

Consider a scenario in which a portion of each of the prosthetic feet 1110, 1130 is supported from a single end. In such a scenario, the maximum deflection at an opposite end of the portion of the prosthetic feet 1110, 1120 can be expressed using Equation 3 above.

Assuming that the prosthetic devices 1110, 1130 are made from the same material, that the portions are the same length, and that the same amount of force applied, then a ratio between the moment of inertia of the prosthetic device 1110 and the moment of inertia of the prosthetic device 1130 can be used to determine a comparison of the stiffness of the prosthetic devices 1110, 1130. Accordingly, in this example, the ratio $$\left(\frac{I_{FIG.11A}}{I_{FIG.11C}} = \frac{984}{991} \approx 0.993\right)$$

calculates to 0.993, indicating that the prosthetic devices 1120 are approximately the same stiffness.

The results of the foregoing stiffness comparison can be confirmed by deflection measurements. In particular, the deflection of the prosthetic device 1110 is 13 mm, while the deflection of the prosthetic device 1130 is 13 mm. A ratio of the deflections (13 mm/13 mm) also indicates that the prosthetic devices 1110, 1130 are approximately the same stiffness. However, the ratio of areas $$\left(\frac{\text{Area}_{FIG.11C}}{\text{Area}_{FIG.11A}} = \frac{261}{279} \approx 0.94\right)$$

indicates that the prosthetic device 1130 (with the fin 1132) allows for a 6% mass reduction, while retaining approximately the same stiffness as the prosthetic device 1110.

FIGS. 12A-12E illustrate a perspective view, a bottom view, a top view, a side view, and a rotated perspective view, respectively, of an example of a prosthetic foot 1200 with a fin 1216, in accordance with the present disclosure. The prosthetic foot 1200 includes a body 1202 having an anterior surface 1210, a posterior surface 1212 opposite the anterior surface 1210, and a fin 1216 on the posterior surface 1212. It will be appreciated that the prosthetic foot 1200 can be an embodiment of any of the limb support devices described herein. Furthermore, the prosthetic foot 1200 represents an example prosthetic foot and other examples may use fewer, additional, or different components or arrangements.

The prosthetic foot 1200 can include a curved profile. For example, in some cases, as visible at least in FIG. 12D, the body 1202 has C-shape. In other examples, the body 1202 may have a different shape, such as a J-shape. The curved profile can facilitate improved user performance. For example, vertical forces generated during ambulation can cause the prosthetic foot 1200 to flex and store energy. The energy can be translated into a linear motion and returned to the user when the prosthetic foot 1200 moves back from a flexed position (e.g., at push-off). In this way, the prosthetic foot 1200 can reduce the need for the user to actively push her body forward using the prosthetic foot 1200, assists in taking a more equal stride length, and provides for a more natural gait and reduced walking effort. In some implementations, the prosthetic foot 1200 can be a sport foot (e.g., used for sprinting or running).

The prosthetic foot can be made of a composite material, such as carbon fiber, glass fiber, or a carbon-glass fiber composite. For example, the prosthetic foot 1200 can include carbon fiber layers including a plurality of fibers. The plurality of fibers may extend generally in the same direction. For example, the plurality of fibers can be parallel or collinear to each other, such as along the length or width of the body 1202. In some cases, the prosthetic foot 1200 can be made of other suitable materials. In some instances, the prosthetic foot 1200 can include material (e.g., a composite material) that can flex to provide energy storage and return to the user during ambulation. For instance, a carbon fiber composite can allow more flexion than a rigid material, thereby offering increased energy storage (e.g., when a portion of the prosthetic foot 1200 is flexed under load) and energy release (e.g., when the prosthetic foot 1200 moves back from a flexed position responsive to a release of the applied load).

The prosthetic foot can be manufactured using either dry fiber composite materials or pre-impregnated fiber composite materials. Depending on what composite material is being used, a curing agent may or may not be added. For example, when using the dry fiber composite materials, a curing agent may be added to the mold (e.g., mold 50 in FIGS. 3A-3B). Alternatively, when using pre-impregnated fiber composite materials, a curing agent may not be needed since the curing agent may already present. In some implementations, depending on what composite material is being used, heat may or may not be applied during the curing process. For example, when using the dry fiber composite materials (e.g., in addition to a curing agent), additional heat may be applied during the curing process (e.g., depending on the dry fiber composite and curing agent used), or the addition of a curing agent may initiate an exothermic chemical reaction that can provide heat during the curing process (e.g., making it unnecessary for additional heat to be applied during the curing process). In some implementations, when using pre-impregnated (prepreg) fiber composite material, heat is applied to initiate the curing process.

In some implementations, pressure (e.g., vacuum or low pressure) can be applied during the curing process to cause the mold to be completely filled out and/or ensure that any air present or formed in the mold is sucked or pressed out. This may lead to stronger chemical bonds generated within the cured composite material and/or the curing agent.

The prosthetic foot 1200 can include a fin 1216, which can be an embodiment of any of the fins described herein, such as fin 1122. As described herein, the fin 1216 increases the stiffness of the structure in which is implemented. Accordingly, in this example, the fin 1216 increases the stiffness of the body 1202 of the prosthetic foot 1200 (e.g., relative to the prosthetic foot 1200 without the fin 1216). As described herein, the fin 1216 can include a ridge or protrusion that extends outwardly from the body 1202 of the prosthetic foot (e.g., outwardly relative to portions of the posterior surface 1212 adjacent the fin 1216). In the illustrated example of FIGS. 12A-12E, the fin 1216 is located on the posterior surface 1212 of the body 1202. However, in some cases, the fin 1216 can alternatively or additionally be located on the anterior surface 1210 of the body 1202, or can alternatively or additionally be located on one or more sides of the body 1202. Further still, in some implementations, the prosthetic foot 1200 includes multiple ribs 1216, which may be located on the posterior surface 1212 and/or the anterior surface 1210.

The fin 1216 can extend along a longitudinal axis of prosthetic foot 1200. In some cases, the fin 1216 extends along a majority of a length of the prosthetic foot 1200, such as extending approximately 60%, 70%, 80%, or 90% of the length of the prosthetic foot 1200. In other instances, the fin 1216 extends along approximately half the length of the prosthetic foot 1200. Further still, in some cases, the fin 1216 extends along a minority of the length of the prosthetic foot 1200, such as extending approximately 10%, 20%, 30%, or 40% of the length of the prosthetic foot 1200.

Figure 12A:
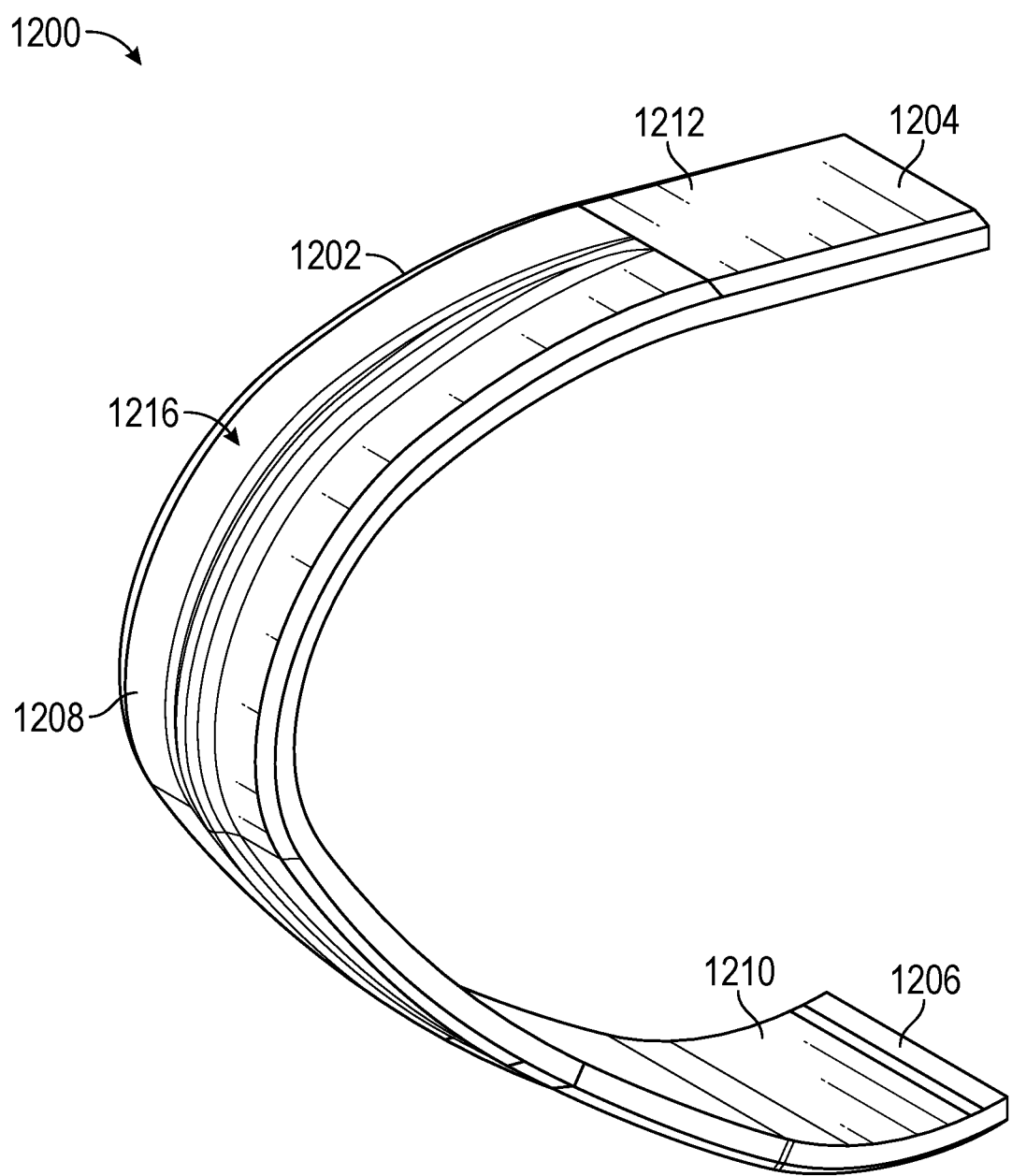
FIGS. 12A-12E illustrate a perspective view, a bottom view, a top view, a side view, and a rotated perspective view, respectively, of an example embodiment of a prosthetic foot with a fin, in accordance with the present disclosure.
Figure 12B:
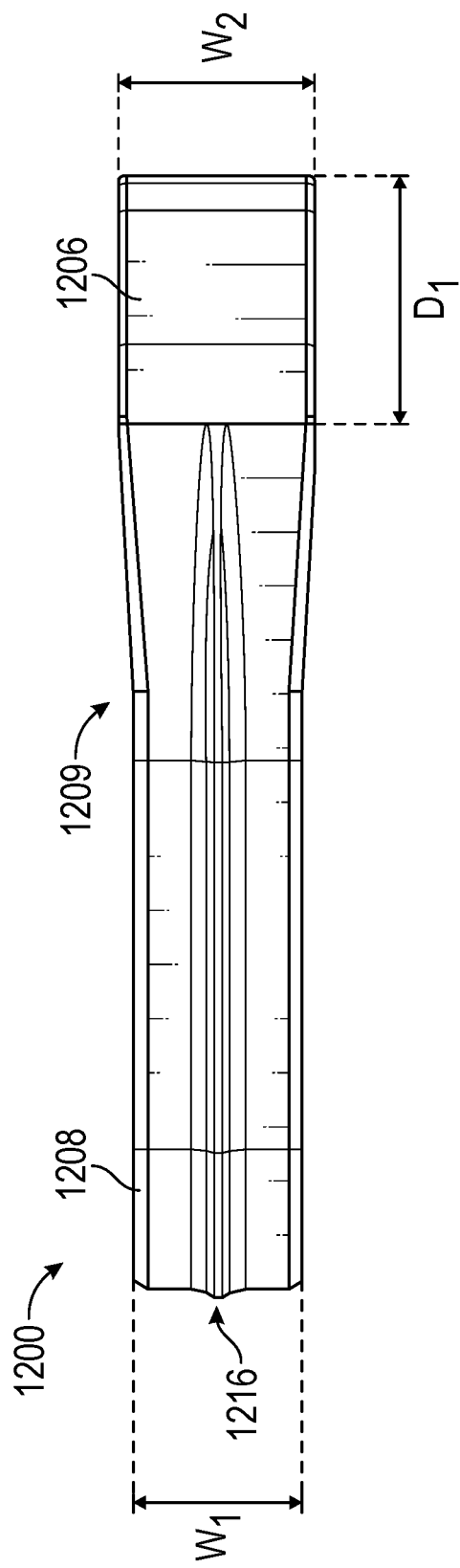
Figure 12C:
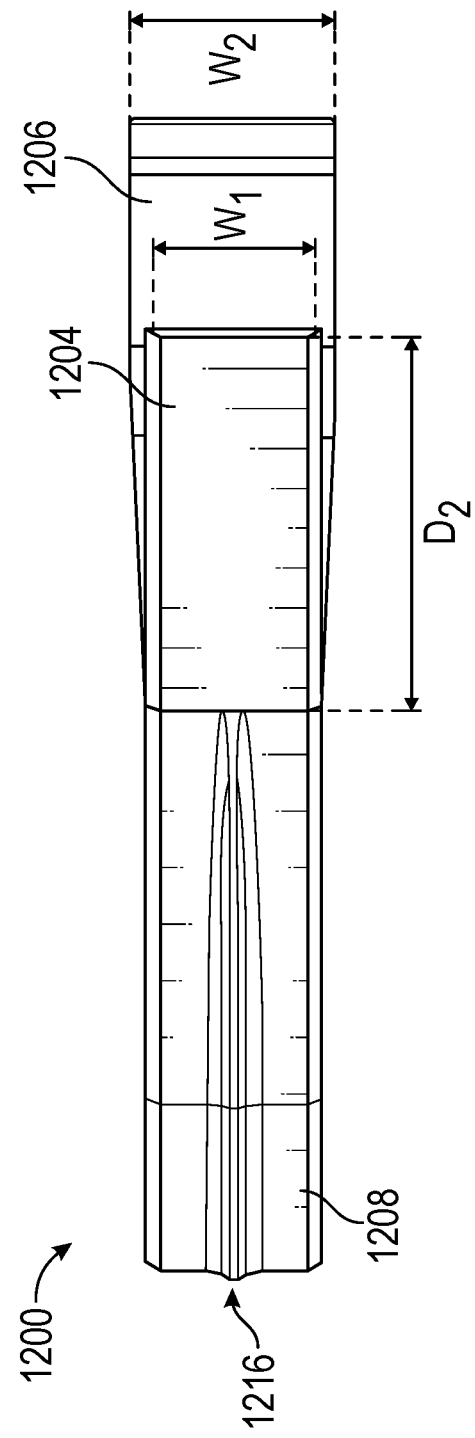
Figure 12D:
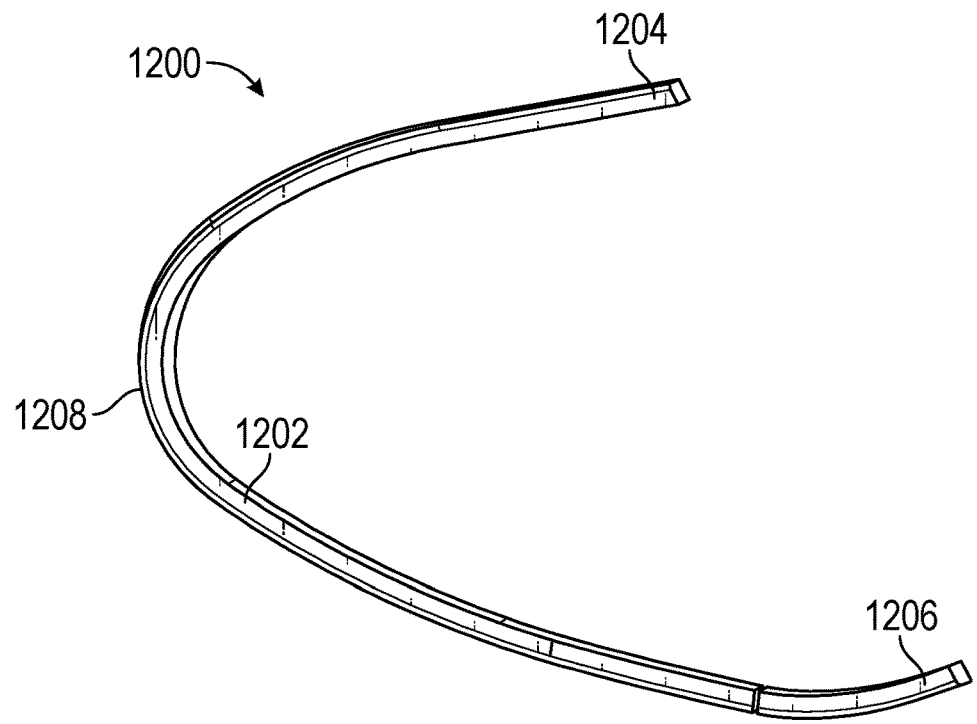
Figure 12E:
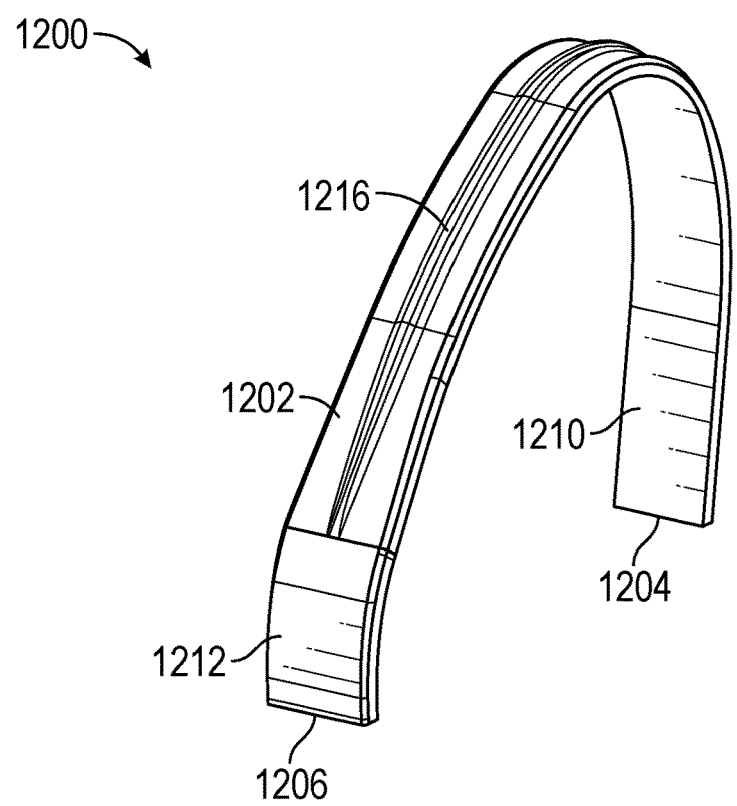

In some cases, the fin 1216 does not extend to the end of the distal portion 1206. For example, as illustrated by FIG. 12B, in some cases, there is some distance, $D_1$, between the end (e.g., a distal end) of the fin 1216 and the end of the distal portion 1206. The distance, $D_1$, can vary across implementations. Furthermore, in some cases, the fin 1216 extends to the end of the distal portion 1206, such that $D_1$ is zero. Similarly, in some cases, the fin 1216 does not extend to the end of the proximal portion 1204. For example, as illustrated by FIG. 12C, in some cases, there is some distance, $D_2$, between the end (e.g., a proximal end) of the fin 1216 and the end of the proximal portion 1204. The distance, $D_2$, can vary across implementations. Furthermore, in some cases, the fin 1216 extends to the end of the proximal portion 1204, such that $D_2$ is zero.

As illustrated, the fin 1216 can extend along a centerline the prosthetic foot 1200. As another example, the fin 1216 can extend along an axis that is parallel to and offset from the centerline of the prosthetic foot 1200, such as along a left or right side of the prosthetic foot 1200. In addition or alternatively, the fin 1216 can extend along an axis that is not parallel to the centerline of the prosthetic foot 1200. For example, the fin 1216 may extend at an angle with respect to the centerline of the prosthetic foot 1200. The particular angle between the fin 1216 and the centerline of the prosthetic foot 1200 may vary across implementations. For example, the angle between the fin 1200 and the centerline of the prosthetic foot 1200 may be 5, 10, 20, 30, 45, or 60 degrees (+/−a few degrees). In some implementations, the fin 1216 can extend at an angle with respect to the centerline of the prosthetic foot 1200 to help guide the rollover of the prosthetic foot 1200 during use.

In some cases, the body 1202 has a varying width along its length. For example, as illustrated in FIGS. 12B and 12C, the proximal portion 1204 and/or the central portion (e.g., curved portion) 1208 of the of the prosthetic foot 1200 may be narrower (e.g., have a smaller width ($W_1$) transverse to the longitudinal axis of the body 1202 viewed from the anterior surface 1210) than the width ($W_2$) of the distal portion 1206. In some examples, the central portion 1208 can be narrower than the distal portion 1206 so that the width of the distal portion 1206 flares outward (e.g., gradually flares outward starting at location 1209) from the central portion 1208 to the distal portion 1206.

A narrowed proximal portion 1204 and/or the central portion 1208 can advantageously reduce drag on the prosthetic foot 1200, for example by reducing the amount of surface area of the prosthetic foot 1200 that faces airflow during use. Furthermore, a narrowed proximal portion 1204 and/or the central portion 1208 advantageously reduces a mass and/or weight of prosthetic foot 1200. Further still, a narrowed proximal portion 1204 and/or the central portion 1208 can also advantageously enhance energy return or flexure (e.g., reduced resistance to flexion) of the prosthetic foot 1200 in use, while the increases thickness from the fin 1216 advantageously increases the stiffness.

Figure 13A:
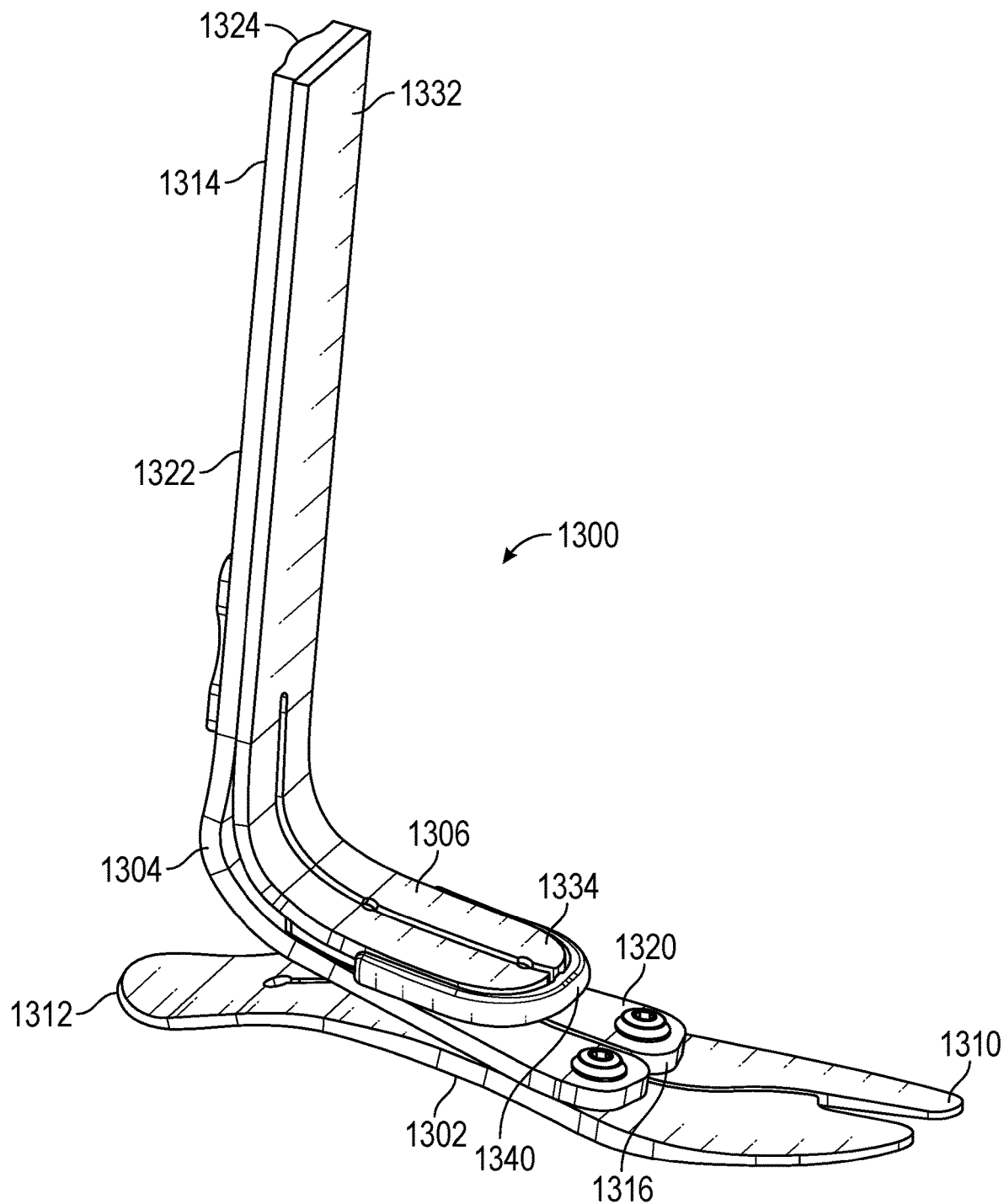
FIGS. 13A-13C illustrate a perspective view, a back view, and a bottom view, respectively, of an example embodiment of a prosthetic foot with a fin, in accordance with the present disclosure.
Figure 13C:
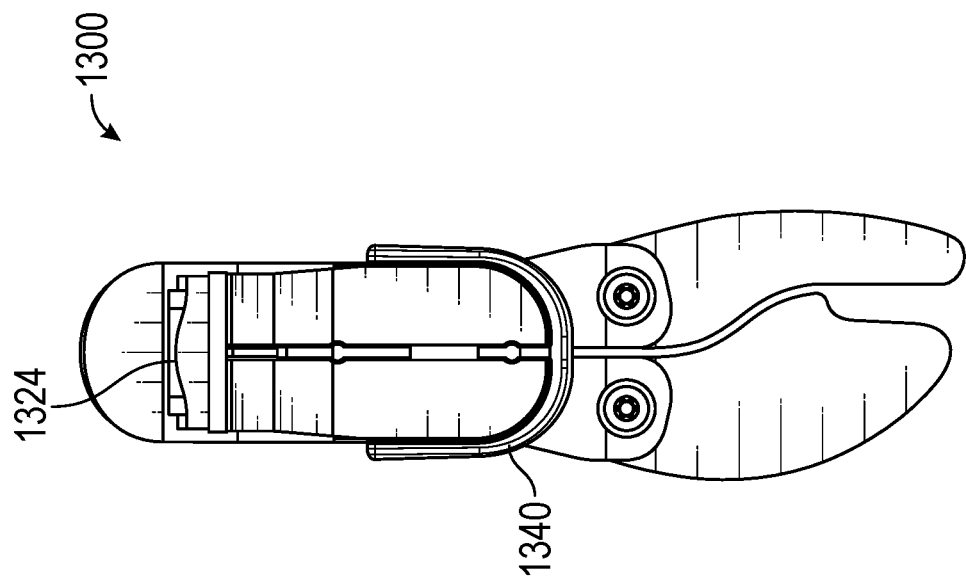
Figure 13B:
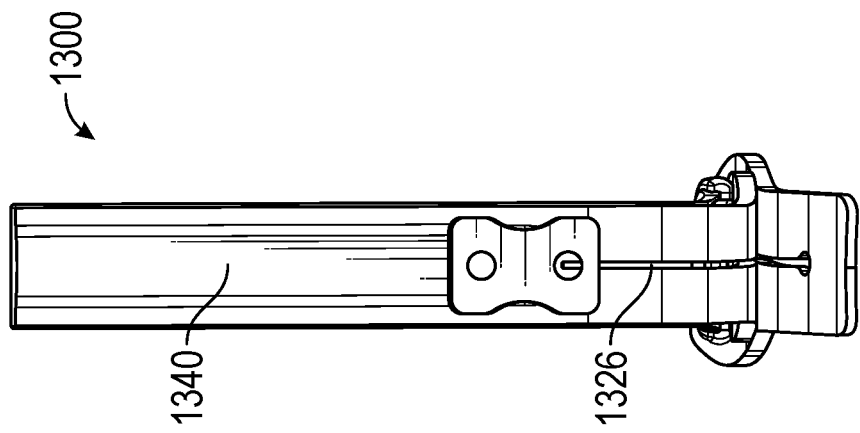

FIGS. 13A-13C illustrate a perspective view, a back view, and a bottom view, respectively, of an example of a prosthetic foot 1300 with a fin 1324, in accordance with the present disclosure. The prosthetic foot 1300 can include a first footplate 1302, a second footplate 1304, a third footplate 1306, a spacer 1340, and a fin 1324. It will be appreciated that the prosthetic foot 1300 represents an example prosthetic foot and other examples may use fewer, additional, or different components or arrangements. For example, the prosthetic foot 1300 may not include the third footplate 1306 and/or the spacer 1340. Furthermore, it will be understood that the prosthetic foot 1300 can be an implementation of, or include one or more features of, the prosthetic foot 1100 of FIGS. 11A-11E, the prosthetic foot 1200 of FIGS. 12A-12E, and/or any of the limb support devices described herein.

The first footplate 1302 can include a proximal portion 1312 and a distal portion 1310. During ambulation, the proximal portion 1312 and a distal portion 1310 of the first footplate 1302 can operatively engage a support surface. For example, during ambulation, a bottom surface of the proximal portion 1312 and a distal portion 1310 of the first footplate 1302 can operatively engage a walking surface, such as the ground.

The second footplate 1304 can include a proximal portion 1314 and a distal portion 1316. The distal portion 1316 of the second footplate 1304 can be coupled (e.g., with fasteners, such as bolts) to the first footplate 1302 at an intermediate location between the proximal portion 1312 and a distal portion 1310 of the first footplate 1302. Furthermore, the second footplate 1304 can include an anterior surface 1320, a posterior surface 1322 opposite the anterior surface, and a fin 1324 on the posterior surface 1322. In some cases, the second footplate 1304 has transverse cross-section with a linear anterior edge and a posterior edge that defines a curved ridge (e.g., of the fin 1324) that extends from linear sides. As described herein, a spacer 1340 can be positioned on the second footplate 1304 and coupled to the curved ridge (e.g., curved side edges of the second footplate 1304).

The second footplate 1304 can be generally L-shaped. The L-shape can facilitate improved user performance. For example, vertical forces generated during ambulation cause the second footplate 1304 to flex and store energy. The energy can be translated into a linear motion and returned to the user when the second footplate 1304 moves back from a flexed position (e.g., at push-off).

The second footplate 1304 can include a slot 1326 that extends along at least a portion of the length of the second footplate 1304 and can define separate blades of the second footplate 1304. In some cases, the slot 1326 may not extend across the fin 1324. In some cases, the slot 1326 can extend across an end or a portion of the fin 1324. In other implementations, the second footplate 1304 can exclude the slot 1326.

The third footplate 1306 can include a proximal portion 1332 and a distal portion 1334. The third footplate 1306 can be arranged adjacent to the anterior surface 1320 of the second footplate 1304 along at least a portion of the third footplate 1306. As described in more detail herein, the distal portion 1334 of third footplate 1306 can be spaced apart from the second footplate 1304 when the prosthetic foot 1300 is in stance phase (or between heel strike and stance phase). Furthermore, the distal portion 1334 of third footplate 1306 can operatively engage the anterior surface 1320 of the distal portion 1310 of the second footplate 1304 in dorsi-flexion (e.g., up to and including toe-off).

The spacer 1340 can be positioned between the second footplate 1304 and the third footplate 1306. In some cases, the spacer 1340 includes side edges that engage at least a portion of side edges of the second footplate 1304. In some cases, the spacer 1340 includes a groove on a bottom along longitudinal axis of the spacer 1340, as further discussed below.

Figure 13D:
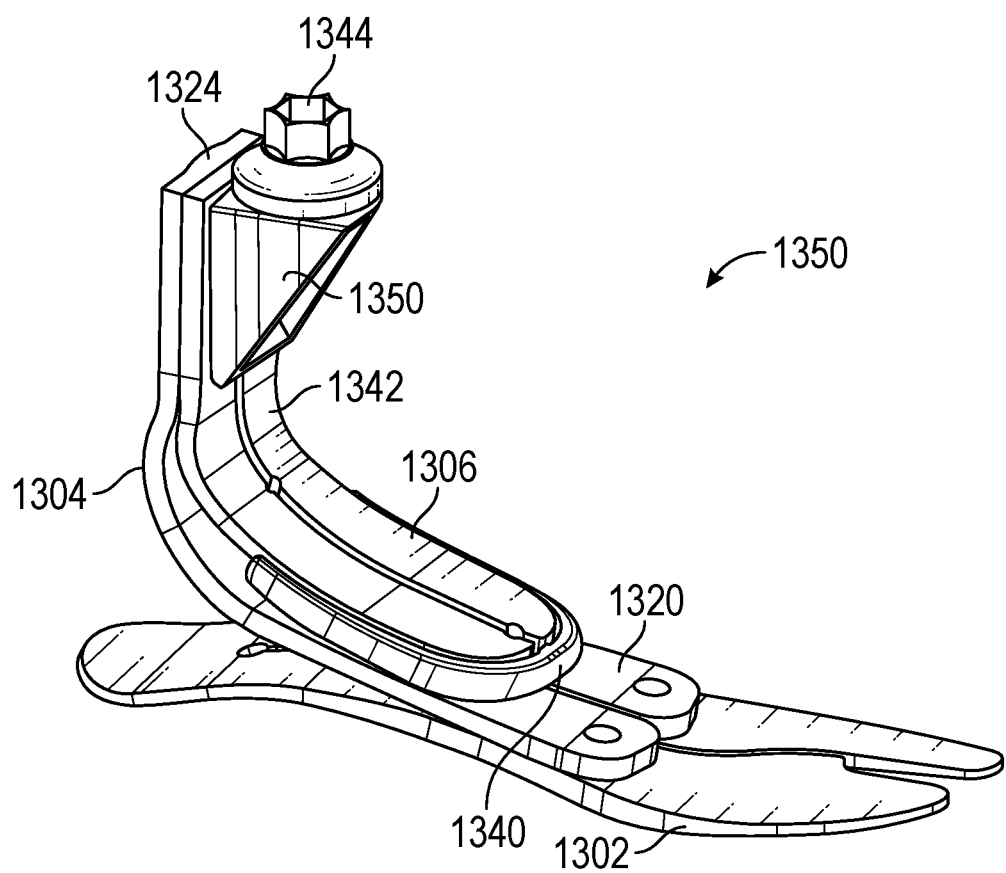
FIG. 13D illustrates a perspective view of an example embodiment of a prosthetic foot with a fin, in accordance with the present disclosure.

FIG. 13D illustrates an example of a prosthetic foot 1350, which is an implementation of the prosthetic foot 1300, and to which the same description above for FIGS. 13A-13C applies. The prosthetic foot 1350 can include a first footplate 1302, a second footplate 1304, a third footplate 1306, a spacer 1340, and a fin 1324. In this example, the prosthetic foot 1350 has a shorter height than the prosthetic foot 1300. The prosthetic foot 1300 can include an adapter 1350, which is attached to an anterior surface 1342 of the third footplate 1306. Furthermore, the prosthetic foot 1350 can optionally include a pyramid connector 1344 for connection to another prosthetic device (e.g., pylon). It will be appreciated that the prosthetic foot 1350 represents an example prosthetic foot and other examples may use fewer, additional, or different components or arrangements, such as any of the components or arrangements described herein.

Figure 14A:
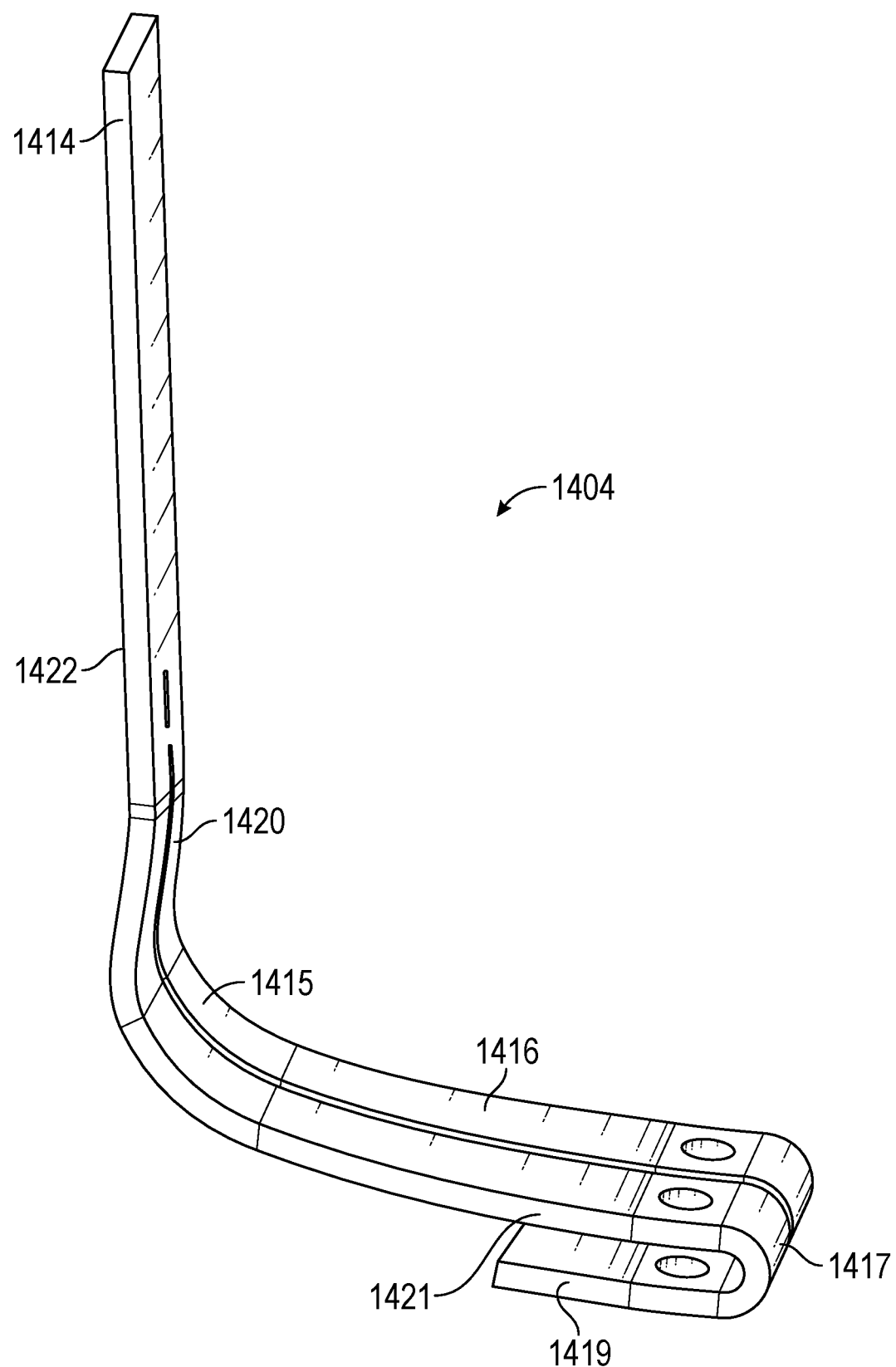
FIG. 14A illustrates a perspective view of an example embodiment of a footplate of an example prosthetic foot.

FIG. 14A illustrates a perspective view of a footplate 1404 of an example prosthetic foot 1400. The footplate 1404 can be an implementation of, or at least partially similar to, the second footplate 1304 of FIGS. 13A-13C, and to which the description above applies except as discussed below. The footplate 1404 can be generally Z-shaped (e.g., the footplate 1404 changes direction in at least two locations) and can include an anterior surface 1420 and a posterior surface 1422 opposite the anterior surface. Additionally, the footplate 1404 can include a linear proximal portion 1414 and a curved distal portion 1416. The distal portion 1416 can curve rearward at transition section 1415 (e.g., at ankle region), and then can extend forwardly toward a front end and transition at transition section 1417 (e.g., proximate toe region) into a portion 1419 that folds under another portion 1421 of the footplate 1404.

Figure 14B:
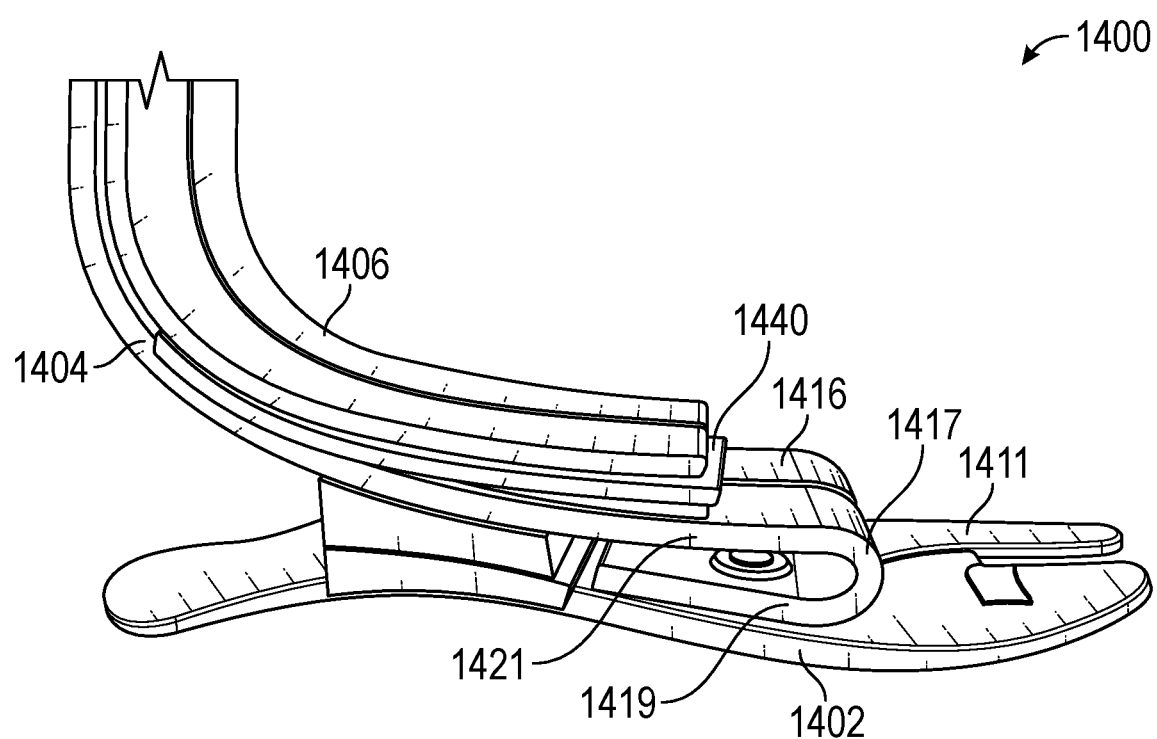
FIG. 14B illustrates a perspective view of an example embodiment of a prosthetic foot.

FIG. 14B illustrates a perspective view of an example of a prosthetic foot 1400. The prosthetic foot 1400 can include a first footplate 1402, a second footplate 1404, a third footplate 1406, and a spacer 1440, which can be implementations of, or at least partially similar to, the first footplate 1302, the second footplate 1304, the third footplate 1306, and/or the spacer 1340, respectively, of FIGS. 13A-13C. The spacer 1440 can be disposed between the second footplate 1404 and third footplate 1406 but not extend about side edges of the third footplate 1406. It will be appreciated that the prosthetic foot 1400 represents an example prosthetic foot and other examples may use fewer, additional, or different components or arrangements. Furthermore, it will be understood that the prosthetic foot 1400 can be an implementation of, or include one or more features of, any of the limb support devices described herein.

In the illustrated example of FIG. 14B, the distal portion 1416 of the second footplate 1404 has a bottom portion 1419 that folds under another portion 1421 of the second footplate 1404. Furthermore, a posterior surface of the bottom portion 1417 can be coupled to (e.g., with fasteners, such as bolts)

an anterior surface 1411 of the first footplate 1402. In this example, the second footplate 1404 is generally Z-shaped (e.g., changes direction in at least two locations).

Figure 15A:
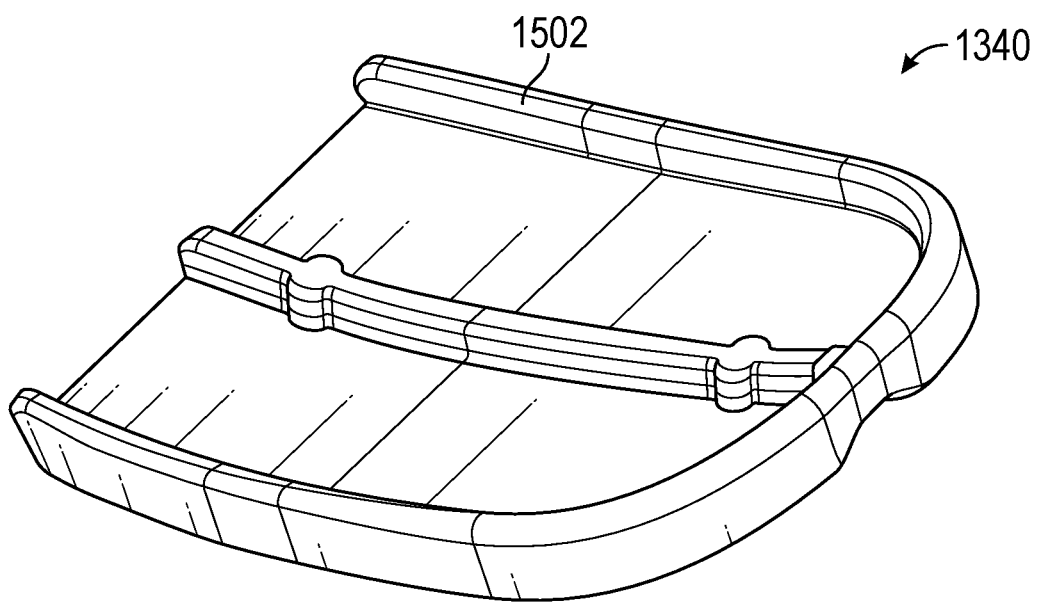
FIGS. 15A-15B illustrate an example embodiment of a spacer of the prosthetic foot of FIGS. 13A-13C.
Figure 15B:
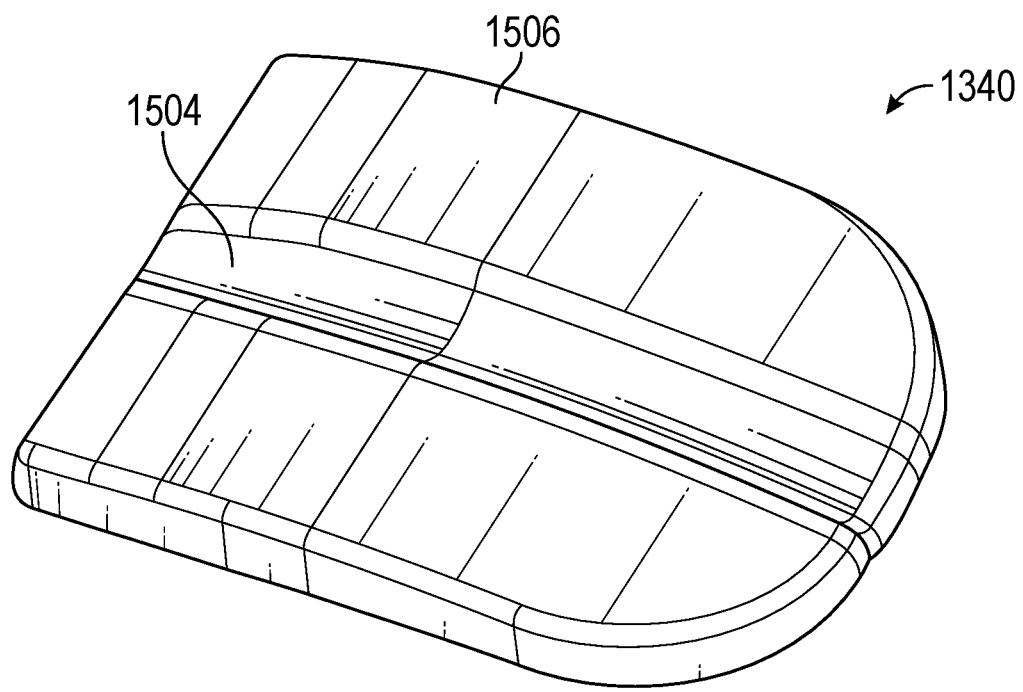

FIGS. 15A-15B illustrate the spacer 1340 of the prosthetic foot 1300 of FIGS. 13A-13C. Optionally, the spacer 1340 can be implemented in the prosthetic foot 1400 of FIG. 14. With reference to FIGS. 13A-13C, the spacer 1340 can be positioned between the second footplate 1304 and the third footplate 1306. The spacer 1340 may be removable or fixed to the second footplate 1304. In some cases, the spacer 1340 includes side edges 1502 that engage and/or disposed proximate or adjacent at least a portion of side edges of the third footplate 1306. In some cases, the spacer 1340 includes a groove 1504 on a bottom 1506 of the spacer 1340, such as along a longitudinal axis of the spacer 1340. In some cases, the shape, edges 1502, and/or groove 1504 facilitate production. For example, the spacer 1340 can steer or position itself on the blade for gluing, and the spacer 1340 can reduce a likelihood that a user sees glue on the edges of the third footplate 1306, and/or that glue flows out between the spacer and the edges of the third footplate 1306. In some cases, the spacer 1340 does not hug the sides of the third footplate 1306, but instead is positioned entirely between the second footplate 1304 and the third footplate 1306.

In some cases, the spacer 1340 is made of foam or other resilient and/or compressible materials. In some cases, the spacer 1340 can inhibit (e.g., prevent) or reduce the amount of noise generated during use of the prosthetic foot 1300 (e.g., due to interaction between the second and third footplates 1304, 1306). For example, the spacer 1340 can reduce the likelihood of sand or dirt from being caught between the blades, creating noise. In some cases, the spacer 1340 can limit vibration/kick felt by a user during use. Furthermore, in some cases, the spacer 1340 can facilitate a smooth rollover.

Figure 16B:
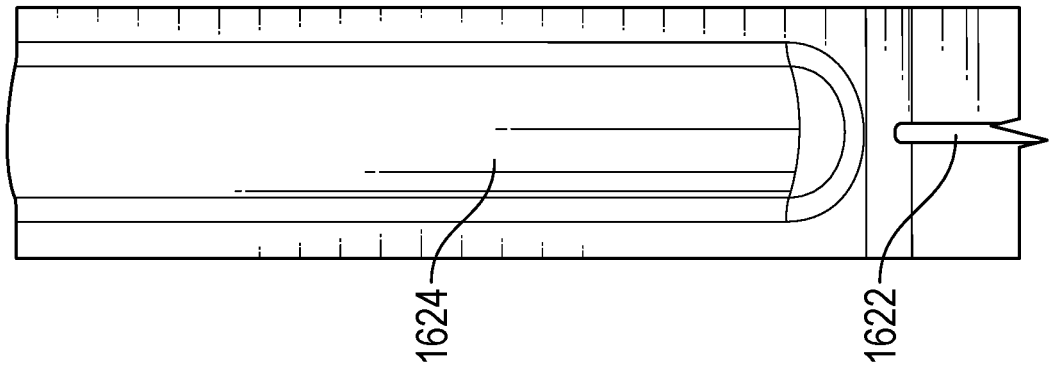
FIGS. 16A-16B illustrate example embodiments of slots in a footplate of a prosthetic foot.
Figure 16A:
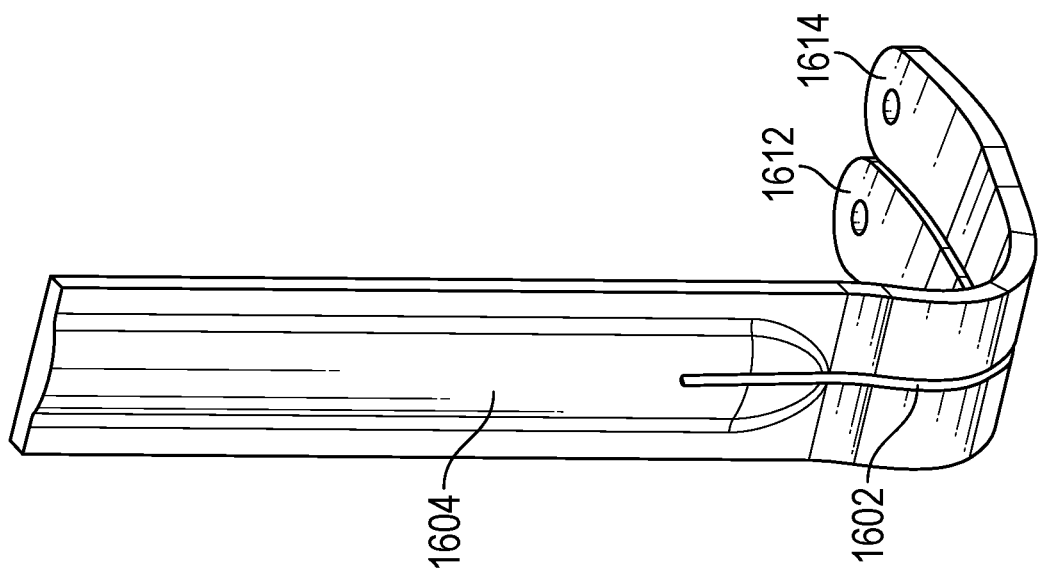

FIGS. 16A-16B illustrate example implementations of slots in a footplate of a prosthetic foot, which can correspond to the second footplate 1304 of prosthetic foot 1300 described above. The features of the footplate in FIGS. 16A-16B can also be incorporated into the second footplate 1404 of the prosthetic foot 1400 described above. As shown in FIG. 16A, in some cases, the slot 1602 can extend along a minority of the length of the footplate. Alternatively, in some cases, the slot 1602 can extends along a majority of the length of the footplate. Furthermore, the slot 1602 can define separate blades 1612, 1614 of the footplate. As shown in FIG. 16A, in some cases, the slot 1602 can extend across an end or a portion of the fin 1604. Alternatively, as shown in FIG. 16B, in some cases, the slot 1622 may not extend across an end or a portion of the fin 1624.

Figure 17:
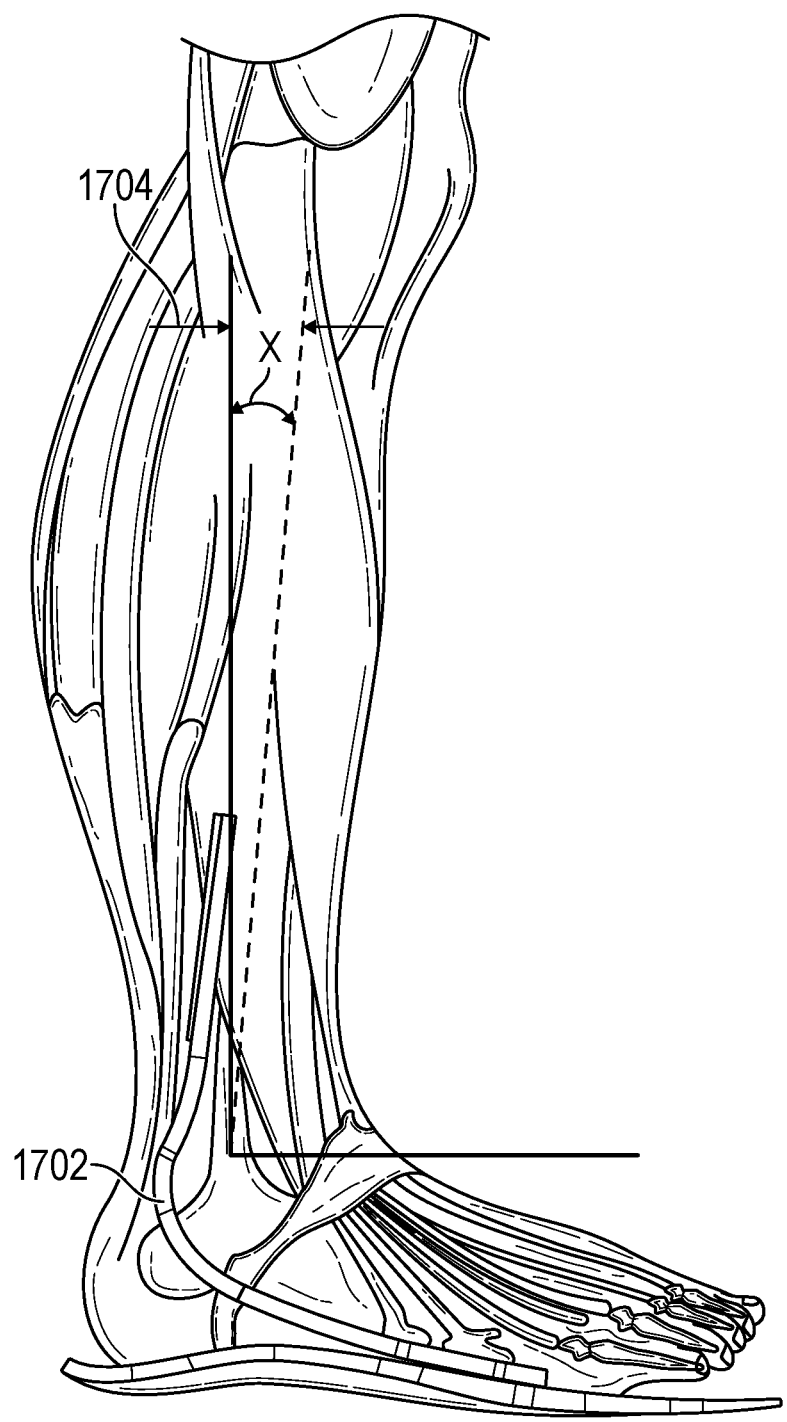
FIG. 17 illustrates an example embodiment of a prosthetic foot overlaid on an image of a sound limb.

FIG. 17 illustrates an example prosthetic foot 1702 overlaid on an image of a sound limb 1704. The prosthetic foot 1702 can be an implementation of any of the prosthetic devices described herein (e.g., prosthetic foot 1300, 1400). As shown, in some cases, the prosthetic foot 1702 can have an angular lean, x, where x is the angular offset from 90 degrees (e.g., from vertical). The angular lean, x, can vary across implementations. For example, x can be 1, 2, 3, 4, 5, 6, 7, 9, or 10 degrees, less than 15 degrees, greater than 2 degrees, between 3 and 10 degrees, etc. In some cases, the angular lean eases the prosthetic foot alignment when the foot is cut for different build heights.

Figure 18A:
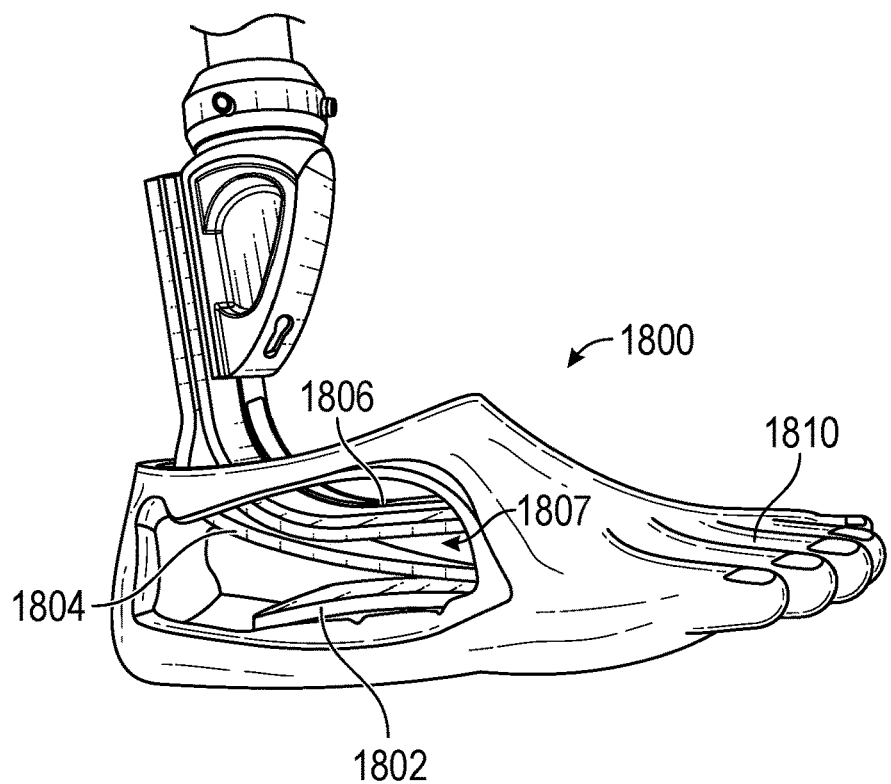
FIGS. 18A and 18B illustrate side views of an example prosthetic foot at various stages of a gait cycle.
Figure 18B:
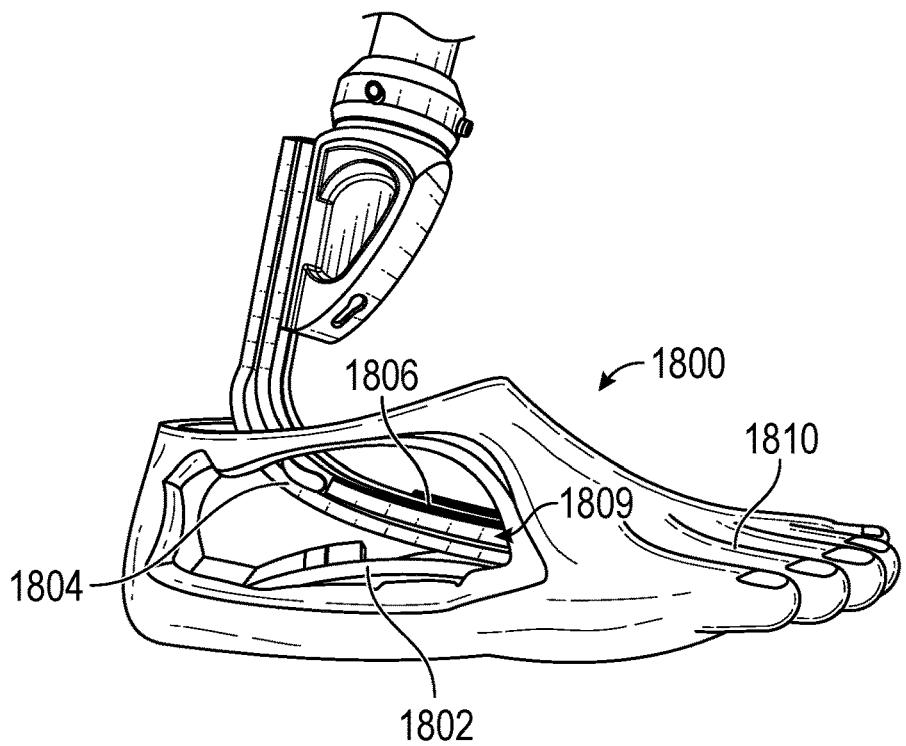

FIGS. 18A and 18B illustrate an example prosthetic foot 1800 at various stages of a gait cycle. In this example, the prosthetic foot 1800 can be an implementation of, or include one or more features of, the prosthetic foot 1300 of FIGS. 13A-13C. For example, the prosthetic foot 1800 can include a first footplate 1802, a second footplate 1804, and a third footplate 1806.

FIG. 18A illustrates the prosthetic foot 1800 at the heel contact stage of the gait cycle. As indicated by the space 1807 between the second footplate 1804 and the third footplate 1806, at heel contact, the top blade (that is, third footplate 1806) is not active (e.g., not engaged with the second footplate 1804). Rather, at heel contact, only the main blade (second footplate 1804) is active (e.g., flexing, storing energy). FIG. 18B illustrates the prosthetic foot 1800 in a dorsi-flexed stage of the gait cycle. As indicated by the contact 1809 between the second footplate 1804 and the third footplate 1806, at mid stance, the top blade (third footplate 1806) is active (e.g., flexing, storing energy). Furthermore, there is progressive stiffening of the foot from mid stance to toe-off, when the top blade supports the main blade.

Example Embodiments

The following are numbered example embodiments of various embodiments of the limb support device, the modular sole apparatus, the prosthetic device, the composite articles, and any other features disclosed herein. Any of the below Examples 1-49, or any other examples disclosed herein, may be combined in whole or in part. Elements of the examples disclosed herein are not limiting.

Example 1: A composite article manufactured from layers of composite material, the composite article comprising a first portion having a first width, a second portion, a transition portion, a plurality of layers of fibrous material, and a first polymer. The second portion is distally positioned from the first portion and having a second width different than the first width. The transition portion is located between the first portion and the second portion, the transition portion having at least a first contour transitioning between the first width and the second width. The plurality of layers of fibrous material extends and is continuous between the first portion and the second portion. The first polymer is impregnated with the plurality of layers of fibrous material and polymerized during a curing process, the first polymer causing the plurality of layers of fibrous material to realign to a shape substantially similar to the first contour during the curing process.

Example 2: The composite article of any of the Examples 1-8 or any other embodiment described herein, wherein the composite article is one of a prosthetic foot and a crutch blade.

Example 3: The composite article of any of the Examples 1-8 or any other embodiment described herein, wherein the first portion is located at a first end of the composite article, and wherein the second portion is located at a second end of the composite article.

Example 4: The composite article of any of the Examples 1-8 or any other embodiment described herein, wherein the first polymer is impregnated with the plurality of layers after the plurality of layers are placed into a mold having a desired shape comprising at least the first contour.

Example 5: The composite article of any of the Examples 1-8 or any other embodiment described herein, wherein the composite article comprises a fin, the fin formed on a rear surface of the composite article and extending along at least a portion of a length of the composite article.

Example 6: The composite article of any of the Examples 1-8 or any other embodiment described herein, wherein the fin increases stiffness of the composite article.

Example 7: The composite article of any of the Examples 1-8 or any other embodiment described herein, wherein the fin allows the composite article to maintain same level of stiffness with less material.

Example 8: The composite article of any of the Examples 1-8 or any other embodiment described herein, wherein the fin comprises at least a portion of the plurality of layers of fibrous material.

Example 9: A limb support device comprising a body. The body comprising a proximal portion with a first width, a distal portion with a second width greater than the first width, a transition portion between the proximal portion and the distal portion, the transition portion with a tapered width that transitions from the first width to the second width, and a plurality of layers of fibrous material having a plurality of fibers, each of the plurality of fibers extending linearly and continuously along each of the proximal portion, the transition portion, and the distal portion, the plurality of fibers generally parallel to each other and to outer edges of the proximal portion, the distal portion, and the transition portion.

Example 10: The limb support device of any of the Examples 9-17 or any other embodiment described herein, wherein the limb support device is a prosthetic foot.

Example 11: The limb support device of any of the Examples 9-17 or any other embodiment described herein, wherein the limb support device is a blade of a crutch.

Example 12: The limb support device of any of the Examples 9-17 or any other embodiment described herein, wherein one or more of the proximal portion, the distal portion, and the transition portion comprises a non-rectangular cross-section.

Example 13: The limb support device of any of the Examples 9-17 or any other embodiment described herein, wherein one or more of the proximal portion, the distal portion, and the transition portion comprises one or more fins on a surface thereof, the one or more fins having a greater thickness than adjacent portions of the body.

Example 14: The limb support device of any of the Examples 9-17 or any other embodiment described herein, wherein the one or more fins are in the proximal portion.

Example 15: The limb support device of any of the Examples 9-17 or any other embodiment described herein, wherein the one or more fins extend generally along an axial centerline of the body.

Example 16: The limb support device of any of the Examples 9-17 or any other embodiment described herein, wherein the one or more fins extend on a rear surface of the body.

Example 17: The limb support device of any of the Examples 9-17 or any other embodiment described herein, wherein one or more of the proximal portion, the distal portion, and the transition portion comprises a cross-section comprising a front surface and a rear surface, the front surface and the rear surface generally parallel to each other, a left edge and a right edge, the left edge and the right edge generally parallel to each other, a first chamfer between the left edge and either one of the rear surface or the front surface, and a second chamfer between the right edge and either one of the rear surface or the front surface.

Example 18: A limb support device comprising a first portion, a second portion, a plurality of layers of fibrous material, and a first polymer. The first portion having a first dimension along a first axis, the second portion having a second dimension along the first axis, the plurality of layers of fibrous material extending and continuous between the first portion and the second portion, and the first polymer impregnating the plurality of layers of fibrous material and polymerized during a curing process, the first polymer causing the plurality of layer of fibrous material to realign to a shape corresponding to a contour of an intermediate portion of the composite article between the first portion and the second portion during the curing process.

Example 19: A prosthetic foot comprising a continuous body extending from a proximal end to a distal end, the body comprising an anterior surface, a posterior surface opposite the anterior surface, and a fin on the posterior surface.

Example 20: The prosthetic foot of any of the Examples 19-30 or any other embodiment described herein, wherein the body has a C-shape.

Example 21: The prosthetic foot of any of the Examples 19-30 or any other embodiment described herein, wherein the body has a J-shape.

Example 22: The prosthetic foot of any of the Examples 19-30 or any other embodiment described herein, wherein the fin extends along a longitudinal axis of the prosthetic foot.

Example 23: The prosthetic foot of any of the Examples 19-30 or any other embodiment described herein, wherein the fin extends along a majority of a length of the prosthetic foot.

Example 24: The prosthetic foot of any of the Examples 19-30 or any other embodiment described herein, wherein the fin is defined on the posterior surface within a center portion of the prosthetic foot between a proximal portion and a distal portion.

Example 25: The prosthetic foot of any of the Examples 19-30 or any other embodiment described herein, wherein the fin protrudes relative to the posterior surface sections adjacent to fin.

Example 26: The prosthetic foot of any of the Examples 19-30 or any other embodiment described herein, wherein the fin defines a ridge on the posterior surface.

Example 27: The prosthetic foot of any of the Examples 19-30 or any other embodiment described herein, wherein the fin increases a stiffness of the body.

Example 28: The prosthetic foot of any of the Examples 19-30 or any other embodiment described herein, wherein the body comprises carbon fiber layers including a plurality of fibers.

Example 29: The prosthetic foot of any of the Examples 19-30 or any other embodiment described herein, wherein the each of the plurality of fibers extends parallel to each other along a length of the body.

Example 30: The prosthetic foot of any of the Examples 19-30 or any other embodiment described herein, wherein the body has a proximal portion with a first width transverse to a longitudinal axis of the prosthetic foot, wherein the body has a distal portion with a second width transverse to the longitudinal axis of the prosthetic foot, wherein the second width is greater than the first width.

Example 31: A prosthetic foot comprising a first footplate extending between a proximal portion and a distal portion, the proximal and distal portions configured to operatively engage a support surface during ambulation, and a second footplate extending between a proximal portion and a distal portion, the distal portion coupled to the first footplate at an intermediate location between the proximal and distal portions of the first footplate, the second footplate having an anterior surface, a posterior surface opposite the anterior surface, and a fin on the posterior surface.

Example 32: The prosthetic foot of any of the Examples 31-42 or any other embodiment described herein, further comprising a third footplate extending between a proximal portion and a distal portion and arranged adjacent the anterior surface of the second footplate along at least a portion of the third footplate.

Example 33: The prosthetic foot of any of the Examples 31-42 or any other embodiment described herein, wherein the distal portion of third footplate is spaced from the second footplate when the prosthetic foot is in stance, and configured to operatively engage the second footplate in dorsiflexion.

Example 34: The prosthetic foot of any of the Examples 31-42 or any other embodiment described herein, further comprising a spacer between second and third footplate.

Example 35: The prosthetic foot of any of the Examples 31-42 or any other embodiment described herein, wherein the spacer has side edges proximate at least a portion of side edges of the second footplate.

Example 36: The prosthetic foot of any of the Examples 31-42 or any other embodiment described herein, wherein the spacer has groove on bottom along longitudinal axis of spacer.

Example 37: The prosthetic foot of any of the Examples 31-42 or any other embodiment described herein, wherein the second footplate is generally L-shaped.

Example 38: The prosthetic foot of any of the Examples 31-42 or any other embodiment described herein, wherein the distal portion of second footplate has a bottom portion that folds under another portion of the second footplate, the bottom portion coupled to the first footplate.

Example 39: The prosthetic foot of any of the Examples 31-42 or any other embodiment described herein, wherein the second footplate is generally Z-shaped.

Example 40: The prosthetic foot of any of the Examples 31-42 or any other embodiment described herein, wherein the second footplate has a slot that extends along at least a portion of a length of the second footplate and defines separate blades of the second footplate.

Example 41: The prosthetic foot of any of the Examples 31-42 or any other embodiment described herein, wherein the slot extends across an end of the fin.

Example 42: The prosthetic foot of any of the Examples 31-42 or any other embodiment described herein, wherein the second footplate has transverse cross-section with a linear anterior edge and a posterior edge that defines a curved ridge that extends from linear sides.

Example 43: A sole for a limb support device comprising a body. The body comprising a support surface configured to receive thereon a body portion of the limb support device, side supports extending upwards from side edges of the support surface, a slot at a distal end of the body that is configured to receive a distal end of the body portion of the limb support device, and an attachment mechanism configured to releasably engage the limb support device to inhibit decoupling of the body from the limb support device.

Example 44: The sole of any of the Examples 43-48 or any other embodiment described herein, wherein the body comprises an engagement surface opposite from the support surface and configured to receive and engage the body portion of the limb support device.

Example 45: The sole of any of the Examples 43-48 or any other embodiment described herein, wherein the attachment mechanism comprises a recess formed on the engagement surface, the recess configured to engage a corresponding protrusion of the prosthetic device and secure the body to the prosthetic device.

Example 46: The sole of any of the Examples 43-48 or any other embodiment described herein, wherein the recess and the corresponding protrusion are at least partially coupled via a magnetic force therebetween, the magnetic force provided by one or more magnets or magnetic portions in or on the body that magnetically engage one or more magnets or magnetic portions in or on the body portion of the limb support device.

Example 47: The sole of any of the Examples 43-48 or any other embodiment described herein, wherein the attachment mechanism comprises a slit disposed about a proximal end of the engagement surface, the slit configured to receive the body portion of the limb support device therethrough.

Example 48: The sole of any of the Examples 43-48 or any other embodiment described herein, wherein the attachment mechanism comprises a retaining member configured to positioned about a neck of the prosthetic device and wrap around both the prosthetic device and the body.

Example 49: The sole for a limb support device comprising a sole body, an intermediate device coupled to the body, and an attachment mechanism. The intermediate device comprising a support surface configured to receive thereon a body portion of a limb support device during use, and a slot positioned at a distal end of the intermediate device, the slot configured to receive a distal end of the body portion of the limb support device and having a opening corresponding to a shape of a distal portion of the foot portion of the limb support device. The attachment mechanism configured to couple the intermediate device to the limb support device, the attachment mechanism configured to draw one or both of the sole body and the intermediate device proximally relative to the limb support device to securely fit to the limb support device.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment may be used with a different embodiment described herein and the combination still fall within the scope of the disclosure. It should be understood that various features and aspects of the disclosed embodiments may be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations, one or more features from a claimed combination may, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described may be incorporated in the example methods and processes. For example, one or more additional operations may be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems may generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "may," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A composite article manufactured from layers of composite material, the composite article comprising:
    a first portion having a first width;
    a second portion distally positioned from the first portion and having a second width different than the first width;
    a transition portion located between the first portion and the second portion, the transition portion having at least a first contour transitioning between the first width and the second width;
    a plurality of layers of fibrous material extending and continuous between the first portion and the second portion;
    and a first polymer impregnated with the plurality of layers of fibrous material and polymerized during a curing process, the first polymer causing the plurality of layers of fibrous material to realign to a shape substantially similar to the first contour during the curing process;
    and a fin formed on a posterior surface of the first portion of the composite article, wherein the fin is configured to increase or maintain stiffness of the composite article with less material than would be required without the fin;
    wherein the composite article is one of a prosthetic foot or a crutch blade.

2. The composite article of claim 1, wherein the first portion is located at a first end of the composite article, and wherein the second portion is located at a second end of the composite article.

3. The composite article of claim 1, wherein the first polymer is impregnated with the plurality of layers after the plurality of layers are placed into a mold having a desired shape comprising at least the first contour.

4. The composite article of claim 1, wherein the fin comprises at least a portion of the plurality of layers of fibrous material.

5. A limb support device comprising:
a body comprising:
a proximal portion with a first width;
a distal portion with a second width greater than the first width;
a transition portion between the proximal portion and the distal portion, the transition portion with a tapered width that transitions from the first width to the second width;
a plurality of layers of fibrous material having a plurality of fibers, each of the plurality of fibers extending linearly and continuously along each of the proximal portion, the transition portion, and the distal portion, the plurality of fibers generally parallel to each other and to outer edges of the proximal portion, the distal portion, and the transition portion; and
a fin formed on a posterior surface of the proximal portion of the limb support device, wherein the fin is configured to increase or maintain stiffness of the limb support device with less material than would be required without the fin.

6. The limb support device of claim 5, wherein the limb support device is a prosthetic foot.

7. The limb support device of claim 5, wherein the limb support device is a blade of a crutch.

8. The limb support device of claim 5, wherein one or more of the proximal portion, the distal portion, and the transition portion comprises a non-rectangular cross-section.

9. The limb support device of claim 5, wherein the fin has a greater thickness than adjacent portions of the body.

10. The limb support device of claim 9, wherein the fin extends generally along an axial centerline of the body.

11. The limb support device of claim 5, wherein one or more of the proximal portion, the distal portion, and the transition portion comprises a cross-section comprising:
a front surface and a rear surface, the front surface and the rear surface generally parallel to each other;
a left edge and a right edge, the left edge and the right edge generally parallel to each other,
a first chamfer between the left edge and either one of the rear surface or the front surface; and
a second chamfer between the right edge and either one of the rear surface or the front surface.

12. A limb support device comprising:
a first portion having a first dimension along a first axis;
a second portion having a second dimension along the first axis;
a plurality of layers of fibrous material extending and continuous between the first portion and the second portion;
a first polymer impregnating the plurality of layers of fibrous material and polymerized during a curing process, the first polymer causing the plurality of layers of fibrous material to realign to a shape corresponding to a contour of an intermediate portion of the limb support device between the first portion and the second portion during the curing process; and
a fin formed on a posterior surface of the first portion of the limb support device, wherein the fin is configured to increase or maintain stiffness of the limb support device with less material than would be required without the fin.

13. The limb support device of claim 12, wherein the fin comprises at least a portion of the plurality of layers of fibrous material.

* * * * *